United States Patent
Alphandéry

(10) Patent No.: US 11,633,616 B2
(45) Date of Patent: Apr. 25, 2023

(54) MAGNETIC FIELD OSCILLATING AT SEVERAL FREQUENCIES FOR IMPROVING EFFICACY AND/OR REDUCING TOXICITY OF MAGNETIC HYPERTHERMIA

(71) Applicant: NANOBACTERIE, Paris (FR)

(72) Inventor: Edouard Alphandéry, Paris (FR)

(73) Assignee: NANOBACTERIE, Paris (FR)

( * ) Notice: Subject to any disclaimer, the term of this patent is extended or adjusted under 35 U.S.C. 154(b) by 1105 days.

(21) Appl. No.: 16/325,486

(22) PCT Filed: Feb. 12, 2018

(86) PCT No.: PCT/IB2018/000218
§ 371 (c)(1),
(2) Date: Feb. 14, 2019

(87) PCT Pub. No.: WO2018/150266
PCT Pub. Date: Aug. 23, 2018

(65) Prior Publication Data
US 2019/0192871 A1  Jun. 27, 2019

(30) Foreign Application Priority Data
Feb. 16, 2017  (EP) .................................. 17290023

(51) Int. Cl.
*A61N 1/40* (2006.01)
*A61K 41/00* (2020.01)
*A61N 2/00* (2006.01)

(52) U.S. Cl.
CPC .......... *A61N 1/406* (2013.01); *A61K 41/0052* (2013.01); *A61N 2/002* (2013.01)

(58) Field of Classification Search
CPC ..... A61K 41/0052; A61N 2/002; A61N 1/406
See application file for complete search history.

(56) References Cited

U.S. PATENT DOCUMENTS

| 2005/0090732 A1* | 4/2005 | Ivkov | A61P 25/28 324/318 |
| 2006/0211939 A1* | 9/2006 | Gleich | A61N 2/02 600/410 |

(Continued)

FOREIGN PATENT DOCUMENTS

WO  2016/059283 A1  4/2016

OTHER PUBLICATIONS

International Search Report and Written Opinion of the International Searching Authority dated May 25, 2018 in corresponding International application No. PCT/IB2018/000218; 15 pages.

*Primary Examiner* — Christine H Matthews
*Assistant Examiner* — Joshua Daryl D Lannu
(74) *Attorney, Agent, or Firm* — Maier & Maier, PLLC

(57) ABSTRACT

Magnetic nanoparticles for use in a magnetic hyperthermia therapeutic treatment, prophylactic treatment or diagnosis method, wherein the magnetic nanoparticles are administered to a body part of an individual and the body part is exposed to a magnetic field oscillating at a high frequency and at a medium and/or low frequency, wherein the high frequency is 1 MHz at the most, the medium frequency is lower than the high frequency, and the low frequency is lower than the high frequency and lower than the medium frequency when it is present.

21 Claims, 9 Drawing Sheets

(56) References Cited

U.S. PATENT DOCUMENTS

| | | |
|---|---|---|
| 2007/0196281 A1 | 8/2007 | Jin et al. |
| 2007/0250139 A1 | 10/2007 | Kanzius |
| 2010/0259259 A1 | 10/2010 | Zahn et al. |
| 2011/0034974 A1 | 2/2011 | Munoz Marquez et al. |
| 2011/0212163 A1* | 9/2011 | Hoare ................. A61P 9/00 514/769 |
| 2015/0064103 A1* | 3/2015 | Guardia Giros ....... C01G 49/08 423/632 |
| 2016/0346391 A1 | 12/2016 | Friedman et al. |

* cited by examiner

MAGNETIC FIELD OSCILLATING AT SEVERAL FREQUENCIES FOR IMPROVING EFFICACY AND/OR REDUCING TOXICITY OF MAGNETIC HYPERTHERMIA

FIELD OF THE INVENTION

The invention relates to the use of a magnetic field, oscillating at several frequencies, to improve the efficacy and to decrease the toxicity of a treatment by magnetic hyperthermia.

BACKGROUND

Magnetic hyperthermia is a method in which nanoparticles are heated under the application of an oscillating magnetic field. Such method can be used as a treatment, for example when magnetic nanoparticles are introduced in or sent to tumors and heated under the application of an oscillating magnetic field, leading to antitumor efficacy. One way to achieve high efficacy of such treatment is to use nanoparticles with a high heating power or a large specific absorption rate (SAR), where the SAR is usually measured in Watt per gram of nanoparticle. Various studies introduce nanomaterials with high SAR. However, there appears to be a limit on the maximum achievable SAR. Concerning the most commonly used nanoparticles for magnetic hyperthermia, i.e. iron oxide nanoparticles, it has been suggested to increase their size to increase their SAR. This has in particular been made possible by using magnetosomes, which are iron oxide nanoparticles synthesized biologically by magnetotactic bacteria (Alphandery et al. (2011) ACS Nano, Vol. 5, P. 6279). Improvement in nanoparticle heating properties by increasing nanoparticle sizes is however limited since nanoparticles larger than 100 nm usually become multidomain and thus lose their magnetic properties. It has also been suggested to increase nanoparticle SAR by increasing nanoparticle magnetic anisotropy, but this has usually been achieved by using nanoparticles doped with toxic transition metals such as cobalt, which must be avoided for medical applications.

SUMMARY

In this invention, we introduce a new method to improve the efficacy of a magnetic hyperthermia treatment and to reduce its toxicity. This method consists in exposing magnetic nanoparticles contained in the tissue or organ to be treated, such as a tumor, to an oscillating magnetic field, which oscillates at two or more different frequencies. One frequency is preferentially called a high oscillation frequency. It preferentially lies between $10^{-3}$ kHz and $10^{6}$ kHz, or between $10^{-2}$ kHz and $10^{5}$ kHz, or between $10^{-1}$ kHz and $10^{4}$ kHz, or between 1 kHz and $10^{3}$ kHz, or between 50 kHz and 200 kHz, and is preferentially used to heat the magnetic nanoparticles. In some cases, the high frequency is lower than $10^{9}$, $10^{8}$, $10^{6}$, $10^{5}$, $10^{4}$, $10^{3}$, $10^{2}$, 10, or 1 kHz. In some cases, the high frequency is larger than $10^{-9}$, $10^{-7}$, $10^{-5}$, $10^{-3}$, $10^{-1}$, 1, 10, 50, 100, or 1000 kHz. Another frequency is preferentially called a medium frequency. It preferentially lies between 0.5 Hz and 250 000 kHz, or between 5 Hz and 25000 kHz, or between 50 Hz and 250 kHz, or between 500 Hz and 25 kHz, and preferentially enables to reach a higher or larger maximum magnetic field or a higher or larger high frequency of oscillation. In some cases, the medium frequency is lower than $10^{9}$, $10^{7}$, $10^{5}$, $10^{3}$, or 10 kHz. In some other cases, the medium frequency is larger than $10^{-5}$, $10^{-3}$, $10^{-1}$, 1, 10, 100, 500, $10^{3}$, or $10^{4}$ Hz. Still another frequency is preferentially called a low frequency. It is preferentially between $10^{-9}$ Hz and $10^{3}$ Hz, or between $10^{-8}$ Hz and $10^{2}$ Hz, or between $10^{-7}$ Hz and 10 Hz, or between $10^{-6}$ Hz and 1 Hz, or between $10^{-5}$ Hz and 1 Hz, or between $10^{-4}$ Hz and 1 Hz, or between $10^{-3}$ Hz and 1 Hz, or between $10^{-2}$ Hz and 1 Hz, or between $10^{-1}$ Hz and 1 Hz. It is preferentially lower than $10^{3}$, $10^{2}$, 10, 1, or $10^{-1}$ Hz, and preferentially enables to induce heating and cooling steps. It is preferentially larger than $10^{-9}$, $10^{-8}$, $10^{-7}$, $10^{-6}$, $10^{-5}$, $10^{-4}$, $10^{-3}$, $10^{-2}$, $10^{-1}$, or 1 Hz.

DETAILED DESCRIPTION

This method may be advantageous for the following reasons. First, it may increase treatment safety. On the one hand, it may limit Eddy or Foucault currents and therefore possible heating of the whole organism. On the other hand, with this method it may be possible to yield anti-tumor efficacy with temperatures reached during treatment, which may globally be lower than those reached with the application of a magnetic field oscillating at only one frequency. Second, it may increase treatment efficacy by enabling the application of a series of temperature gradients, or heating and cooling steps, which may be more efficient in destroying tumors than the application of a continuous magnetic field usually producing a more constant temperature. Third, with this method it may be possible to consider a treatment in which the strength or amplitude of the applied magnetic field, the number of heating and cooling steps, the heating and cooling times, are fixed depending on the temperature that one wants to achieve. Thus, on the one hand, it may not be necessary to vary the strength or amplitude of the magnetic field applied during treatment to reach a given temperature, as is usually the case in a magnetic hyperthermia treatment. On the other hand, it may be possible to suppress the use of a temperature probe during treatment by using a pre-calibration curve that determines the strength or amplitude of the magnetic field, as well as heating and cooling times, which must be used to produce heating and cooling steps. Fourth, treatment safety may also be strengthened since overheating may be reached more rarely with a magnetic field oscillating at more than one frequency than with that oscillating at only one frequency.

The invention relates to magnetic nanoparticles for use in a magnetic hyperthermia therapeutic treatment, prophylactic treatment or diagnosis method, wherein the magnetic nanoparticles are administered to a body part of an individual and the body part is exposed to a magnetic field oscillating at a high frequency and at a medium and/or low frequency.

The invention also relates to magnetic nanoparticles for use in a magnetic hyperthermia therapeutic treatment, prophylactic treatment or diagnosis method, wherein the magnetic nanoparticles are administered to a body part of an individual and the body part is exposed to a magnetic field oscillating at a high frequency and at a medium and/or low frequency, wherein the high frequency is 1 MHz at the most, the medium frequency is lower than the high frequency, and the low frequency is lower than the high frequency and lower than the medium frequency when it is present.

In one embodiment of the invention, the individual is a human or an animal.

In one embodiment of the invention, the high frequency is lower than $10^{6}$, $10^{3}$, 10, 1, $10^{-1}$, $10^{-3}$, $10^{-6}$, $10^{-9}$, $10^{-12}$, or $10^{-15}$ MHz.

In one embodiment of the invention, the high frequency is lower than $10^6$, $10^5$, $10^4$, $10^3$, 500, 100, 50, 20, 10, 5, or 1 kHz.

In still another embodiment of the invention, the high frequency lies between 1 and $10^9$ kHz, or between 1 and $10^6$ kHz, or between 1 and $10^3$ kHz.

In another embodiment of the invention, the medium frequency is lower than the high frequency by a factor of at least 1.01, 1.1, 2, 5, 10, $10^2$, $10^3$, $10^5$ or $10^{10}$. The ratio between $f_h$ and $f_m$, $f_h/f_m$, can be larger than 1.01, 1.1, 2, 5, 10, $10^2$, $10^3$, $10^5$ or $10^{10}$.

In still another embodiment of the invention, the low frequency is lower than the high frequency and medium frequency when it is present by a factor of at least 1.01, 1.1, 2, 5, 10, $10^2$, $10^3$, $10^5$ or $10^{10}$. The ratio between $f_h$ and $f_l$, $f_h/f_l$, or the ratio between $f_m$ and $f_l$, $f_m/f_l$, can be larger than 1.01, 1.1, 2, 5, 10, $10^2$, $10^3$, $10^5$ or $10^{10}$.

The present invention also relates to a magnetic hyperthermia prophylactic, therapeutic treatment or diagnosis method of an individual, comprising administering an effective amount of magnetic nanoparticles to a body part of the individual and exposing the body part to a magnetic field oscillating at a high frequency and at a medium and/or low frequency.

In one embodiment of the invention, a magnetic field oscillating at high and medium and/or low frequency is the same as a magnetic field oscillating at high, and medium and/or low frequency. It designates a magnetic field that oscillates at high and medium frequencies or a magnetic field that oscillates at high and low frequencies or a magnetic field that oscillated at high, medium, and low frequencies.

In one embodiment of the invention, the magnetic field can designate an oscillating magnetic field, also designated as alternating magnetic field, where the oscillating magnetic field can designate a magnetic field oscillating with time, preferentially at a low frequency, $f_l$, and/or at a medium frequency, $f_m$, and/or at a high frequency, $f_h$, and/or at several frequencies, and/or at more than 1, 2, 3, 4, 5, 6, 7, 8, 9, 10, 15, 20, 25, 50, or 100 frequencies. The variations of the amplitude of the magnetic field with time are represented in FIG. 1(a) for an oscillation at $f_h$, in FIG. 1(b) for an oscillation at $f_m$ and $f_h$, in FIG. 2(b) for an oscillation at $f_m$, $f_l$, and $f_h$, in FIG. 2(c) for an oscillation at $f_h$ and $f_l$.

In one embodiment of the invention, the magnetic field is applied during high frequency sequences of duration $t_1$, $t_2$, or $t_3$ for oscillation at $f_h$ (FIG. 1(a)), medium frequency sequences of duration $t_4$, $t_5$, or $t_6$ for oscillations at $f_h$ and $f_m$ (FIG. 1(b)), low frequency sequences of duration $t_7$, or $t_8$ for oscillations at $f_h$, $f_m$, and $f_l$ (FIG. 2(b)), low frequency sequences of duration $t_9$, or $t_{10}$, for oscillations at $f_h$ and $f_l$ (FIG. 2(c)).

According to the invention, a frequency can be defined when a sequence is repeated at least 2, 3, 5, 10, 50, 100, $10^3$, $10^5$, or $10^{10}$ times, and preferentially when the durations of the different sequences associated with a given frequency vary by less than a factor of 1.1, 1.5, 2, 5, 10, $10^2$, $10^3$, $10^5$, or $10^{10}$ between these different sequences, or preferentially when the durations of the different sequences associated with a given frequency vary by a factor comprised between 1.01 and $10^{10}$, or between 1.1 and $10^7$, or between 1.1 and $10^5$, or between 1.1 and $10^3$, or between 1.1 and 100, or between 1.1 and 10, or preferentially when the durations of the different sequences associated with a given frequency vary by factor of more than 1.01, 1.1, 1.2, 1.5, 2, 5, 10, $10^3$, $10^5$, or $10^7$.

According to the invention, a frequency can be measured by using the average values of $t_1$, $t_2$, $t_3$, $t_4$, $t_5$, $t_6$, $t_7$, $t_8$, $t_9$, $t_{10}$, $t_{11}$, or $t_{12}$, also designated as $t_i$ for $1<i<12$. $t_i$ can be expressed using the relation: $t_i = \Sigma_{j=1}^{j=m} t_{i,j}$, where j represents any given sequence and m is the total number of sequences. Preferentially, m is larger than 2, 5, 10, $10^3$, or $10^6$. In some cases, m can be lower than $10^6$, $10^5$, $10^4$, $10^3$, $10^2$, 10, 9, 8, 7, 6, 5, 4, 3, or 2. In some cases, m can be comprised between 2 and $10^6$, or between 2 and $10^5$, or between 2 and $10^3$, or between 2 and 10, or between 2 and 5, or between 2 and 4, or between 2 and 3, or between 3 and 4, or between 3 and 5, or between 3 and 10, or between 3 and $10^2$, or between 3 and $10^5$, or between 3 and $10^7$.

According to the invention, a sequence of duration $t_1$, $t_2$, $t_3$, $t_4$, $t_5$, or $t_6$ can be too short to induce a temperature variation, a heating or cooling step, or a heating or cooling session.

According to the invention, $t_1$, $t_2$, or $t_3$ can be shorter than $t_4$, $t_5$, or $t_6$ to enable the medium frequency to modulate the high frequency.

According to the invention, a sequence of duration $t_7$, $t_5$, $t_9$, $t_{10}$, $t_{11}$, or $t_{12}$ can be long enough to induce a temperature variation, a heating or cooling step, or a heating or cooling session.

According to the invention, a sequence of duration $t_7$, $t_8$, $t_9$, or $t_{10}$ can be shorter than $t_{11}$, or $t_{12}$ to enable the low frequency of oscillation to produce more temperature gradients than the very low frequency, where the very low frequency preferentially corresponds to the frequency of repetition of sessions.

In one embodiment of the invention, magnetic hyperthermia designates a method, technique, or process, preferentially of treatment or diagnosis, in which magnetic nanoparticles are exposed to an oscillating magnetic field, producing (or not) a temperature increase, or producing (or not) the release of a compound from magnetic nanoparticles.

In one embodiment of the invention, the temperature increase is smaller than $10^5$, $10^3$, 150, 100, 75, 50, 25, 20, 15, 5, 2, 1, 0.1, $10^{-2}$, $10^{-3}$, or $10^{-5}$° C., preferentially above the physiological temperature or the temperature of the body part, individual, or organism, preferentially measured before or without the application of the oscillating magnetic field.

In still another embodiment of the invention, the temperature increase is larger than $10^5$, $10^3$, 150, 100, 75, 50, 25, 20, 15, 5, 2, 1, 0.1, $10^{-2}$, $10^{-3}$, or $10^{-5}$° C., preferentially above the physiological temperature or the temperature of the body part, individual, or organism, preferentially measured before or without the application of the oscillating magnetic field.

In an embodiment of the invention, the percentage of released compound is smaller than $10^{-15}$, $10^{-8}$, $10^{-4}$, $10^{-2}$, 1, 5, 10, 25, 50, 75, $10^2$, $10^4$, $10^8$, or $10^{15}$%, where this percentage can correspond to the quantity of compounds released after or during application of the oscillating magnetic field divided by the quantity of compounds bound or linked to the magnetic nanoparticles before or without the application of the oscillating magnetic field.

In still another embodiment of the invention, the percentage of released compound is larger than $10^{-15}$, $10^{-8}$, $10^{-4}$, $10^{-2}$, 1, 5, 10, 25, 50, 75, $10^2$, $10^4$, $10^8$, or $10^{15}$%. The situation where the percentage of released compound is larger than 100% is unlikely, but may for example happen if the released compound transforms itself in several compounds, hence increasing the number of released compounds.

In one embodiment of the invention, the oscillation of the magnetic field designates the oscillation or variation of the magnetic flux density, energy or power, with time, preferentially measured with a magnetic field probe in one or several directions, such as the axial and radial directions, most preferentially the axial and radial directions of a cylindrical magnetic field probe. In some cases, the magnetic flux density can be deduced from quantities such as the voltage measured by the probe, preferentially the voltage in the radial, $U_r$, and axial, $U_a$, directions, coefficients associated with the probe such as the radial and axial coefficients of the probe, $\alpha_r$ and $\alpha_a$, and one or several oscillation frequencies, preferentially the high frequency of oscillation $f_h$, most preferentially using the formula $H_r=U_r/\alpha_r f_h$ and/or $H_a=U_a\alpha_a f_h$, where $H_r$ and $H_a$ designate the magnetic flux density in the radial and axial directions, respectively.

In another embodiment of the invention, the magnetic flux density designates the strength of the magnetic field or another parameter such as the energy or power of the magnetic field.

In another embodiment of the invention, the frequency of oscillation can be estimated from the values of two times, $t_{max1}$ and $t_{max2}$, corresponding to two successive values of maximum flux density, as $f=[1/(t_{max2}-t_{max1})]$ or $f=[2\pi/(t_{max2}-t_{max1})]$. In some other cases, the frequency of oscillation can be estimated from the values of two times, $t_{min1}$ and $t_{min2}$, corresponding to two successive values of minimum flux density, as $f=[1/(t_{min2}-t_{min1})]$ or $f=[2\pi/(t_{min2}-t_{min1})]$.

These formulas may preferentially be used to measure the high and/or medium frequency of oscillation, $f_h$ and/or $f_m$.

In another embodiment of the invention, the oscillation of the magnetic field designates the variation or oscillation of the magnitude of the magnetic flux density with time, H, where H can be deduced from the magnetic flux density, preferentially measured in the axial and radial directions, most preferentially using the relation: $H=[H_r^2+H_a^2]^{1/2}$. The magnitude of magnetic flux density can also designate the amplitude of the magnetic field.

In still another embodiment of the invention, the maximum magnetic field, $H_{max}$, is defined as the maximum value of the magnitude of magnetic flux density oscillating with time. It preferentially corresponds to the maximum magnetic field amplitude estimated among the different values of local maximum magnetic field amplitude of each high frequency oscillation, designated as $H_{max,i}$.

In another embodiment of the invention, $H_{max,i}$ is a local maximum of magnetic field amplitude, estimated for each high frequency oscillation.

In still another embodiment of the invention, the average magnetic field, $H_{av}$, is defined as the average value of the different values of $H_{max,i}$, estimated for each high frequency oscillation.

In still another embodiment, $H_{max,i}$, the average or maximum magnetic field, the strength or amplitude of the magnetic field, the high, low, or medium oscillation frequency can depend on a parameter of the device generating the oscillating magnetic field, such as the intensity, power, frequency of the alternating current, and can then be estimated for the various values of such parameter. $H_{max,i}$, the average or maximum magnetic field, the strength or amplitude of the magnetic field, the high, low, or medium oscillation frequency, can also depend on the distance between the device and the magnetic nanoparticle, or on the distance between the device and the body part of the individual, or on the distance between the device and the region where one desires to apply the oscillating magnetic field, preferentially for heating magnetic nanoparticles. $H_{max,i}$, the average or maximum magnetic field, the strength or amplitude of the magnetic field, the high, low, or medium oscillation frequency can then be estimated as a function of such distance.

The description of the device generating the oscillating magnetic field is provided later in the description of the invention.

In one embodiment of the invention, the oscillating magnetic field is not generated by a medical device used for diagnosis, an MRI, a scanner, an equipment that does not generate a magnetic field oscillating at several different frequencies, or a permanent magnet.

In another embodiment of the invention, the oscillating magnetic field does not vary in space, or varies by less than $10^9$, $10^7$, $10^5$, $10^3$, 10, 1, $10^{-3}$, $10^{-5}$, $10^{-7}$, or $10^{-9}$ mT/m or $10^{-9}$ mT/cm or $10^{-9}$ mT/nm.

In one embodiment of the invention, for the magnetic field oscillating only at the high frequency, the relation between the average and maximum magnetic field can be $H_{av}=H_{max}$, or the average magnetic field can be close, preferentially slightly lower, than the maximum magnetic field. The average magnetic field can preferentially be deduced from the relation: $H_{av}=(\Sigma_{i=1}^{i=n}H_{max,i})/n$, where $H_{max,i}$ is the maximum magnitude of magnetic flux density estimated for each high frequency oscillation and n is the total number of high frequency oscillations.

In one embodiment of the invention, we consider that the magnetic field oscillates only at high frequency when the maximum magnetic field amplitude estimated for each high frequency oscillation does not vary, increase and/or decrease, or preferentially varies, increases and/or decreases, by less than 80, 60, 50, 40, 20, 10, 5, 2, or 1%. This percentage of variation is measured over a period of time that is preferentially lower than the heating and cooling times associated with the low frequency of oscillation, most preferentially lower than 1, $10^{-1}$, $10^{-2}$, $10^{-3}$, $10^{-4}$, $10^{-5}$, $10^{-6}$, $10^{-7}$, $10^{-8}$, $10^{-9}$, $10^{-10}$, $10^{-11}$, or $10^{-12}$ seconds.

In another embodiment of the invention, we consider that the magnetic field oscillates at high and medium frequency when the maximum magnetic field amplitude estimated for each high frequency oscillation, $H_{max,i}$, varies, increases and/or decreases, preferentially by more than 80, 60, 50, 40, 20, 10, 5, 2, or 1%. This percentage of variation is measured over a period of time that is preferentially lower than the heating and cooling times associated with the low frequency of oscillation, most preferentially lower than 1, $10^{-1}$, $10^{-2}$, $10^{-3}$, $10^{-4}$, $10^{-5}$, $10^{-6}$, $10^{-7}$, $10^{-8}$, $10^{-9}$, $10^{-10}$, $10^{-11}$, or $10^{-12}$ seconds.

In another embodiment of the invention, for the magnetic field oscillating at the high and medium frequency, the maximum magnetic field, $H_{max}$, is the maximum amplitude of the magnetic field, estimated among n high oscillation frequencies, and/or estimated among n values of $H_{max,i}$.

In another embodiment of the invention, for the magnetic field oscillating at the high and medium frequency, the average magnetic field, $H_{av}$, can be deduced from the relation: $H_{av}=(\Sigma_{i=1}^{i=n}H_{max,i})/n$, where $H_{max,i}$ is the maximum amplitude of the magnetic field estimated for each high frequency oscillation and n is the total number of high frequency oscillations, which are measured.

In one embodiment of the invention, for the magnetic field oscillating at the high and medium frequency, there is a relation between the maximum and average magnetic field and the average magnetic field can hence be deduced from the maximum magnetic field.

In one embodiment of the invention, for the magnetic field oscillating at the high, medium, and low frequency, the average magnetic field, estimated during the two sequences of times $t_7$ and $t_8$ (FIG. 2(b)) is defined as the average value between the average magnetic field estimated during the $A_7$ low frequency sequence, $H_{A7}$, and the average magnetic field estimated during the $A_8$ low frequency sequence, $H_{A8}$, as $H_{av}=[(t_7 \cdot H_{A7}+t_8 \cdot H_{A8})/(t_7+t_8)]$.

In some cases, a sequence can correspond to one or several session(s) or a session can correspond to one or several sequence(s).

In one embodiment of the invention, for the magnetic field oscillating at the high, and low frequency, the average magnetic field, estimated during the times $t_9$ and $t_{10}$ (FIG. 2(c)), is defined as the average value between the average magnetic field estimated during the $A_9$ low frequency sequence, $H_{A9}$, and the average magnetic field estimated during the $A_{10}$ low frequency sequence, $H_{A10}$, as $H_{av}=[(t_9 \cdot H_{A9}+t_{10} \cdot H_{A10})/(t_9+t_{10})]$.

In one embodiment of the invention, $t_7$, $H_{A7}$, $t_8$, $H_{A8}$, $t_9$, $H_{A9}$, $t_{10}$, or $H_{A10}$, is/are average value(s) estimated from several $A_7$, $A_8$, $A_9$, or $A_{10}$ low frequency sequences.

In another embodiment of the invention, $A_7$, $A_8$, $A_9$, or $A_{10}$, correspond to the magnetic field amplitude, estimated during the $A_7$, $A_8$, $A_9$, or $A_{10}$ low frequency sequence.

In one embodiment of the invention, for the magnetic field oscillating at the high, medium, and low frequency, the maximum magnetic field is defined as the maximum magnetic field estimated during the $A_7$ low frequency sequence.

In one embodiment of the invention, for the magnetic field oscillating at the high and low frequency, the maximum magnetic field is defined as the maximum magnetic field estimated during the $A_9$ low frequency sequence.

The definitions of the sequences and times associated with them are provided later in the description.

In one embodiment of the invention, there is a stabilization time after the device generating the oscillating magnetic field has been switched on during which the magnetic field strength or amplitude preferentially increases until it reaches a plateau corresponding to magnetic field stabilization. In some cases, this stabilization time is longer than 1, 10, 50, 100, 200, 500, or 1000 seconds. In some cases, this stabilization time is shorter than 1, 10, 50, 100, 200, 500, or 1000 seconds.

In another embodiment of the invention, a stable magnetic field has not been reached before the stabilization time and the magnetic field is then designated as an unstable magnetic field. Such unstable magnetic field can be characterized by a maximum or average magnetic field that varies by more than 80, 50, 20, 10, 5, 2, or 1% with time, where this percentage is preferentially measured during a period of time of less than 60, 30, 15, 5, 1, or 0.1 minute.

In another embodiment of the invention, the average and maximum magnetic field, or the magnetic field strength or amplitude, of an unstable magnetic field can be estimated by multiplying the value of the average or maximum magnetic field, or of the magnetic field strength or amplitude, obtained for the same magnetic field, estimated after stabilization, by a factor, preferentially comprised between 0 and 1. The relation between stable and unstable magnetic field can preferentially be estimated using a pre-calibration curve that estimates the variation of the amplitude or strength of the magnetic field, or maximum or average magnetic field, as a function of time, preferentially within the stabilization time period, preferentially estimated with the magnetic field probe, most preferentially estimated for the device that generates the oscillating magnetic field. This relation can depend on a parameter of the device generating the oscillating magnetic field, such as the intensity, power, frequency of the alternating current, and can hence be estimated for the various values of such parameter. This relation can also depend on the distance between the device and the magnetic nanoparticle or on the distance between the device and the body part of the individual, or on the distance between the device and the region where one desires to apply the oscillating magnetic field, preferentially for heating magnetic nanoparticles. This relation can hence be estimated as a function of such distance.

In one embodiment of the invention, the oscillating magnetic field designates a magnetic field whose strength varies as a function of time between positive and negative values. The absolute value of the magnetic field strength corresponds to the amplitude of the oscillating magnetic field. The maximum and minimum strengths, of opposite signs, are usually of equal amplitude, but it can happen that maximum and minimum strengths differ by more than 1, 5, 10, 50, 75, or 80%.

In still another embodiment of the invention, the frequency of oscillation of the magnetic field, f, and associated period, T, where T and f are preferentially related to each other by the formula $T=1/f$, vary with parameters such as time of application of the oscillating magnetic field, current intensity, distance between the device generating the magnetic field and the magnetic nanoparticle, distance between the device generating the magnetic field and the body part of the individual, or the parameter of the device. It is then preferentially possible to define a frequency of oscillation or associated period for each value of such parameter i as $f_i$ and $T_i=1/f_i$. In this case, it may also be possible to define an average frequency of oscillation and associated period over n different values of such parameter as: $f_{av}=(\Sigma_{i=1}^{i=n}f_i)/n$ and $T_{av}=(\Sigma_{i=1}^{i=n}T_i)/n$. It may also be possible to define the maximum frequency of oscillation and associated period, $f_{max}$ and $T_{max}$, as the maximum values of $f_i$ and $T_i$ over n different values of such parameter. It may also be possible to define the average frequency of oscillation and associated period as: $H_{av}=(\Sigma_{i=1}^{i=n}T_i H_{max,i})/(\Sigma_{i=1}^{i=n}T_i)$.

In still another embodiment of the invention, the frequency of oscillation, f, and associated period, T, where $T=1/f$, vary with parameters such as time, current intensity, distance between the device generating the magnetic field and the magnetic nanoparticle, the distance between the device generating the oscillating magnetic field and the body part of the individual, or the parameter of the device, it is possible to determine a relation between the variation of the oscillation frequency, $\Delta f$, or of the variation of its associated period, $\Delta T$, and the variation of parameters, such as variations of the time of application of the oscillating magnetic field, of current intensity, of distance between the device generating the magnetic field and the magnetic nanoparticle, of distance between the device generating the magnetic field and the body part of the individual, or of the parameter of the device.

In still another embodiment of the invention, the frequency of oscillation $f_i$, or associated period, $T_i$, is different from another frequency of oscillation $f_j$, or from another associated period, $T_j$, when $[(f_i-f_j)/f_i]$ or $[(T_i-T_j)/T_i]$ is larger than 1, 5, 10, 25, 50, 70, 80, or 90%.

In still another embodiment of the invention, the frequency of oscillation $f_i$, or associated period, $T_i$, is the same as the frequency of oscillation $f_j$, or associated period, $T_j$, when $[(f_i-f_j)/f_i]$ or $[(T_i-T_j)/T_i]$ is lower than 1, 5, 10, 25, 50, 70, 80, or 90%.

In still another embodiment of the invention, the high, the medium, and/or the low frequency of oscillation of the magnetic field, comprises more or less than 1, 2, 3, 4, 5, 6, 7, 8, 9, 10, 20, 50, or 100 different frequencies of oscillation.

In still another embodiment of the invention, the strength or amplitude of the magnetic field, the average or maximum magnetic field, can be varied or adjusted by varying the intensity of the alternating current that generates the oscillating magnetic field, preferentially from $10^{-20}$ to $10^{20}$ A, from $10^{-15}$ to $10^{15}$ A, from $10^{-10}$ to $10^{10}$ A, from $10^{-5}$ to $10^5$ A, from $10^{-4}$ to $10^4$ A, from $10^{-3}$ to $10^3$ A, or from 0 to 500 A (Ampere).

In still another embodiment of the invention, the strength or amplitude of the magnetic field, the average or maximum magnetic field, can be varied or adjusted by increasing the intensity of the alternating current that generates the oscillating magnetic field above $10^{-20}$, $10^{-10}$, $10^{-5}$, $10^{-3}$, $10^{-1}$, 1, 10, $10^2$, 500, $10^3$, or $10^5$ A.

In still another embodiment of the invention, the strength or amplitude of the magnetic field, the average or maximum magnetic field, can be varied or adjusted by varying the power of the equipment generating the alternating current, preferentially from $10^{-20}$ to $10^{20}$ W, from $10^{-15}$ to $10^{15}$ W, from $10^{-10}$ to $10^{10}$ W, from $10^{-5}$ to $10^5$ W, from $10^{-4}$ to $10^4$ W, from $10^{-3}$ to $10^3$ W, or from 0 to 500 W (Watt).

In still another embodiment of the invention, the strength or amplitude of the magnetic field, the average or maximum magnetic field, can be varied or adjusted by setting the power of the equipment generating the alternating current to a value, which is larger than $10^{-20}$, $10^{-10}$, $10^{-5}$, $10^{-3}$, $10^{-1}$, 1, 10, $10^2$, $10^3$, or $10^5$ W or W per cm$^3$ of exposed body part.

In still another embodiment of the invention, the strength or amplitude of the magnetic field, the average or maximum magnetic field, can be varied or adjusted by varying the distance separating the device generating the alternating currents from the magnetic nanoparticles or from the body part of the individual, preferentially by or to a distance comprised between $10^{-20}$ to $10^{20}$ cm, from $10^{-15}$ to $10^{15}$ cm, from $10^{-10}$ to $10^{10}$ cm, from $10^{-5}$ to $10^5$ cm, from $10^{-4}$ to $10^4$ cm, from $10^{-3}$ to $10^3$ cm, or from 0 to 500 cm. In some cases, the distance separating the device generating the alternating currents from the magnetic nanoparticles or from the body part of the individual is larger than $10^{-20}$, $10^{-15}$, $10^{-10}$, $10^{-5}$, $10^{-4}$, $10^{-3}$, $10^{-1}$, 1, 5, 10, or 20 cm.

In one embodiment of the invention, the amplitude of the oscillating magnetic field varies by more than $10^{-9}$, $10^{-6}$, $10^{-4}$, $10^{-2}$, 1, 10, $10^3$, $10^4$, or $10^6$ mT per μm, per cm, or per μm. In this case, it may be possible that the oscillating magnetic field induces a movement of the magnetic nanoparticles, of more than $10^{-5}$, $10^{-3}$, $10^{-1}$, 1, 10, $10^2$, $10^3$, $10^5$, $10^8$, or $10^{11}$ μm.

In another embodiment of the invention, the amplitude of the oscillating magnetic field varies by less than $10^{-9}$, $10^{-6}$, $10^{-4}$, $10^{-2}$, 1, 10, $10^3$, $10^4$, or $10^6$ mT per μm, per cm, or per m. In this case, it may be possible that the oscillating magnetic field does not induce any movement of the magnetic nanoparticles, or a movement of less than $10^{-5}$, $10^{-3}$, $10^{-1}$, 1, 10, $10^2$, $10^3$, $10^5$, $10^8$, or $10^{11}$ μm.

In one embodiment of the invention, the nanoparticle, also designated as (the) nanoparticle(s) or as (the) magnetic nanoparticle(s), designates an assembly of more than 1, 2, 5, 10, $10^2$, $10^3$, $10^5$, $10^7$, $10^{10}$, $10^{20}$, or $10^{50}$ magnetic nanoparticle(s).

In one embodiment of the invention, an oscillating magnetic field, preferentially oscillating at high frequency, or at high and medium frequency, is a magnetic field whose strength or amplitude oscillates with time, where one oscillation corresponds to the repetition of the same sequence more than once or to two or three different sequences, where sequences are defined as: i), a sequence of magnetic field amplitude or strength increase during a time $t_1$ associated to the high frequency, or a sequence of magnetic field amplitude or strength increase during a time $t_4$ associated to the medium frequency, ii), a sequence of magnetic field amplitude or strength decrease during a time $t_2$ associated to the high frequency, or a sequence of magnetic field amplitude or strength decrease during a time $t_5$ associated to the medium frequency, iii), a sequence of constant magnetic field amplitude or strength during a time $t_3$ associated to the high frequency, or a sequence of constant magnetic field amplitude or strength during a time $t_6$ associated to the medium frequency. During $t_3$ or $t_6$, the magnetic field is preferentially of zero strength or amplitude. FIGS. 1(a) and 1(b) represent schematic pictures of the variation of magnetic field amplitude with time with indications of the different sequences for the magnetic field oscillating only at high frequency (FIG. 1(a)) or at high and medium frequency (FIG. 1(b)). Preferentially, sequences in FIG. 1(a) are designated as high frequency sequences while those in FIG. 1(b) correspond to medium frequency sequences.

In one embodiment of the invention, a sequence of magnetic field increase, for the magnetic field, preferentially oscillating at the high or high and medium frequency, corresponds to the time period $t_1$ or $t_4$ during which the amplitude of the magnetic field increases, preferentially continuously, by more than 0.001, 0.01, 0.1, 1, 2, 5, 10, or 20 mT, or from less than 0, 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 500, or 1000 mT, to more than 0, 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 500, or 1000 mT, or by more than 0.001, 0.01, 0.1, 1, 2, 5, 10, 50, 75, 90, 90, or 100%. This percentage can correspond to $[2(A_{max}-A_{min})/(A_{max}+A_{min})]$, where $A_{max}$ and $A_{min}$ are the maximum and minimum amplitudes of the oscillating magnetic field during the time $t_1$ or $t_4$, respectively.

In one embodiment of the invention, a sequence of magnetic field increase, for the magnetic field, preferentially oscillating at the high or high and medium frequency, corresponds to the time period $t_1$ or $t_4$ during which the strength of the magnetic field increases, preferentially continuously, increases by more than 0.001, 0.01, 0.1, 1, 2, 5, 10, or 20 mT, or from less than −1000, −500, −100, −95, −85, −80, −75, −70, −65, −60, −55, −50, −45, −40, −35, −30, −25, −20, −15, −14, −13, −12, −11, −10, −9, −8, −7, −6, −5, −4, −3, −2, or −1 mT to more than 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 500, or 1000 mT, or increases by more than 0.001, 0.01, 0.1, 1, 2, 5, 10, 50, 75, 90, 90, or 100%. This percentage can correspond to $[2(S_{max}-S_{min})/(S_{max}+S_{min})]$, where $S_{max}$ and $S_{min}$ are the maximum and minimum strengths of the oscillating magnetic field during the time $t_1$ or $t_4$, respectively.

In one embodiment of the invention, a sequence of magnetic field decrease, for the magnetic field, preferentially oscillating at the high or high and medium frequency, corresponds to the time period $t_2$ or $t_5$ during which the amplitude of the magnetic field decreases, preferentially continuously, by more than 0.001, 0.01, 0.1, 1, 2, 5, 10, or 20 mT, from more than 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 500, or 1000 mT, to less than 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 500, or 1000 mT, or by more than 0.1, 1, 2, 5, 10, 50, 75, 90, 90, or 100%. This percentage can correspond to $[2(A_{max}-A_{min})/(A_{max}+A_{min})]$, where $A_{max}$ and $A_{min}$ are the maximum and minimum amplitudes of the oscillating magnetic field during the time $t_2$ or $t_5$, respectively.

In one embodiment of the invention, a sequence of magnetic field decrease, for the magnetic field, preferentially oscillating at the high or medium and high frequency, corresponds to the time period $t_2$ or $t_5$ during which the strength of the magnetic field decreases, preferentially continuously, decreases by more than 0.001, 0.01, 0.1, 1, 2, 5, 10, or 20 mT, or decreases from less than 1000, 500, 100, 95, 85, 80, 75, 70, 65, 60, 55, 50, 45, 40, 35, 30, 25, 20, 15, 14, 13, 12, 11, 10, 9, 8, 7, 6, 5, 4, 3, 2, or 1 mT to more than −1, −2, −3, −4, −5, −6, −7, −8, −9, −10, −11, −12, −13, −14, −15, −20, −25, −30, −35, −40, −45, −50, −55, −60, −65, −70, −75, −80, −85, −90, −95, −100, −500, or −1000 mT, or decreases by more than 0.001, 0.01, 0.1, 1, 2, 5, 10, 50, 75, 80, 90, or 100%. This percentage can correspond to $[2(S_{max}-S_{min})/(S_{max}+S_{min})]$, where $S_{max}$ and $S_{min}$ are the maximum and minimum strengths of the oscillating magnetic field during the time $t_2$ or $t_5$, respectively.

In one embodiment of the invention, a sequence of constant magnetic field, for the magnetic field, preferentially oscillating at the high or medium frequency, corresponds to the time period $t_3$ or $t_6$ during which the amplitude of the applied magnetic field is constant, i.e. does not vary by more than 0.01, 0.1, 1, 2, 5, 10, or 20 mT, or by more than 1, 5, 10, 25, or 50%. This percentage can correspond to $[2(A_{max}-A_{min})/(A_{max}+A_{min})]$, where $A_{max}$ and $A_{min}$ are the maximum and minimum amplitudes of the oscillating magnetic field during the time $t_3$ or $t_6$, respectively.

In another embodiment of the invention, a sequence of constant magnetic field, for the magnetic field, preferentially oscillating at the high or high and medium frequency, corresponds to the time period $t_3$ or $t_6$ during which the strength of the applied magnetic field is constant, i.e. does not vary by more than 0.01, 0.1, 1, 2, 5, 10, or 20 mT, or by more than 1, 5, 10, 25, or 50%. This percentage can correspond to $[2(S_{max}-S_{min})/(S_{max}+S_{min})]$, where $S_{max}$ and $S_{min}$ are the maximum and minimum amplitudes of the oscillating magnetic field during the time $t_3$ or $t_6$, respectively.

In one embodiment of the invention, a sequence of constant magnetic field, for the magnetic field, preferentially oscillating at the high or high and medium frequency, can be a sequence of zero magnetic field and correspond to the time period $t_3$ or $t_6$ during which the magnetic field is not applied or is applied but with a strength or amplitude close to 0, preferentially an amplitude, which is lower than or equal to 100, 50, 25, 10, 5, 2, 1, $10^{-1}$, $10^{-2}$, $10^{-3}$, $10^{-6}$, $10^{-9}$ mT, or 0 mT.

In one embodiment of the invention, sequences of increase, decrease, or constant magnetic field follow each other in any order.

In one embodiment of the invention, a cycle of the magnetic field, preferentially oscillating at the high or high and medium frequency, corresponds to a combination of at least two sequences.

In one embodiment of the invention, a sequence or a cycle, for the magnetic field, preferentially oscillating at the high or high and medium frequency, is repeated more than 2, 3, 4, 5, 10, $10^2$, $10^3$, $10^4$, $10^5$, $10^{10}$, $10^{25}$, $10^{50}$, or $10^{100}$ times.

In another embodiment of the invention, for the magnetic field, preferentially oscillating at the high or high and medium frequency, high frequency sequences of increase, decrease, and constant magnetic field, taking place during a time $t_1+t_2+t_3$ are associated with a high frequency cycle of high frequency $f_h$ equal or proportional to $[2\pi/(t_1+t_2+t_3)]$, or $[1/(t_1+t_2+t_3)]$, preferentially when the frequency is estimated from the variation of the strength of the magnetic field with time, or are associated with a high frequency cycle of high frequency $f_h$ equal or proportional to $[\pi/(t_1+t_2+t_3)]$, or $[½·(t_1+t_2+t_3)]$, preferentially when the frequency is estimated from the variation of the amplitude of the magnetic field with time.

In another embodiment of the invention, for the magnetic field, preferentially oscillating at high and medium frequency, sequences of increase, decrease, and constant magnetic field, taking place during a time $t_4+t_5+t_6$ are associated with a medium frequency cycle of medium frequency $f_m$ equal or proportional to $[2\pi/(t_4+t_5+t_6)]$, or $[1/(t_4+t_5+t_6)]$, preferentially when the frequency is estimated from the variation of the strength of the magnetic field with time, or of medium frequency $f_m$ equal or proportional to $[\pi/(t_4+t_5+t_6)]$, or $[½·(t_4+t_5+t_6)]$, preferentially when the frequency is estimated from the variation of the amplitude of the magnetic field with time.

In one embodiment of the invention, the time $t_1$, $t_2$, $t_3$, $t_4$, $t_5$, or $t_6$, is lower than 10, 1, $10^{-1}$, $10^{-2}$, $10^{-3}$, $10^{-4}$, $10^{-5}$, $10^{-6}$, $10^{-7}$, $10^{-8}$, $10^{-9}$, $10^{-10}$, $10^{-11}$, $10^{-11}$, $10^{-12}$, $10^{-12}$, $10^{-13}$, $10^{-14}$, or $10^{-15}$ seconds.

In another embodiment of the invention, the time $t_1$, $t_2$, $t_3$, $t_4$, $t_5$, or $t_6$, is larger than 10, 1, $10^{-1}$, $10^{-2}$, $10^{-3}$, $10^{-4}$, $10^{-5}$, $10^{-6}$, $10^{-7}$, $10^{-8}$, $10^{-9}$, $10^{-10}$, $10^{-11}$, $10^{-11}$, $10^{-12}$, $10^{-12}$, $10^{-13}$, $10^{-14}$, or $10^{-15}$ seconds.

In another embodiment of the inventions, the time $t_4$, $t_5$, or $t_6$, is 1.001, 1.01, 1.1, 1.2, 1.5, 2, 5, 10, 10, $10^3$, or $10^6$ larger than $t_1$, $t_2$, or $t_3$.

In one embodiment of the invention, for the oscillating magnetic field, preferentially oscillating at the high or high and medium frequency, the times $t_1$ and $t_1'$ or $t_4$ and $t_4'$ measured between 2 sequences of magnetic field increase, the times $t_2$ and $t_2'$ or $t_5$ and $t_5'$ measured between 2 sequences of magnetic field decrease, and the times $t_3$ and $t_3'$ or $t_6$ and $t_6'$ measured between 2 sequences of constant magnetic field, vary by more than 100, 75, 50, 25, 10, 5, 2, 1 $10^{-1}$, $10^{-2}$, $10^{-3}$, or $10^{-4}$%, where this percentage can correspond to $[(t_1-t_1')/t_1]$, $[(t_2-t_2')/t_2]$, $[(t_3-t_3')/t_3]$, $[(t_4-t_4')/t_4]$, $[(t_5-t_5')/t_5]$, or $[(t_6-t_6')/t_6]$, or by more than a factor of 1.5, 2, 5, 10, $10^2$, or $10^5$. In this case, the high or medium frequency is preferentially unstable.

In one embodiment of the invention, for the oscillating magnetic field, preferentially oscillating at the high or high and medium frequency, the times $t_1$ and $t_1'$ or $t_4$ and $t_4'$ measured between 2 sequences of magnetic field increase, the times $t_2$ and $t_2'$ or $t_5$ and $t_5'$ measured between 2 sequences of magnetic field decrease, and the times $t_3$ and $t_3'$ or $t_6$ and $t_6'$ measured between 2 sequences of constant magnetic field, vary by less than 100, 75, 50, 25, 10, 5, 2, 1, $10^{-1}$, $10^{-2}$, $10^{-3}$, or $10^{-4}$%, where this percentage can correspond to $[(t_1-t_1')/t_1]$, $[(t_2-t_2')/t_2]$, $[(t_3-t_3')/t_3]$, $[(t_4-t_4')/t_4]$, $[(t_5-t_5')/t_5]$, or $[(t_6-t_6')/t_6]$, or by less than a factor of 1.5, 2, 5, 10, $10^2$, or $10^5$. In this case, the high or medium frequency is preferentially stable.

In one embodiment of the invention, the oscillating magnetic field, preferentially oscillating at a high frequency, corresponds to that oscillating at a frequency $f_h$, which is preferentially larger than $10^{-10}$, $10^{-9}$, $10^{-8}$, $10^{-7}$, $10^{-6}$, $10^{-5}$, $10^{-4}$, $10^{-3}$, $10^{-2}$, $10^{-1}$, 1, 10, $10^2$, $10^3$, $10^4$, $10^5$, $10^6$, $10^7$, or $10^8$ kHz.

In another embodiment of the invention, the high frequency of oscillation is preferentially used to heat the magnetic nanoparticles, i.e. it is preferentially sufficiently high to heat nanoparticles. In some cases, the high frequency of oscillation is sufficiently high to induce a rapid movement of the magnetic nanoparticles and/or an inversion of the magnetic moment of the magnetic nanoparticles, i.e. a movement and/or magnetic moment inversion that preferentially takes place within less than 10, 1, $10^{-1}$, $10^{-2}$, $10^{-3}$, $10^{-4}$, $10^{-5}$, $10^{-6}$, $10^{-7}$, $10^{-8}$, or $10^{-9}$ seconds.

In still another embodiment of the invention, the high frequency of oscillation is used to heat the magnetic nanoparticles when the amplitude or strength of the magnetic field, or the maximum or average magnetic field, is/are sufficiently high to heat the nanoparticles, i.e. preferentially larger than $10^{-5}$, $10^{-4}$, $10^{-3}$, $10^{-2}$, $10^{-1}$, 1, 10, $10^2$, $10^3$, $10^4$, or $10^5$ T. In some case, the amplitude or strength of the magnetic field, or the maximum or average magnetic field, is sufficiently high to induce a movement of the magnetic nanoparticles and/or an inversion of the magnetic moment of the nanoparticle. In some case, the amplitude or strength of the magnetic field, or the maximum or average magnetic field, is larger than the coercivity of the magnetic nanoparticles, preferentially enabling inversion of the magnetic moment of the nanoparticle or the movement of the magnetic nanoparticle.

In still another embodiment of the invention, the high frequency of oscillation is too high, and/or the time $t_2$ is too short, to enable a decrease in temperature of the magnetic nanoparticles or of their surroundings, preferentially to yield a temperature decrease of more than 1, 5, 10, 50, or 100° C., preferentially when a suspension of magnetic nanoparticles, preferentially at a concentration of more than 0.1, 1, or 10 mg/mL is exposed to this magnetic field, preferentially when temperature is measured between at least 1, 10, 100, or 1000 high frequency oscillations or high frequency sequences. The fact that the high frequency of oscillation can't result in temperature decrease can be problematic in a magnetic hyperthermia treatment, since it can possibly lead to Eddy or Foucault currents or to other side effects due to continuous heating, possibly leading to overheating. This is the reason why it may appear necessary to add a low frequency of oscillation that produces cooling steps.

In one embodiment of the invention, cooling and heating steps are designated as cooling and heating phases. They can correspond to cooling and heating low frequency sequences.

In another embodiment of the invention, the oscillating magnetic field, preferentially oscillating at a medium frequency, corresponds to that oscillating at a medium frequency, $f_m$, which is preferentially 1.1, 1.5, 2, 5, 10, 20, 30, 50, $10^2$, $10^3$, $10^6$, or $10^9$ times lower than the high frequency, $f_h$. This medium frequency, $f_m$, can be an envelope function of the magnetic field oscillating at $f_h$ and can thus be used to yield a strength or amplitude of the magnetic field, a maximum or average magnetic field, which is larger than that reached without this medium frequency.

In one embodiment of the invention, the oscillating magnetic field, preferentially oscillating at a low, medium, and high frequency, corresponds to a magnetic field comprising at least one sequence, preferentially designated as a low frequency sequence, during which the magnetic field strength or amplitude, or the maximum or average magnetic field, estimated for the magnetic field oscillating only at high frequency or at high and medium frequency, is first constant at a value $A_7$ during a time $t_7$, preferentially if the magnetic field is stable, or increases up to a value $A_7$ during a time $t_7$, preferentially if the magnetic field is unstable, and at least another sequence, preferentially designated as another low frequency sequence, during which the magnetic field strength or amplitude, or maximum or average magnetic field, estimated for the magnetic field oscillating only at high frequency or at high and medium frequency, is constant at a value $A_8$ during a time $t_8$, preferentially if the magnetic field is stable, or decreases down to $A_8$ during a time $t_8$, preferentially if the magnetic field is unstable, where $A_8$ is lower than $A_7$. FIG. 2(b) represents a schematic diagram of the $A_7$ and $A_8$ low frequency sequences. These two sequences can preferentially be repeated more than 1, 2, 3, 4, 5, 10, $10^2$, $10^3$, $10^4$, $10^5$, $10^{10}$, $10^{25}$, $10^{50}$, or $10^{100}$ times.

In one embodiment of the invention, the oscillating magnetic field, preferentially oscillating at the low and high frequency, corresponds to a magnetic field comprising at least one sequence, preferentially designated as a low frequency sequence, during which the magnetic field strength or amplitude, or the maximum or average magnetic field, estimated for the magnetic field oscillating only at high frequency or at high and medium frequency, is first constant at a value $A_9$ during a time $t_9$, preferentially if the magnetic field is stable, or increases to a value $A_9$ during a time $t_9$, preferentially if the magnetic field is unstable, and at least another sequence, preferentially designated as another low frequency sequence, during which the magnetic field strength or amplitude, or maximum or average magnetic field, estimated for the magnetic field oscillating only at high frequency or at high and medium frequency, is constant at another value $A_{10}$ during a time $t_{10}$, preferentially if the magnetic field is stable, or decreases down to $A_{10}$ during $t_{10}$, preferentially if the magnetic field is unstable, where $A_{10}$ is lower than $A_9$. FIG. 2(c) represents a schematic diagram of the $A_9$ and $A_{10}$ low frequency sequences. These two sequences can preferentially be repeated more than 1, 2, 3, 4, 5, 10, $10^2$, $10^3$, $10^4$, $10^5$, $10^{10}$, $10^{25}$, $10^{50}$, or $10^{100}$ times.

In an embodiment of the invention, sequence during which the magnetic field strength or amplitude, or the maximum or average magnetic field, estimated for the magnetic field oscillating only at high frequency or at high and medium frequency, is constant at a value $A_7$ or $A_9$ during a time $t_7$ or $t_9$, or increases to $A_7$ or $A_9$ during $t_7$ or $t_9$, is called a $A_7$ or $A_9$ low frequency sequence. It may correspond to a heating step.

In one embodiment of the invention, the time $t_7$ or $t_9$ is sufficiently long, preferentially longer than $10^{-9}$, $10^{-8}$, $10^{-7}$, $10^{-6}$, $10^{-5}$, $10^{-4}$, $10^{-3}$, $10^{-2}$, $10^{-1}$, 1, 10, $10^2$, or $10^3$ seconds, to enable the production and/or dissipation of heat by the magnetic nanoparticle, and preferentially of its surrounding, under the application of an alternating field, hence leading to a heating step.

In another embodiment of the invention, the surrounding of the magnetic nanoparticles is defined as the region surrounding or comprising them, i.e. preferentially a region comprising more than 1, 10, $10^2$, $10^3$, $10^4$, $10^5$, $10^{10}$, or $10^{20}$ nanoparticles, or the volume of the region comprising them, where this volume is preferentially estimated from the center of 1, 10, $10^2$, $10^3$, $10^4$, $10^5$, $10^{10}$, or $10^{20}$ nanoparticles, as being preferentially smaller than 1 m$^3$, 1 cm$^3$, 1 mm$^3$, or 1 µm$^3$.

In still another embodiment of the invention, the time $t_7$ or $t_9$ is sufficiently short, preferentially shorter than $10^{-9}$, $10^{-8}$, $10^{-7}$, $10^{-6}$, $10^{-5}$, $10^4$, $10^{-3}$, $10^{-2}$, $10^{-1}$, 1, 10, $10^2$, or $10^3$ seconds, preferentially to prevent a situation of overheating.

In another embodiment of the invention, sequence during which the magnetic field strength or amplitude, or maximum or average magnetic field, estimated for the magnetic field oscillating only at high frequency or at high and medium frequency, is constant at a value $A_8$ or $A_{10}$ during the time $t_8$ or $t_{10}$, or increases to $A_8$ or $A_{10}$ during $t_8$ or $t_{10}$, is called a $A_8$ or $A_{10}$ low frequency sequence. It may correspond to a cooling step.

In one embodiment of the invention, the time $t_8$ or $t_{10}$ is sufficiently long, preferentially longer than $10^{-9}$, $10^{-8}$, $10^{-7}$, $10^{-6}$, $10^{-5}$, $10^{-4}$, $10^{-3}$, $10^{-2}$, $10^{-1}$, 1, 10, $10^2$, or $10^3$ seconds, to cool down the magnetic nanoparticle, and preferentially also its surrounding.

In still another embodiment of the invention, the times $t_8$ or $t_{10}$ are sufficiently short, preferentially shorter than $10^{-9}$, $10^{-8}$, $10^{-7}$, $10^{-6}$, $10^{-5}$, $10^{-4}$, $10^{-3}$, $10^{-2}$, $10^{-1}$, 1, 10, $10^2$, or $10^3$ seconds.

In one embodiment of the invention, the magnetic field strength or amplitude, or the maximum or average magnetic field can be considered constant during $t_7$, $t_8$, $t_9$, and/or $t_{10}$ when they do not vary by more than 1, 2, 5, 10, 15, 25, 50, 75, 80 or 100%, where this percentage of variation may correspond to $[(\varepsilon_{max}-\varepsilon_{min})/\varepsilon_{max}]$, where $\varepsilon_{max}$ and $\varepsilon_{min}$ can be the maximum and minimum values measured during $t_7$, $t_8$, $t_9$, and/or $t_{10}$ of the magnetic field strength or amplitude, or of maximum or average magnetic field, estimated for the magnetic field oscillating only at high frequency or at high and medium frequency.

In one embodiment of the invention, a $A_8$ or $A_{10}$ low frequency sequence preferentially follows a $A_7$ or $A_9$ low frequency sequence, or a $A_7$ or $A_9$ low frequency sequence follows a $A_8$ or $A_{10}$ low frequency sequence, but it can happen that several $A_8$ or $A_{10}$ low frequency sequences follow each other or that several $A_7$ or $A_9$ low frequency sequences follow each other.

In still another embodiment of the invention, $A_7$ or $A_9$ is non-zero or much larger than the amplitude of the earth's magnetic field. $A_7$ or $A_9$ is preferentially lower than the magnetic field amplitude enabling to generate Eddy or Foucault currents. $A_7$ or $A_9$ is also preferentially larger than the amplitude of the magnetic field, which is necessary to heat magnetic nanoparticles, preferentially by magnetic hyperthermia, or larger than 0.01 mT, or 0.1 mT, or 1 mT, or 2 mT, or 3 mT, or 5 mT, or 7 mT, or 10 mT, or 15 mT, or 20 mT, or 25 mT, or 50 mT, or 100 mT, or 500 mT, or 1 T, or 10 T, or 100 T, or $10^3$ T.

In an embodiment of the invention, $A_7$ or $A_9$ is larger than $10^{-6}$, $10^{-4}$, $10^{-2}$, 1, 10, $10^2$, or $10^3$ Watt per cm$^3$ of the body part.

In an embodiment of the invention, $A_7$ or $A_9$ is at least 1.1, 1.5, 2.5, 10, 25, 50, 100, 250, 500, $10^3$, $10^5$, $10^{10}$, or $10^{50}$ times larger than $A_8$ or $A_{10}$.

In another embodiment of the invention, $A_8$ or $A_{10}$ is zero, corresponding to a zero magnetic field, when the magnetic field strength or amplitude, or maximum and average magnetic fields, preferentially estimated at high or at high and medium frequency, are close to the amplitude of the earth's magnetic field or lower than the amplitude of a magnetic field, which generates Eddy or Foucault currents or less than a value of magnetic field amplitude, which enables to heat magnetic nanoparticles, preferentially by magnetic hyperthermia, or lower than $10^3$ T, or 100 T, or 10 T, or 1 T, or 500 mT, or 100 mT, or 50 mT, or 25 mT, or 10 mT, or 5 mT, 1, $10^{-1}$, $10^{-3}$, or $10^{-6}$ mT.

In another embodiment of the invention, $A_8$ or $A_{10}$ is lower than $10^{-6}$, $10^{-4}$, $10^{-2}$, 1, 10, $10^2$, or $10^3$ Watt per cm$^3$ of the body part.

In one embodiment of the invention, the times $t_7$ and $t_7'$, $t_8$ and $t_8'$, $t_9$ and $t_9'$, $t_{10}$ and $t_{10}'$, measured between two $A_7$, $A_8$, $A_9$, or $A_{10}$ low frequency sequences, respectively, vary by more or less than 100, 75, 50, 25, 10, 5, 2, 1 $10^{-1}$, $10^{-2}$, $10^{-3}$, or $10^{-4}$%, where this percentage can correspond to $[(t_7-t_7')/t_7]$, $[(t_8-t_8')/t_8]$, $[(t_9-t_9')/t_9]$, or $[(t_{10}-t_{10}')/t_{10}]$, or vary by a factor of more or less than 1.1, 2, 5, 10, $10^2$, $10^3$, or $10^5$.

In one embodiment of the invention, a combination of a $A_7$ low frequency sequence with a $A_8$ low frequency sequence or of a $A_9$ low frequency sequence with a $A_{10}$ low frequency sequence corresponds to a low frequency cycle.

In another embodiment of the invention, a low frequency cycle, taking place during a time $t_7+t_8$ or $t_9+t_{10}$, is associated with a low frequency cycle of low frequency $f_l$ equal or proportional to $[2\pi/(t_7+t_8)]$, $[1/(t_7+t_8)]$, $[2\pi/(t_9+t_{10})]$, or $[1/(t_9+t_{10})]$.

In one embodiment of the invention, a low frequency sequence or a low frequency cycle is repeated more than 2, 3, 4, 5, 10, $10^2$, $10^3$, $10^4$, $10^5$, $10^{10}$, $10^{25}$, $10^{50}$, or $10^{100}$ times.

In another embodiment of the invention, a magnetic field oscillating at a low frequency corresponds to a magnetic field oscillating at a frequency $f_l$, which is preferably between $10^{-6}$ Hz and $10^6$ Hz. This low oscillation frequency may produce multiple successive heating and cooling steps. This low frequency may be chosen to yield maximum treatment efficacy and minimum treatment toxicity, especially during a magnetic hyperthermia treatment.

In still another embodiment of the invention, $f_l$ is smaller than $10^6$, $10^5$, $10^4$, $10^3$, $10^2$, 10, 1, $10^{-1}$, $10^{-2}$, $10^{-3}$, $10^{-4}$, $10^{-5}$, or $10^{-6}$ Hz. In some cases, $f_l$ can also be between 0.2 $10^{-2}$ Hz and 0.3 $10^{-1}$ Hz, or between 0.02 $10^{-2}$ Hz and 3 $10^{-1}$ Hz, or between 0.002 $10^{-2}$ Hz and 30 $10^{-1}$ Hz. In some cases, $f_l$ can also be more than 1.01, 1.1, 1.5, 2, 5, 10, $10^2$, $10^3$, $10^5$, $10^8$, $10^{11}$, or $10^{20}$ times lower than $f_m$ or $f_h$. In some other cases, $f_l$ can also be less than 1.01, 1.1, 1.5, 2, 5, 10, $10^2$, $10^3$, $10^5$, $10^8$, $10^{11}$, or $10^{20}$ times lower than $f_m$ or $f_h$.

In still another embodiment of the invention, $f_l$ is larger than $10^6$, $10^5$, $10^4$, $10^3$, $10^2$, 10, 1, 10-1, $10^{-2}$, $10^{-3}$, $10^{-4}$, $10^{-5}$, or $10^{-6}$ Hz.

In one embodiment of the invention, a heating step combined with a cooling step corresponds to a low frequency cycle.

In another embodiment of the invention, maximal temperatures, $T_{max}$, and minimal temperatures, $T_{min}$, are defined as the maximal temperatures reached during the heating steps or low frequency sequences $A_7$ or $A_9$, and minimal temperatures reached during the cooling steps or low frequency sequences $A_8$ or $A_{10}$.

In another embodiment of the invention, $T_{max}$ and/or $T_{min}$ varies or vary between two low frequency cycles by more or less than 1, 5, 10, 15, 20, 50, 75, 80, or 90%, where this percentage can correspond to $[2(T_{max}-T_{min})/(T_{max}+T_{min})]$.

In another embodiment of the invention, the oscillating magnetic field is applied during a session, preferentially a heating session. The duration of a heating session is designated by $t_{11}$ while the time separating two different heating sessions is designated by $t_{12}$.

According to the invention, a session can be repeated more than 2, 5, or 10 times, preferentially with a very low frequency $f_{vl}$, which can be measured using the formula: $f_{vl}=1/[2\pi(t_{11}+t_{12})]$ or $f_{vl}=1/(t_{11}+t_{12})$. $f_{vl}$ is preferentially lower than 1, $10^{-3}$, $10^{-6}$, or $10^{-9}$ Hz, or 2, 5, 10, $10^3$, $10^9$, or $10^{20}$ times lower than $f_l$, $f_m$, or $f_h$.

In another embodiment of the invention, a session is associated with the time during which an alternating magnetic field is applied, most preferentially a time during which a typical magnetic hyperthermia treatment takes place, i.e. typically more or less than $10^{-9}$, $10^{-6}$, $10^{-3}$, 1, $10^3$, $10^6$, or $10^9$ minutes.

In one embodiment, a heating step or a heating session corresponds to a lapse of time during which a temperature increase occurs.

According to the invention, the temperature increase can in some cases either be measurable, preferentially using a standard thermometry method, or not be measurable in some other cases, preferentially using a standard thermometry method. It can have the same meaning as hyperthermia or magnetic hyperthermia.

The standard thermometry method, according to the invention, can be a method that enables temperature measurement at a larger scale than the cellular or nanometer scale. It may measure the temperature macroscopically within a tissue, an organ, or a tumor for example but may preferentially not measure the temperature around nanoparticles, or inside or just around cells.

In one embodiment of the invention, the temperatures reached during treatment, may include temperature gradients, a temperature that one wants to achieve, a given temperature, a temperature probe, a constant temperature, a temperature decrease, a temperature increase, a temperature variation, a temperature of the magnetic nanoparticles, a maximal or maximum temperature, a minimal or minimum temperature, a measure of temperature macroscopically, or a temperature around nanoparticles. These temperatures can indicate a physico-chemical disturbance reached during treatment, physico-chemical disturbance gradients, a physico-chemical disturbance that one wants to achieve, a given physico-chemical disturbance, a physico-chemical disturbance probe, a constant physico-chemical disturbance, a physico-chemical disturbance decrease, a physico-chemical disturbance increase, a physico-chemical disturbance variation, a physico-chemical disturbance of the magnetic nanoparticles, a maximal or maximum physico-chemical disturbance, a minimal or minimum physico-chemical disturbance, a measure of physico-chemical disturbance macroscopically, or a physico-chemical disturbance around nanoparticles, respectively.

In another embodiment of the invention, heating, continuous heating, overheating, heating steps, heating phases, heating low frequency sequences, heating session, heating the nanoparticles, heating times, or heating gradients, can indicate an increase in physico-chemical disturbance, a continuous increase in physico-chemical disturbance, too large of an increase in physico-chemical disturbance, steps of a physico-chemical disturbance increase, phases of a physico-chemical disturbance increase, low frequency sequences of a physico-chemical disturbance increase, a session of a physico-chemical disturbance increase, application of an increased physico-chemical disturbance to nanoparticles, times of a physico-chemical disturbance increase, or gradients of a physico-chemical disturbance increase, respectively.

In another embodiment of the invention, cooling, continuous cooling, cooling steps, cooling phases, cooling low frequency sequences, a cooling session, cooling the nanoparticles, cooling times, or cooling gradients, can indicate a decrease in physico-chemical disturbance, a continuous decrease in physico-chemical disturbance, too large of a decrease in physico-chemical disturbance, steps of a physico-chemical disturbance decrease, phases of a physico-chemical disturbance decrease, low frequency sequences of a physico-chemical disturbance decrease, a session of a physico-chemical disturbance decrease, application of a decreasing physico-chemical disturbance to nanoparticles, times of a physico-chemical disturbance decrease, or gradients of a physico-chemical disturbance decrease, respectively.

In another embodiment of this invention, the physico-chemical disturbance can be associated with more than one of the following physico-chemical disturbance parameters: (i), the application of the magnetic field oscillating at high frequency and, at medium and/or low frequency, (ii), the movement of the nanoparticles, by more or less than 1 nm, 10 nm, 100 nm, 1 μm, 10 μm, 100 μm, 1 mm, 10 mm, 1 cm, 10 cm or 1 m, (iii), the release or dissociation of a substance or compound from the nanoparticle, (iv), a change in the composition of the nanoparticle, (v), a variation in the pH of the nanoparticle by more or less than 14, 13, 12, 11, 10, 9, 8, 7, 6, 5, 4, 3, 2, or 1 pH unit(s), (vi), a variation in redox potential of the nanoparticle by more or less than 1 V, 100, 10, 1, or 0.1 mV, or (vii), a variation in the surrounding of the nanoparticle such as a variation in pH, temperature, redox potential, or chemical composition of this surrounding.

In another embodiment of the invention, the increase in physico-chemical disturbance is associated with the increase by more than 1, 5, 10, 25, 50, 75, or 90% or by a factor of more than 1.2, 2, 5, 10, or $10^2$ of the physico-chemical disturbance parameter.

In another embodiment of the invention, the decrease in physico-chemical disturbance is associated with the decrease by more than 1, 5, 10, 25, 50, 75, or 90% or by a factor of more than 1.2, 2, 5, 10, or $10^2$ of the physico-chemical disturbance parameter.

The invention also relates to magnetic nanoparticles for use, in which the low frequency of oscillation includes at least one cycle comprising a step with increasing physico-chemical disturbance and a step with decreasing physico-chemical disturbance.

In still another embodiment of the invention, $t_{11}$ is larger than $10^{-9}$, $10^{-6}$, $10^{-3}$, 1, $10^2$, $10^3$, $10^4$, $10^5$, $10^6$, $10^9$, or $10^{20}$ seconds. It can be comprised between 1 and 30 minutes, 1 and 12 hours, or 1 and 15 days. The value of $t_{11}$ can correspond to the time during which the individual can be treated, preferentially without any side effects. It is preferentially lower than the time of anesthesia of the individual. It preferentially corresponds to the time during which the medical team in charge of the treatment of the individual is available or to the time during which the alternating magnetic field or radiation can be applied.

In still another embodiment of the invention, $t_{11}$ smaller than $10^{-9}$, $10^{-6}$, $10^{-3}$, 1, $10^2$, $10^3$, $10^4$, $10^5$, $10^6$, $10^9$, or $10^{20}$ seconds.

In still another embodiment of the invention, $t_{11}$ is 1, 1.0001, 1.001, 1.01, 1.1, 1.2, 1.5, 2, 5, 10, $10^2$, $10^3$, or $10^5$ larger than $t_7$, $t_8$, $t_9$, $t_{10}$, $t_7+t_8$, or $t_9+t_{10}$.

In still another embodiment of the invention, the time separating two sessions corresponds to the time necessary for the individual or patient or medical team to rest between two treatments, or the time necessary to switch off the device generating the magnetic field.

In still another embodiment of the invention, $t_{12}$ is larger than $10^{-9}$, $10^{-6}$, $10^{-3}$, 1, $10^2$, $10^3$, $10^4$, $10^5$, $10^6$, $10^9$, or $10^{20}$ seconds.

In still another embodiment of the invention, $t_{12}$ is lower than $10^{-9}$, $10^{-6}$, $10^{-3}$, 1, $10^2$, $10^3$, $10^4$, $10^5$, $10^6$, $10^9$, or $10^{20}$ seconds.

In still another embodiment of the invention, $t_{12}$ is 1, 1.0001, 1.001, 1.01, 1.1, 1.2, 1.5, 2, 5, 10, $10^2$, $10^3$, or $10^5$ larger than $t_7$, $t_8$, $t_9$, $t_{10}$, $t_7+t_8$, $t_9+t_{10}$, or $t_{11}$.

In another embodiment of the invention, the application of the magnetic field, preferentially oscillating at the high and, medium and/or low frequency, corresponds to the production of a magnetic field applied by a source of energy, most preferentially a source of energy manufactured or controlled by the individual. It can correspond to the application of a magnetic field that can heat magnetic nanoparticles, where heat can preferentially be measured with a thermometry method, preferentially a standard thermometry method, using for example an infrared camera or a thermocouple.

In another embodiment of the invention, the non-application of the magnetic field, preferentially oscillating at the high, medium and/or low frequency, also designated as zero magnetic field, corresponds to the application of a magnetic field whose strength or amplitude is very weak, such as the application of the earth magnetic field or of the magnetic field generated by instruments working with currents or magnets, whose purpose is not to heat nanoparticles but that create a non-negligible magnetic field. In some cases, the non-application of the oscillating magnetic field can also take place during the application of a magnetic field whose amplitude can be less than the amplitude necessary to heat magnetic nanoparticles. In some cases, the non-application of the oscillating magnetic can correspond to the application of a magnetic field outside of the region where magnetic nanoparticles are located, or outside of the body part of the individual.

In another embodiment of the invention, the magnetic field, preferentially oscillating at the high and, medium and/or low frequency, is applied in the region comprising magnetic nanoparticles. This region may preferentially comprise more than 1, 10, $10^2$, $10^3$, $10^6$, $10^{12}$, $10^{20}$, $10^{50}$, or $10^{100}$ magnetic nanoparticles, or more than 1, 5, 10, 25, 50, 75, 90, or 95% of the administered nanoparticles, where this percentage can correspond to the number of nanoparticles in the region where magnetic nanoparticles are administered divided by the total number of administered nanoparticles. This region may also preferentially comprise more than 1, 5, 10, 25, 50, 75, 90, or 95% of the nanoparticles exposed to the oscillating magnetic field, where this percentage can correspond to the number of nanoparticles exposed to the oscillating magnetic field divided by the total number of nanoparticles, preferentially comprised in the body part of the individual.

In another embodiment of the invention, the oscillation of the magnetic field, preferentially at the high and, medium and/or low frequency, comprises the variation, decrease, or increase with time of the magnetic field strength or amplitude, or of the maximum or average magnetic field, or comprises a constant magnetic field strength or amplitude, maximum or average magnetic field with time, or comprises a combination of varied, decreasing, increasing, or constant magnetic field with time.

In still another embodiment of the invention, the oscillation of the magnetic field comprises the variation, decrease, or increase with time of the energy or power of the oscillating magnetic field, or comprises a constant energy or power of the oscillating magnetic field with time, or comprises a combination of varied, decreasing, increasing, or constant energy or power of the oscillating magnetic field with time.

In another embodiment of the invention, the oscillation of the magnetic field with time is represented, or modeled, by a function such as a numerical function, a zero, identity, square, cube, inverse, constant, linear, second degree, power, holographic, laurentian, cubic root, affine, polynomial, rational, absolute value, sign Heaviside, count of prime numbers, integer part, fractional part, sinus, cosine, tangent, cotangent, arc sinus, arc cosine, tangent arc, Dirichlet, exponential, logarithmic, hyperbolic, sigmoid, Brillouin, Langevin, gamma, beta, integral, logarithm, integral, Bessel, harmonic and associated, or arithmetic function, or a derivative, or a combination of one or several of these functions.

In another embodiment of the invention, such function is determined by first measuring the oscillation of the magnetic field with time, by using a probe, and then by adjusting this measurement with this function, preferably using suitable computer software, such as "origin".

In still another embodiment of the invention, the frequency of oscillation, f, and associated period, T, where T=1/f, vary with parameters such as time, current intensity, distance between the device generating the magnetic field and the magnetic nanoparticle, distance between the device generating the magnetic field and the body part of the individual, or the parameter of the device, it is possible to determine a relation between the variation of the oscillation frequency, Δf, or between the variation of its associated period, ΔT, and the variation of parameters, such as variations of the time of application of the oscillating magnetic field, of current intensity, of power, of distance between the device generating the magnetic field and the magnetic nanoparticle, or of the parameter of the device. In some cases, such relation can be represented or modeled by one or several of these functions.

In another embodiment of the invention, the oscillation of the magnetic field with time, produces a symmetrical oscillation of the magnetic field, i.e. the function describing such oscillation is a symmetric function, in which the symmetry can preferentially be observed from at least one time point of the variation.

In another embodiment of the invention, the oscillation of the magnetic field with time is symmetrical, preferentially when the ratio $[t_i/t_j]$, is lower than $10^{-6}$, $10^{-3}$, $10^{-1}$, 1, 10, $10^3$, or $10^6$, where $t_i \neq t_j$ and i and j are preferentially numbers between 1 and 10 and $t_1$ to $t_{10}$ have previously been defined.

In another embodiment of the invention, the oscillation of the magnetic field with time is asymmetric, i.e. the function describing such oscillation is an asymmetric function, where the asymmetry can be observed from at least one time point of the oscillation.

In another embodiment of the invention, the oscillation of the magnetic field with time is asymmetric when the ratio $[t_i/t_j]$ is larger than $10^{-6}$, $10^{-3}$, $10^{-1}$, 1, 10, $10^3$, or $10^6$, or $[t_i/t_j]$ is lower than $10^{-6}$, $10^{-3}$, $10^{-1}$, 1, 10, $10^3$, or $10^6$, where $t_i \neq t_j$ and i and j are numbers, preferentially between 1 and 10.

In one embodiment of the invention, magnetic hyperthermia is a method or a method of treatment, preferably used to treat the body part of the individual, or pathological cells, such as prokaryotic or eukaryotic cells, most preferentially tumors. In this method, magnetic materials, such as magnetic nanoparticles, are preferentially introduced in the body part of the individual or sent to body part of the individual and exposed to an oscillating magnetic field, preferentially producing a temperature increase of the nanoparticles and preferentially also of the nanoparticle surrounding. The treatment can result from the change of any parameter that results from the application of the oscillating magnetic field on the magnetic nanoparticles brought into contact, mixed, or assembled with the cells, entity, or body part of the individual.

In one embodiment of the invention, magnetic hyperthermia is a diagnosis method, preferably used to detect a specific condition, such as an illness, of the individual, or specific cells, such as prokaryotic or eukaryotic cells, pathological cells, such as tumor cells, or an entity or materials that originate from such cells or individual. In this method, magnetic materials, such as magnetic nanoparticles, are preferentially brought into contact or mixed or assembled with cells, the entity, body part of the individual and exposed to the oscillating magnetic field, preferentially producing a temperature increase of the nanoparticles and preferentially also of the nanoparticle surrounding. The diagnosis can be based on the detection of temperature or on the change of any parameter that results from the application of the oscillating magnetic field on the magnetic nanoparticles brought into contact, mixed, or assembled with the cells, entity, or body part of the individual.

In one embodiment of the invention, the body part of the individual designates any part of a living or dead individual or organism, where such individual or organism preferentially contains more than one prokaryotic or eukaryotic cell. Such individual or organism can be a unicellular or multicellular organism, a plant, a human, an animal, a bacterium, an archaea, or a fungus. It can be a tissue, an organ, blood, skin, an arterial, bone, DNA, RNA, a protein, a lipid, an enzyme, one or an assembly of amino acids or nucleic acids, or biological material.

It can represent one or several part(s) of the individual or organism or a whole individual or organism. The body part of the individual preferentially represents the part, which is treated.

It can also designate the whole individual or any biological material, preferentially originating or extracted from a living organism or from the individual.

In one embodiment of the invention, body part of the individual belongs to the respiratory system, the digestive, respiratory, nervous, muscular, or skeletal system. They may also belong to a tumor, infected tissue or infected assembly of cells, possibly containing bacteria or viruses, which may belong to at least one of these systems.

In one embodiment, body part of the individual contains more than 1, 10, $10^3$, $10^6$, $10^9$, or $10^{13}$ magnetic nanoparticles. In some cases, body part of the individual can be associated with the magnetic nanoparticles, for example when the nanoparticles are opsonized.

In another embodiment of the invention, a magnetic hyperthermia therapeutic treatment method is a method in which magnetic nanoparticles are exposed to a magnetic field, preferentially oscillating at the high and, medium and/or low frequency. In this method, the exposure of magnetic nanoparticles to the oscillating magnetic field preferentially induces a temperature increase and/or a movement of the nanoparticles, which preferentially lead(s) to a specific interaction and/or transformation of body part of the individual. Such specific interaction and/or transformation can be the internalization or externalization of nanoparticles in/from cells, the death of cells, preferentially by apoptosis or necrosis, where these cells preferentially belong to body part of the individual.

The present invention concerns magnetic nanoparticles for use in a magnetic hyperthermia diagnosis method, wherein the magnetic nanoparticles are exposed to a magnetic field oscillating at the high frequency and at the medium and/or low frequency.

In another embodiment of the invention, a magnetic hyperthermia diagnosis method is a method of diagnostic, preferentially used to detect an illness, or a condition, most preferentially by detection of a substance of interest, which can be comprised in the body part of the individual. It can be a method of detection in which: i), the substance of interest is initially bound to the magnetic nanoparticles and then detaches from them under application of the oscillating magnetic field or ii), the substance of interest is initially detached from the nanoparticles and then binds to them under application of the oscillating magnetic field, or iii), the type of interaction between the substance of interest and the magnetic nanoparticles changes under application of the oscillating magnetic field. Such change may then be used to detect the substance of interest.

The present invention concerns magnetic nanoparticles for use in a magnetic hyperthermia cosmetic method, wherein the magnetic nanoparticles are exposed to a magnetic field oscillating at the high frequency and, at the medium frequency and/or at the low frequency.

In another embodiment of the invention, a magnetic hyperthermia cosmetic method is a cosmetic method, preferentially a method used to make the body part of the individual, such as the skin, hair, or face, more appealing, more beautiful, to cover or hide a defect or deficiency of the body part of the individual, to improve the appearance of defect or irregularity of the body part of the individual. It can be a cosmetic method in which magnetic nanoparticles exposed to the oscillating magnetic field change the color, the appearance, the cell distribution, the tension, of the body part of the individual.

The present invention concerns magnetic nanoparticles for use in a magnetic hyperthermia vaccination or prophylactic method, wherein the magnetic nanoparticles are exposed to a magnetic field oscillating at the high frequency and at the medium and/or low frequency.

In still another embodiment of the invention, a magnetic hyperthermia prophylactic or vaccination method is a method that stimulates the immune system to fight against an illness such as a tumor, where the stimulation of the immune system can preferentially be repeated by applying the oscillating magnetic field more than once, most preferentially by applying this field in the presence of the magnetic nanoparticle in the body part of the individual. The vaccination or prophylactic method can be undertaken before or after the illness has occurred and be repeated, started by the administration of the magnetic nanoparticle, preferentially in the body part of the individual, be activated by the application of the oscillating magnetic field, preferentially be re-activated by re-applying the oscillating magnetic field, most preferentially without re-administering the nanoparticles. In some cases, this vaccination or prophylactic method enables to boost the activity of the immune system by applying the oscillating magnetic field and should preferentially be more efficient than a standard vaccination or prophylactic method, for which a control over the activity of the immune system can hardly be achieved.

In one embodiment of the invention, the nanoparticles are administered directly into the body part of the individual, for example by intra-tumor injection.

In another embodiment of the invention, the nanoparticles are administered indirectly in the body part of the individual, for example by intravenous injection, or at a distance from the body part of the individual, which is larger than 1 cm, 10 cm, 100 cm, 1 m, or 2 m.

In one embodiment of the invention, the concentration of magnetic nanoparticle is sufficient in the body part of the individual to enable a temperature increase therein, i.e. this concentration is larger than 1 ng, 10 ng, 100 ng, 1 µg, 10 µg, 100 µg, 1 mg, 10 mg, 100 mg, 1 g, 10 g, 100 g, or 1 kg per mm³ of the body part of the individual.

In one embodiment of the invention, the magnetic nanoparticles occupy a high enough percentage of the body part of the individual to induce a temperature increase in such part, i.e. this percentage is higher or larger than $10^{-10}$, $10^{-9}$, $10^{-8}$, $10^{-7}$, $10^{-6}$, $10^{-5}$, $10^{-4}$, $10^{-3}$, $10^{-2}$, $10^{-1}$, 1, 10, 15, 25, 50, or 75% in such part, where this percentage may represent the volume occupied by the nanoparticles in such part divided by the total volume of such part.

The invention also concerns magnetic nanoparticles, wherein the magnetic nanoparticles have a SAR higher or larger than 1 W/$g_{Fe}$, or than 0.001, 0.1, 1, 10, 50, 100, 500, 750, 1000, 2000, or 5000 Watt per gram of nanoparticles (W/g), preferentially Watt per gram of iron comprised in nanoparticles (W/$g_{Fe}$).

In another embodiment of the invention, the magnetic nanoparticles possess a SAR, which is sufficient to induce a temperature increase, i.e. a SAR, which is larger than 0.001, 0.1, 1, 10, 50, 100, 500, 750, 1000, 2000, or 5000 Watt per gram of nanoparticles (W/g), preferentially Watt per gram of iron comprised in nanoparticles (W/$g_{Fe}$).

In still another embodiment of the invention, the oscillating magnetic field is sufficiently powerful to induce a temperature increase, i.e. it has a power of more than $10^{-10}$, $10^{-5}$, $10^{-2}$, $10^{-1}$, 1, 10, $10^2$, or $10^3$ Watt per $cm^3$ of exposed body part.

In still another embodiment of the invention, the SAR is measured in at least one of the following conditions: (i), at a nanoparticle concentration that is sufficiently high so that the SAR does not vary as a function of nanoparticle concentration, or at a concentration that is larger than 0.01, 0.1, 1, 2, 5, 10, 20, 30, 40, or 50 mg/ml, (ii), in a liquid medium such as water or in a solid medium or in a semi solid medium such as a gel, (iii), by applying an oscillating magnetic field with an amplitude or maximum or average magnetic field larger than 5, 10, 15, 20, 25, 30, 35, 40, 45, 50, 75, or 100 mT, (iv), by applying an oscillating magnetic field with a frequency or high frequency higher or larger than 1, 2, 5, 10, 25, 50, 100, 200, 500, or 1000 kHz, (v), in a volume that is smaller than 1000, 500, 250, 100, 50, 20, 10, 5, 2, or 1 µl, (vi), in a volume that is larger than 1000, 500, 250, 100, 50, 20, 10, 5, 2, or 1 µl, or (vii), in adiabatic conditions, preferentially in conditions where heat losses are lower than 10, 5, 2, 1, 0.1, or 0.01° C. in the container or tube comprising the nanoparticles and used for SAR measurement.

In one embodiment of the invention, the magnetic nanoparticle is characterized by at least one of the following properties: i), a composition comprising at least one transition metal, preferentially an oxide of a transition metal, most preferentially iron oxide, most preferentially maghemite or magnetite, or an intermediate composition between maghemite and magnetite, where this composition may preferentially be that of the magnetic core of magnetic nanoparticles, ii), the presence of a coating that surrounds the magnetic core of the nanoparticles and prevents nanoparticle aggregation, preferentially enabling nanoparticle administration in an organism or stabilizing the nanoparticle magnetic core, where coating thickness may preferably lie between 0.1 nm and 10 µm, 0.1 nm and 1 µm, 0.1 nm and 100 nm, 0.1 nm and 10 nm, or between 1 nm and 5 nm, iii), a diamagnetic, paramagnetic, superparamagnetic, ferromagnetic, or ferrimagnetic behavior, where this behavior is preferably measured or observed at a temperature larger than 1 K, 10 K, 20 K, 50 K, 100 K, 200 K, 300 K, or 350 K, iv), a coercivity larger than 0.01, 0.1, 1, 10, or 100 Oe, a ratio between remanent and saturation magnetization larger than 0.01, 0.1, 0.2, 0.3, 0.4, 0.5, or 0.75, or a saturation magnetization larger than 0.1, 1, 5, 10, or 50 emu/g, where these properties are preferably measured or observed at a temperature larger than 1 K, 10 K, 20 K, 50 K, 100 K, 200 K, 300 K, or 350 K, v), a crystallinity, i.e. nanoparticles have at least 2, 5, 10, or 100 crystalline planes, preferentially observable by electron microscopy, vi), the presence of a single domain, vii), a size that is are larger than 0.1, 0.5, 1.5, 10, 15, 20, 25, 30, 50, 60, 70, 80, 100, 120, 150, or 200 nm, viii), a size that is smaller than 0.1, 0.5, 1.5, 10, 15, 20, 25, 30, 50, 60, 70, 80, 100, 120, 150, or 200 nm, ix), a size between 0.1 nm and 10 µm, 0.1 nm and 1 µm, 0.1 nm and 100 nm, 1 nm and 100 nm, or between 5 nm and 80 nm, x), a nonpyrogenicity, i.e. nanoparticles possess an endotoxin concentration lower than 10000, 1000, 100, 50, 10, 5, 2, or 1 EU (endotoxin unit) per mg of nanoparticle or per mg of iron comprised in nanoparticles, xi), a synthesis method that is chemical, i.e. without the involvement of a living synthetizing organism, xii), a synthesis by a synthetizing living organism, preferentially by magnetotactic bacteria, leading to the production of magnetosomes, preferentially extracted from magnetotactic bacteria, preferentially only or mostly comprising the mineral magnetic core of the magnetosomes, xiii), the presence of less than 50, 25, 15, 10, 5, 2, or 1% of organic or carbon material originating from the synthetizing living organism, xiv), the presence of more than 99, 95, 80, 70, 60, 50, or 25% of mineral magnetic material originating from the synthetizing living organism.

In one embodiment of the invention, the SAR of the magnetic nanoparticle possessing one of the above property is 1.1, 1.2, 1.5, 2, 5, 10, 15, 20, 50, or 100 larger than the SAR of the magnetic nanoparticle without this property, or is larger than 10, 20, 50, 100, 1000 W/$g_{Fe}$, where the SAR is preferentially measured at high nanoparticle concentration, or at a concentration larger than 1, 10, or 100 mg/mL.

In one embodiment of the invention, the magnetic nanoparticle possessing one of the above property has a SAR, which increases, preferentially by a factor of 1.001, 1.01, 1.1, 1.2, 1.5, 2, 5, 10, 100, or 1000, with increasing ratio between maximum and average magnetic field, preferentially by a factor of 1.001, 1.01, 1.1, 1.2, 1.5, 2, 5, 10, 100, or 1000. In some cases, the SAR of the magnetic nanoparticle with one of the above property increases more than a magnetic nanoparticle without such property.

In another embodiment of the invention, a high ratio between maximum and average magnetic field, preferentially larger than 1.001, 1.01, 1.1, 1.2, 1.5, 2, 3, 4, 5, 10, 25, 50, 100, or 1000, corresponds to the application of an oscillating magnetic field with a high amplitude, preferentially larger than 0.1, 1, 2, 5, 10, 15, 25, 50, 100, 250, or 500 mT, applied during a short period of time, preferentially during a time of less than 1 day, 1 hour, 30, 15, 5, 2, or 1 minute, 50, 30, 20, 10, 5, 1, $10^{-1}$, $10^{-2}$, $10^{-3}$, $10^{-4}$, $10^{-5}$, $10^{-6}$, $10^{-7}$, $10^{-8}$, $10^{-9}$, $10^{-10}$, $10^{-11}$, $10^{-12}$, $10^{-13}$, $10^{-14}$, or $10^{-15}$ seconds.

In still another embodiment of the invention, the high ratio enhances the coupling between the magnetic moment of the magnetic nanoparticle and the oscillating magnetic field, where this enhancement is preferentially more pronounced for nanoparticles with such property than for those without such property.

The invention also concerns magnetic nanoparticles for use, in which the high frequency is between 1 and 10 000 kHz.

The invention also relates to magnetic nanoparticles for use, in which the high frequency is between 1 and 1000 kHz.

In one embodiment of the invention, the high frequency $f_h$ is larger than $10^{-10}$, $10^{-9}$, $10^{-8}$, $10^{-7}$, $10^{-6}$, $10^{-5}$, $10^{-4}$, $10^{-3}$, $10^{-2}$, $10^{-1}$, 1, 10, $10^2$, $10^3$, $10^4$, $10^5$, $10^6$, $10^7$, or $10^8$ kHz, or is between $10^{-10}$ and $10^8$ kHz, or between $10^{-5}$ and $10^5$ kHz, or between $10^{-3}$ and $10^3$ kHz, where this frequency may be equal or proportional to $[2\pi/t_1]$, $[1/t_1]$, $[/2\pi/t_2]$, $[1/t_2]$, $[2\pi/t_3]$, $[1/t_3]$, $[2\pi/(t_1+t_2)]$, $[1/(t_1+t_2)]$, $[2\pi/(t_1+t_3)]$, $[1/(t_1+t_3)]$, $[2\pi/(t_2+t_3)]$, $[1/(t_2+t_3)]$, $[2\pi/(t_1+t_2+t_3)]$, or $[1/(t_1+t_2+t_3)]$.

In another embodiment of the invention, $[t_1/t_2]$, $[t_1/t_3]$ or $[t_2/t_3]$, is lower than or equal to $10^{-10}$, $10^{-5}$, $10^{-3}$, $10^{-1}$, 1, 10, $10^2$, $10^3$, $10^5$, or $10^{10}$.

In an embodiment of the invention, the measurement time used to measure one or several high frequency or frequencies of oscillation is the time during which the variation of the amplitude or strength of the magnetic field is measured. This time is preferentially sufficiently long, but not too long, to be able to observe more than 1, 2, 5, 10, 100, or 1000 oscillation(s).

In another embodiment of the invention, the measurement time used to measure the high frequency oscillation lies between $10^{-6}$ and $10^{-4}$ seconds, between $10^{-7}$ and $10^{-3}$ seconds, between $10^{-8}$ and $10^{-1}$ seconds, between $10^{-9}$ and 1 second.

In still another embodiment of the invention, the measurement time used to measure the high frequency oscillation is larger than $10^{-9}$, $10^{-8}$, $10^{-7}$, $10^{-6}$, $10^{-5}$, $10^{-4}$, $10^{-3}$, $10^{-2}$, $10^{-1}$, or 1 second.

In still another embodiment of the invention, the measurement time used to measure the high frequency oscillation is smaller than $10^{-9}$, $10^{-8}$, $10^{-7}$, $10^{-6}$, $10^{-5}$, $10^{-4}$, $10^{-3}$, $10^{-2}$, $10^{-1}$, or 1 second.

In another embodiment of the invention, the time of application of the magnetic field oscillating at high frequency, $f_h$, is sufficiently large and/or the period associated to the high frequency of oscillation, $T_h=1/f_h$, is sufficiently short, so that the high frequency of oscillation does not lead to any temperature decrease, or leads to a temperature decrease of less than 10, 5, 1° C., when a suspension of magnetic nanoparticles, preferentially at a concentration larger than 0.1, 1, or 10 mg/mL, is exposed to this magnetic field. The sole application of the high frequency is preferentially not sufficient to induce cooling steps. This is the reason why it may be necessary to add a low frequency of oscillation to produce cooling steps.

The invention also concerns magnetic nanoparticles for use, wherein the high frequency heats the magnetic nanoparticles.

In one embodiment of the invention, the high frequency of oscillation induces a movement, preferably a rotation, a translation, or a vibration of the nanoparticles, preferentially in the body part of the individual. This movement may be responsible for heating the nanoparticles.

In another embodiment of the invention, the high frequency of oscillation induces a rotation of the magnetic moment of the magnetic nanoparticle. This rotation can be responsible for heating the nanoparticles. The rotation of the magnetic moment can take place alone or in conjunction with the movement of the nanoparticles.

In another embodiment of the invention, the high, medium, and/or low frequency of oscillation does not induce any movement, rotation, translation, or vibration of the nanoparticles, preferentially in the body part of the individual.

In another embodiment of the invention, the high frequency of oscillation is kept sufficiently low, for example to limit undesirable effects, such as Eddy or Foucault currents or other potential toxic effects which may occur at this frequency, i.e. preferentially lower than 1000, 500, 250, 150, 100, 50, 20, 10, 5, or 1 kHz.

In another embodiment of the invention, the high frequency of oscillation enables to heat magnetic nanoparticles without the production of Eddy or Foucault currents.

In still another embodiment of the invention, the high frequency of oscillation enables to heat the magnetic nanoparticles with the production of Eddy or Foucault currents, where the production of such current is preferentially kept sufficiently low to avoid a temperature increase of the body part of the individual exposed to the oscillating magnetic field of more than 0.0001, 0.001, 0.01, 0.1, 1, 2, 5, 10, 20, 50, or 100° C.

In another embodiment of the invention, Eddy or Foucault currents are defined as the heat produced under the application of the oscillating magnetic field by materials, substances, compounds, tissues, cells, or the part of the body part of the individual, which are different from magnetic nanoparticles. Eddy or Foucault currents preferentially occur in region without magnetic nanoparticles or comprising a small concentration of magnetic nanoparticles, preferentially less than $10^9$, $10^6$, $10^3$, 10, 1, $10^{-1}$, $10^{-3}$, $10^{-6}$, or $10^{-9}$ mg of nanoparticles per $mm^3$ of substance, compound, tissue, cell, or the body part of the individual.

In another embodiment of the invention, Eddy or Foucault currents are defined as temperature increases under the application of the oscillating magnetic field, preferentially larger than 0.01, 0.1, 1, 5, 10, or 20° C., preferentially not due to the production of heat by magnetic nanoparticles.

In another embodiment of the invention, Eddy or Foucault currents occur when maximum or average magnetic field is high, preferentially higher or larger than 0.1, 0.5, 1, 5, 10, 20, 50, 100, or 200 mT. In some cases, using oscillating magnetic fields with low maximum or average magnetic field, preferentially lower than 0.1, 0.5, 1, 5, 10, 20, 50, 100, or 200 mT, enables to reduce Eddy or Foucault currents.

In another embodiment of the invention, Eddy or Foucault currents occur when the high oscillation frequency is high, preferentially higher or larger than 0.1, 1, 10, 100, or 1000 kHz.

In still another embodiment of the invention, Eddy or Foucault currents occur when the volume exposed to the oscillating magnetic field is larger than 1, 10, $10^2$, $10^3$, $10^6$, $10^9$, or $10^{15}$ $mm^3$. In some cases, using a low volume exposed to the oscillating magnetic, preferentially lower than 1, 10, $10^2$, $10^3$, $10^6$, $10^9$, or $10^{15}$ $mm^3$, enables to reduce Eddy or Foucault currents.

In another embodiment of the invention, the high frequency of oscillation is kept sufficiently high, for example to be able to heat the nanoparticles or to avoid undesirable effects that may occur at a too low high frequency such as undesired cellular or muscular stimulations, i.e. preferentially larger than 1, 5, 20, 100, 150, 250, 500, or 1000 kHz.

In one embodiment of the invention, to lower the high frequency of oscillation, preferentially below $10^6$, $10^3$, or 10 kHz, nanoparticle concentration is increased, i.e. nanoparticle concentration is larger than 0.01, 0.1, 1, 10, 20, 50, $10^2$, $10^3$, $10^6$ or $10^9$ μg of nanoparticles per $mm^3$ of the body part of the individual, or per $mm^3$.

In one embodiment of the invention, to lower the high frequency of oscillation, preferentially below $10^6$, $10^3$, or 10 kHz, nanoparticle homogeneity of distribution is increased, i.e. nanoparticles occupy more than 5, 10, 25, 50, 75, 80, 85, 90, 95, 98, 100, 150, 200, 500, $10^3$, or $10^5$% of the part of the body part of the individual, where this percentage may represent the volume occupied by the nanoparticles divided by the volume of the body part of the individual. In some cases, the homogeneity of nanoparticle distribution can be increased by using nanoparticles that possess more homogenous distribution, such as nanoparticles or magnetosomes organized in chains, or by using an administration technique that enables to increase homogenous distribution, such as an administration carried out at a flow rate or speed, which is lower than $10^9$, $10^5$, $10^3$, $10^2$, 10, 1 mg of nanoparticles administered to the body part per minute of injection.

In another embodiment of the invention, to lower the high frequency of oscillation, preferentially below $10^6$, $10^3$, or 10 kHz, nanoparticles with high SAR are used, i.e. nanoparticles with SAR preferentially larger than 1, 5, 10, 20, 50, 100, 200, 500, or 1000 W/g. Such nanoparticles may be nanoparticles of large sizes, i.e. of sizes larger than 1, 5, 10, 20, 50, 75, 90, or 100 nm, or monodomain nanoparticles, or ferromagnetic, or ferromagnetic nanoparticles. Such nanoparticles may also distribute homogeneously in the tissues to enable a homogeneous distribution of the temperature. They may be arranged in chains, such as magnetosomes produced by magnetotactic bacteria, which are preferably extracted from these bacteria and purified to remove toxic bacterial residues such as endotoxins. The chain arrangement may yield homogeneous heating and high SAR, preferentially higher or larger than 100, 250, 500, or 1000 W/g.

In another embodiment of the invention, to lower the high frequency of oscillation, preferentially below $10^6$, $10^3$, or 10 kHz, maximum or average magnetic field can be increased above 1, 2, 5, 10, 15, 20, 25, 30, 40, 50, 75, 100, 250, 500, or 1000 mT.

The invention also relates to magnetic nanoparticles for use, wherein the medium frequency lies between $10^{-5}$ and $10^6$ Hz.

The invention also relates to magnetic nanoparticles for use, wherein the medium frequency is lower than the high frequency and lies between $10^{-5}$ and $5.10^5$ Hz.

In one embodiment of the invention, the medium oscillation frequency is larger than $10^{-10}$, $10^{-9}$, $10^{-8}$, $10^{-7}$, $10^{-6}$, $10^{-5}$, $10^{-4}$, $10^{-3}$, $10^{-2}$, $10^{-1}$, 1, 10, $10^2$, $10^3$, $10^4$, $10^5$, $10^6$, $10^7$, or $10^8$ Hz.

In one embodiment of the invention, the medium oscillation frequency is smaller than $10^{-10}$, $10^{-9}$, $10^{-8}$, $10^{-7}$, $10^{-6}$, $10^{-5}$, $10^{-4}$, $10^{-3}$, $10^{-2}$, $10^{-1}$, 1, 10, $10^2$, $10^3$, $10^4$, $10^5$, $10^6$, $10^7$, or $10^8$ Hz.

In another embodiment of the invention, the medium oscillation frequency lies between $10^{-20}$ and $10^{20}$ Hz, $10^{-10}$ and $10^{10}$ Hz, $10^{-8}$ and $10^8$ Hz, $10^{-6}$ and $10^6$ Hz, $10^{-5}$ and $10^5$ Hz, $10^{-4}$ and $10^4$ Hz, or between $10^{-3}$ and $10^3$ Hz.

In one embodiment of the invention, the medium frequency of oscillation is 1.001, 1.01, 1.1, 2, 5, 10, $10^2$, $10^3$, $10^4$, $10^5$, or $10^{10}$ times lower than the high frequency of oscillation.

In one embodiment of the invention, the medium frequency of oscillation takes place in at least 1, 2, 5, 10, $10^2$, $10^3$, $10^5$, $10^{10}$, $10^{20}$, or $10^{50}$ cycles.

In an embodiment of the invention, the measurement time used to measure the medium frequency of oscillation is the time during which the variation of the amplitude or strength of the magnetic field is measured. This time is preferentially sufficiently long, but not too long, to be able to observe more than 1, 2, 5, 10, 100, or 1000 medium frequency oscillations.

In another embodiment of the invention, the measurement time used to measure the medium frequency oscillation lies between $10^{-6}$ and $10^{-4}$ seconds, between $10^{-7}$ and $10^{-3}$ seconds, between $10^{-8}$ and $10^{-1}$ seconds, between $10^{-9}$ and 1 second.

In still another embodiment of the invention, the measurement time used to measure the medium frequency oscillation is larger than $10^{-9}$, $10^{-8}$, $10^{-7}$, $10^{-6}$, $10^{-5}$, $10^{-4}$, $10^{-3}$, $10^{-2}$, $10^{-1}$, 1, 10, $10^2$, or $10^3$ second.

In still another embodiment of the invention, the measurement time used to measure the medium frequency oscillation is smaller than $10^{-9}$, $10^{-8}$, $10^{-7}$, $10^{-6}$, $10^{-5}$, $10^{-4}$, $10^{-3}$, $10^{-2}$, $10^{-1}$, 1, 10, $10^2$, or $10^3$ second.

In still another embodiment of the invention, the measurement time used to measure the medium frequency of oscillation is 1.001, 1.01, 1.1, 1.5, 2, 5, 10, 100, 1000, or 10000 longer than measurement time used to measure the high frequency of oscillation.

In still another embodiment of the invention, the medium frequency of oscillation is too high, and/or the time $t_5$ is too short, to enable a decrease in temperature of the magnetic nanoparticles or of their surroundings, preferentially to yield a temperature decrease of more than 1, 5, 10, 50, or 100° C., when a suspension of magnetic nanoparticles, preferentially at a concentration of more than 0.1, 1, or 10 mg/mL, is exposed to this magnetic field, where temperature is measured between at least 1, 10, 100, or 1000 high frequency oscillations. The fact that the medium frequency of oscillation can't result in temperature decrease can be problematic in a magnetic hyperthermia treatment, since it can possibly lead to Eddy or Foucault currents or to other side effects due to continuous heating, possibly leading to overheating. This is the reason why it may appear necessary to add a low frequency of oscillation that enables cooling steps.

The invention also concerns magnetic nanoparticles for use, wherein the medium frequency modulates the high frequency.

In one embodiment of the invention, the modulation of the high frequency of oscillation by the medium frequency of oscillation corresponds to a magnetic field oscillating at a high frequency within an envelope function oscillating at a medium frequency.

In one embodiment of the invention, the purpose of the envelope function may be to reach higher or larger maximum or average magnetic fields than those reached without the envelope function, of maximum or average magnetic fields preferentially larger than 1, 5, 10, 50, 100, 500, or 1000 mT, preferentially reached during short times, most preferentially during less than $10^{-2}$, $10^{-3}$, $10^{-4}$, $10^{-5}$, or $10^{-6}$ seconds, or most preferentially during less than 80, 70, 50, 20, 10, 5, or 1% of the duration of one medium frequency cycle.

In one embodiment of the invention, the purpose of the envelope function may also be to reach magnetic fields with maximum or average magnetic field larger than 1, 10, 100, 500, or 1000 mT, or with maximum or average magnetic field higher or larger, preferentially 1.01, 1.1, 1.2, 2, 5, 10, 20, 30, 50, or 100 times higher or larger, than that reached by a magnetic field oscillating at the high frequency without the envelope function.

In one embodiment of the invention, the high maximum or average magnetic field produced by the modulation occurs preferentially within part of a cycle associated to a medium frequency, preferentially within less than 90, 80, 75, 50, 25, 15, 10, 5, 2, or 1% of this cycle.

The invention also concerns magnetic nanoparticles for use, wherein the medium frequency leads to increased heating properties of the magnetic nanoparticles.

The invention also relates to magnetic nanoparticles for use according to the invention, wherein the low frequency is lower than the high frequency and the medium frequency when it is present and lies between $10^{-9}$ and $5.10^5$ Hz.

In an embodiment of the invention, the low frequency lies between $10^{-15}$ and $10^{15}$ Hz, between $10^{-12}$ and $10^{12}$ Hz, between $10^{-9}$ and $10^9$ Hz, between $10^{-9}$ and $10^5$ Hz, between $10^{-6}$ and $10^5$ Hz, between $10^{-3}$ and $10^3$ Hz. In some cases, the low frequency can be lower than $10^{-15}$, $10^{-12}$, $10^{-9}$, $10^{-7}$, $10^{-5}$, $10^{-3}$, $10^{-1}$, 1, 10, $10^3$, $10^5$, $10^7$, $10^9$, $10^{12}$, or $10^{15}$ Hz. In some cases, the low frequency can be larger than $10^{-15}$, $10^{-12}$, $10^{-9}$, $10^{-7}$, $10^{-5}$, $10^{-3}$, $10^{-1}$, 1, 10, $10^3$, $10^5$, $10^7$, $10^9$, $10^{12}$, or $10^{15}$ Hz.

In one embodiment of the invention, the medium frequency increases nanoparticle heating power, i.e. it increases nanoparticle SAR by a factor of more than 1.00001, 1.0001, 1.001, 1.01, 1.1, 1.2, 1.5, 2, 5, 10, $10^2$, or $10^3$ times the SAR of the same nanoparticles, measured with a magnetic field oscillating without the medium frequency.

In still another embodiment of the invention, the medium frequency of oscillation leads to a high nanoparticle heating power, i.e. it enables to reach SAR values of more than 1, 10, 100, 250, 500, or 1000 $W/g_{Fe}$.

The invention also concerns magnetic nanoparticles for use, in which the low frequency induces at least one cycle comprising a heating step and a cooling step.

In one embodiment of the invention, the heating step is triggered by the application of the oscillating magnetic field, preferably in a region containing a sufficiently high concentration of magnetic nanoparticles to induce heating.

In one embodiment of the invention, the heating step lasts at least 1 µs, 10 µs, 100 µs, 1 ms, 10 ms, 100 ms, 1 s, 10 s, or 100 s (seconds). In this case, it can take place when the low frequency of oscillation is lower than $10^6$, $10^5$, $10^4$, $10^3$, $10^2$, 10, 1, $10^{-1}$, or $10^{-2}$ Hz, and preferentially the high frequency of oscillation is larger than 0.1, 1, 10, 100, 200, 500, $10^3$, $10^4$, or $10^5$ kHz. The heating step can last longer when nanoparticles are less concentrated in the body part of the individual or have diffused outside of the body part of the individual, where such diffusion can take place 1, 2, 6, or 12 hours, 1, 2, or 7 days, 1, 2, or 4 weeks, 1, 2, or 6 months, 1, 2, or 10 years, following nanoparticle administration.

In another embodiment of the invention, the heating step lasts less than 1 µs, 10 µs, 100 µs, 1 ms, 10 ms, 100 ms, 1 s, 10 s, or 100, seconds, 5, 10, 20, or 30 minutes. In this case, it can take place when the low oscillation frequency is lower than $10^6$, $10^5$, $10^4$, $10^3$, $10^2$, 10, 1, $10^{-1}$, or $10^{-2}$ Hz, and the high oscillation frequency is preferentially larger than 0.1, 1, 10, 100, 200, 500, $10^3$, $10^4$, or $10^5$ kHz. The heating step may take less time when the magnetic nanoparticles have not diffused outside of the body part of the individual, preferentially during a time, which is less than 1, 2, 6, or 12 hours, 1, 2, or 7 days, 1, 2, or 4 weeks, 1, 2, or 6 months, 1, 2, or 10 years, depending on nanoparticle administration route.

In one embodiment of the invention, the duration of the heating step is as short as possible to limit Eddy or Foucault currents or undesirable or toxic effects associated with the application of the oscillating field over a long period of time.

In one embodiment of the invention, the heating step takes place during the time necessary to reach a temperature obtained during a hyperthermia session or treatment, or a temperature obtained during a thermoablation session or treatment, or a temperature above 37, 48, 49, 50, 55, 60, 65, 70, 75, 80, 85, 90, 95, 100, $10^3$, $10^5$, or $10^{10}$° C., or a temperature between 37 and 1000° C., 37 and 100° C., 37 and 70° C., 37 and 55° C., 37 and 50° C., or between 37 and 45° C.

In another embodiment of the invention, the heating time $t_7$ or $t_9$ is sufficiently long to induce the temperature increase.

According to the invention, the temperature increase can be larger than 1, 2, 3, 4, 5, 6, 7, 8, 9, 10, 11, 12, 13, 14, 15, 20, 25, 30, 35, 40, 45, 50, 55, 60, 65, 70, 80, 85, 90, 100, 250, 500, or $10^3$° C., or ° C. per second, or ° C. per hour, where this temperature increase preferentially represents a temperature increase above physiological temperature.

According to the invention, the temperature increase can be smaller than 1, 2, 3, 4, 5, 6, 7, 8, 9, 10, 11, 12, 13, 14, 15, 20, 25, 30, 35, 40, 45, 50, 55, 60, 65, 70, 80, 85, 90, 100, 250, 500, or $10^3$° C., or ° C. per second, or ° C. per hour, where this temperature increase preferentially represents a temperature increase above physiological temperature.

In another embodiment of the invention, the heating time $t_7$ or $t_9$ is sufficiently long or the low frequency is sufficiently small to reach a temperature plateau. Such a plateau can be achieved when the temperature increase is less than 1° C. per day, 1° C. per minute, 1° C. per second, or 1° C. per microsecond, or when the temperature increase is $10^4$, $10^3$, $10^2$, 10, 5, or 2 times lower than the initial temperature increase, measured at the beginning of the heating step, preferentially during the 100, 10, 1, 0.1, or 0.01 seconds following the switching on of the magnetic field or of the device generating the magnetic field.

In an embodiment of the invention, the heating time $t_7$ or $t_9$ can be reduced by increasing the maximum or average magnetic field, and/or high frequency. It is thus preferable to apply an oscillating magnetic field with a maximum or average magnetic field larger than 0.01, 0.1, 1, 5, 10, 20, 40 mT and/or high oscillation frequency larger than 0.1, 100, 200, 500, $10^3$, $10^4$, or $10^5$ kHz, to yield a heating time $t_7$ or $t_9$, which is lower than 1 µs, 10 µs, 100 µs, 1 ms, 10 ms, 100 ms, 1 s, 10 s, or 100 seconds.

In one embodiment of the invention, to decrease the nanoparticle heating time $t_7$ or $t_9$, nanoparticle SAR is increased, preferentially above 1, 10, 25, 50, 100, 250, 500, or 1000 W/g, or the power of the oscillating magnetic field is increased above $10^{-4}$, $10^{-2}$, $10^{-1}$, 1, 10, $10^2$, or $10^3$ Watt per cm$^3$ of body part and/or nanoparticle homogeneity of distribution is increased in the body part of the individual.

In an embodiment of the invention, the heating time $t_7$ or $t_9$ increases when the maximum or average magnetic field and/or high oscillation frequency decrease(s). It can thus be preferred to apply an oscillating magnetic field with a maximum or average magnetic field, which is lower than 0.01, 0.1, 1, 5, 10, 20, or 40 mT and/or a high oscillation frequency, which is lower than 0.1, 1, 10, 100, 200, 500, $10^3$, $10^4$, or $10^5$ kHz, to achieve a heating step that lasts longer than 1 µs, 10 µs, 100 µs, 1 ms, 10 ms, 100 ms, 1 s, 10 s or 100 s (seconds).

In an embodiment of the invention, the cooling time $t_8$ or $t_{10}$ is shorter than 1 day, 12, 4, 2, or 1 hour, 60, 30, 20, 2, or 1 minute, 40, 30, or 20 seconds.

In another embodiment of the invention, the cooling time $t_8$ or $t_{10}$ is independent of nanoparticle concentration.

In still another embodiment of the invention, low frequency cycles are associated with cooling times $t_8$ or $t_9$ shorter than 1 day, 12, 4, 2, or 1 hour, 60, 30, 20, 2, or 1 minute, 40, 30, or 20 seconds, and/or with heating times $t_7$ or $t_{10}$ shorter than 1 day, 12, 4, 2, or 1 hour, 60, 30, 20, 2, or 1 minute, 40, 30, or 20 seconds.

In some cases, it may be preferable to favor short heating and/or cooling steps, preferentially if it is desired to induce a large number of temperature gradients. This may be the case if one wishes to trigger certain mechanisms, such as an immune mechanism, preferably a mechanism involved in pathological or tumor cell destruction.

In other cases, it may be preferable to favor long heating and/or cooling steps, preferentially if it is desired to keep the temperature constant over a long period of time. This may be the case if one wishes to destroy cells using constant temperatures during a long period.

In an embodiment of the invention, the measurement time used to measure one or several frequencies of oscillation is the time during which the variation of the amplitude or strength of the magnetic field is measured, or the time during which the variation of the power of the oscillating magnetic field is measured. This time is preferentially sufficiently long, but not too long, to be able to observe more than 1, 2, 5, 10, 100, or 1000 low frequency of oscillation.

In another embodiment of the invention, the measurement time used to measure the low frequency oscillation lies between $10^{-6}$ and $10^4$ seconds, between $10^{-3}$ and $10^3$ seconds, between $10^{-1}$ and $10^3$ seconds, between 1 and 100 second.

In still another embodiment of the invention, the measurement time used to measure the low frequency oscillation is larger than $10^{-6}$, $10^{-5}$, $10^{-4}$, $10^{-3}$, $10^{-2}$, $10^{-1}$, 1, 10, $10^2$, $10^3$, or $10^4$ seconds.

In still another embodiment of the invention, the measurement time used to measure the low frequency oscillation is smaller than $10^{-6}$, $10^{-5}$, $10^{-4}$, $10^{-3}$, $10^{-2}$, $10^{-1}$, 1, 10, $10^2$, $10^3$, or $10^4$ seconds.

The invention also concerns magnetic nanoparticles for use, wherein the heating step produces a temperature increase of more than 1° C. of the body part.

In one embodiment of the invention, the heating step leads to a temperature increase of more than 1, 2, 3, 4, 5, 6, 7, 8, 9, 10, 11, 12, 13, 14, 15, 20, 25, 30, 35, 40, 45, 50, 55, 60, 65, 70, 80, 85, 90, 100, 250, 500, or $10^{3}$° C., or ° C. per second, or ° C. per hour, preferentially of the body part. This temperature increase can be measured between the beginning of magnetic field application and the time when magnetic field application is stopped. This increase in temperature may correspond to an increase in temperature above the physiological temperature.

In one embodiment, the physiological temperature may be the temperature of the body part of the individual, preferentially measured when this individual is in its normal condition. According to the invention, physiological temperature may be 37° C., or between 36.1 and 37.8° C.

In another embodiment of the invention, the increase in temperature is an increase in temperature of the body part of the individual, preferentially containing a concentration in magnetic nanoparticles larger than 1 ng, or 10 ng, or 100 ng, or 1 µg, or 10 µg, or 100 µg, or 1 mg, or 10 mg, or 100 mg per $mm^3$, or per $mm^3$ of the body part of the individual.

In another embodiment of the invention, temperature increase is caused by applying an oscillating magnetic field at one or more than one high oscillation frequency, preferentially larger than 10, 50, 100, 250, 500, or 1000 kHz.

In still another embodiment of the invention, temperature increase is caused by applying an oscillating magnetic field of power larger than $10^{-15}$, $10^{-9}$, $10^{-5}$, $10^{-2}$, 1, 10, $10^2$, $10^3$, or $10^5$ Watt per $cm^3$ of body part.

In one embodiment of the invention, the increase in temperature occurs selectively in the body part of the individual. This may be possible when nanoparticles are in sufficient concentration in the body part of the individual, i.e. at a concentration, which is larger than 1 ng, or 100 ng, or 100 µg, or 1 µg, or 10 µg, or 100 µg, or 1 mg, or 10 mg, or 100 mg per $mm^3$, or per $mm^3$ of the body part of the individual and the magnetic field is applied, preferentially selectively to the body part of the individual, preferentially the magnetic field is applied with a high frequency larger than 10, 50, 100, 250, 500, or 1000 kHz.

In an embodiment, the heating step is associated with an active temperature increase, i.e. a temperature increase preferentially due to magnetic nanoparticles being exposed to the oscillating magnetic field.

The invention also concerns magnetic nanoparticles for use, wherein the cooling step induces a temperature decrease of more than 1° C. of the body part.

In one embodiment of the invention, the cooling step produces a temperature decrease of more than 1, 2, 3, 4, 5, 6, 7, 8, 9, 10, 11, 12, 13, 14, 15, 20, 25, 30, 35, 40, 45, 50, 55, 60, 65, 70, 80, 85, 90, 100, 250, 500, or $10^{3}$° C., or ° C. per second, or ° C. per hour, preferentially of the body part. This decrease can be measured between the end of the $A_7$ or $A_9$ low frequency sequence, preferentially when magnetic field application is stopped, and the time when physiological temperature is reached or a temperature above physiological temperature by 0.1, 1, 2, 3, 4, 5, 6, 7, 8, 9, 10, 11, 12, 13, 14, 15, 20, 25, 30, 35, 40, 45, 50, 55, 60, 65, 70, 80, 85, 90, 100, 250, 500, or $10^{3}$° C., is reached.

In one embodiment of the invention, the cooling step may be accelerated by using an apparatus, a refrigerant, an ice cube, a chemical, or a substance, which cools down the body part of the individual or the magnetic nanoparticle.

In another embodiment of the invention, the amplitude of temperature decrease of the cooling step does not differ by more than a factor of 1.001, 1.01, 1.1, 1.2, 1.5, 2, 5, 10, $10^2$, or $10^3$, from the amplitude of temperature increase of the heating step. This may preferentially be used when one wants to take advantage of both heating and cooling steps on the therapeutic effect.

In still another embodiment of the invention, the amplitude of temperature decrease of the cooling step differs by more than a factor of 1.001, 1.01, 1.1, 1.2, 1.5, 2, 5, 10, $10^2$, or $10^3$, from the amplitude of temperature increase of the heating step. This may preferentially be used when one wants to take advantage of either the heating or the cooling step on the therapeutic effect.

The invention also concerns magnetic nanoparticles for use, wherein the low frequency of oscillation enables to limit undesirable effects.

In an embodiment of the invention, the creation of cycles with heating and cooling steps enables to limit toxicity. First, the average temperatures reached using these steps are lower, preferentially by more than 1, 2, 3, 4, 5, 7, 10, 20, 50, 100, 500, or 1000° C., than those reached without these steps. Second overheating, preferentially due to Eddy or Foucault currents, can be avoided since the body part of the individual can be cooled down or remain without any temperature increase during the cooling steps.

According to the invention, a low frequency can yield a number of heating and/or cooling steps or a number of heating and/or cooling gradients, which is 2, 3, 5, 10, $10^2$, $10^3$, $10^5$, $10^{10}$, or $10^{20}$ greater than the number of steps or gradients without the low frequency.

In an embodiment, the cooling step is associated with a passive temperature decrease, i.e. a temperature decrease which is preferentially due to the temperature decrease of the body part of the individual without application of a magnetic field, which can be due to blood circulation.

The invention also concerns magnetic nanoparticles for use, wherein the low frequency of oscillation enables to improve treatment or diagnosis efficacy, or enables to reach a more efficient treatment or diagnosis than without the low frequency.

In an embodiment of the invention, the low frequency of oscillation improves treatment or diagnosis efficacy by increasing the number of heating and cooling steps, preferentially the number of temperature gradients associated to each heating and cooling step, preferentially by producing more than $10^9$, $10^7$, $10^5$, $10^3$, 10, or 1 temperature gradient(s). Such gradients could more efficiently destroy pathological cells, for example by more efficiently activating the immune system or by more efficiently inducing a stress, preferentially a cellular stress, than a continuous heating, which is associated with a fewer number of temperature gradients, preferentially less than $10^9$, $10^7$, $10^5$, $10^3$, 10, or 1 temperature gradient(s).

The invention also concerns magnetic nanoparticles for use, wherein the medium and/or low frequency of oscillation enable(s) to increase the ratio between maximum and average magnetic fields.

In another embodiment of the invention, the application of the magnetic field, oscillating at high and medium and/or low frequency, enables to reach average magnetic fields that are lower than 100, 50, 20, 10, 9, 8, 7, 6, 5, 4, 3, 2, 1, or 0.1 mT, or that are lower than those reached without the medium and/or low frequency by a factor of 1.001, 1.01, 1.1, 1.2, 1.5, 2, 5, 10, 20, 30, 50, or 100.

In another embodiment of the invention, the application of the magnetic field, oscillating at high and medium and/or low frequency, enables to reach maximum magnetic fields that are larger than 100, 50, 20, 10, 9, 8, 7, 6, 5, 4, 3, 2, 1, or 0.1 mT, or that are larger than those reached without the medium and/or low frequency by a factor of 1.001, 1.01, 1.1, 1.2, 1.5, 2, 5, 10, 20, 30, 50, or 100.

In still another embodiment of the invention, the application of the magnetic field, oscillating at high and medium and/or low frequency, enables to reach maximum magnetic fields over a short period of time, preferentially less than 1 hour, 30, 15, 5, 2, or 1 minute, 30, 15, 10, 5, 2, 1, $10^{-1}$, $10^{-2}$, $10^{-3}$, $10^{-4}$, $10^{-5}$, $10^{-6}$, $10^{-7}$, $10^{-8}$, $10^{-9}$, $10^{-10}$, $10^{-11}$, $10^{-12}$, $10^{-13}$, $10^{-14}$, or $10^{-15}$ seconds.

In still another embodiment of the invention, the application of the magnetic field, oscillating at high and, medium and/or low frequency, enables to reach maximum magnetic fields over a shorter period of time, preferentially by a factor of 1.001, 1.01, 1.1, 1.2, 1.5, 2, 5, 10, 20, 30, 50, or 100, compared with the magnetic field oscillating without the medium and/or low frequency.

In another embodiment of the invention, the application of the magnetic field, oscillating at high and, medium and/or low frequency, enables to increase the ratio between maximum and average magnetic fields by a factor of 1.001, 1.01, 1.1, 1.2, 1.5, 2, 5, 10, 20, 30, 50, or 100 compared with the same ratio measured without the medium and/or low frequency.

In still another embodiment of the invention, the application of the magnetic field, oscillating at high and, medium and/or low frequency, enables to reach a ratio between maximum and average magnetic fields, which is larger than 1.00001, 1.0001, 1.001, 1.01, 1.1, 1.2, 1.5, 2, 3, 4, 5, 6, 7, 8, 9, 10, 15, 20, 50, 100, 250, 500, $10^3$, $10^4$, or $10^6$.

The invention also concerns magnetic nanoparticles for use, wherein the medium and/or low frequency of oscillation decrease magnetic nanoparticle diffusion outside of the body part.

In one embodiment of the invention, the medium and/or low frequency of oscillation enable to heat the body part or magnetic nanoparticle during a time, which is 2, 5, 10, or 100 times longer than without the medium and/or low frequency of oscillation.

In another embodiment of the invention, the medium and/or low frequency of oscillation enable to heat the body part or magnetic nanoparticle during more than 1 minute, 1 hour, 1 day, 1 week, 1 month, or 1 year, following nanoparticle administration.

The invention also relates to magnetic nanoparticles, wherein the medium and/or low frequency of oscillation increase the release of a compound from the magnetic nanoparticles.

In one embodiment of the invention, the compound is a fluorescent substance, a medical, therapeutic, diagnostic compound, a compound of interest for biological, chemical or physical research, a compound used for depollution, detection of a physicochemical disturbance such as temperature, or of a radiation.

In another embodiment of the invention, the release of the compound corresponds to the diffusion of the compound at some distance from the nanoparticles, preferentially at a distance larger than $10^{-15}$, $10^{-6}$, $10^{-3}$, 1, $10^3$, $10^6$, or $10^9$ meters from the nanoparticles.

In another embodiment of the invention, the release of the compound is increased when the quantity of released compound is multiplied by a factor of 1.01, 1.1, 1.2, 1.5, 2, 5, 10, $10^3$, $10^5$, $10^7$, or $10^{10}$, in the presence of the low and/or medium frequency compared with a situation where the low and/or medium frequency is/are missing.

In another embodiment of the invention, the release of the compound corresponds to the diffusion of the compound at some distance from the nanoparticles, preferentially at a distance smaller than $10^{-15}$, $10^{-6}$, $10^{-3}$, 1, $10^3$, $10^6$, or $10^9$ meters from the nanoparticles.

In another embodiment of the invention, the release of the compound is increased when the quantity of released compound is multiplied by a factor of 1.01, 1.1, 1.2, 1.5, 2, 5, 10, $10^3$, $10^5$, $10^7$, or $10^{10}$, in the presence of the low and/or medium frequency compared with a situation where the low and/or medium frequency is/are missing.

In still another embodiment of the invention, the release of the compound is increased when the quantity of compound released, preferentially measured more than 100, 10, 1, $10^{-1}$, $10^{-3}$, or $10^{-6}$ minutes following the activation or switching on of the oscillating magnetic field, is multiplied by a factor of more than 1.1, 1.5, 2, 5, 10, 100, $10^3$, $10^5$, or $10^9$.

In still another embodiment of the invention, the release of the compound is increased when the quantity of compound released, preferentially measured more than 100, 10, 1, $10^{-1}$, $10^{-3}$, or $10^{-6}$ minutes following the activation or switching on of the oscillating magnetic field, is multiplied by a factor of less than 1.1, 1.5, 2, 5, 10, 100, $10^3$, $10^5$, or $10^9$.

In still another embodiment of the invention, the release of the compound is increased when the quantity of compound initially released, measured less than 100, 10, 1, $10^{-1}$, $10^{-3}$, or $10^{-6}$ minutes following the activation or switching on of the oscillating magnetic field, is multiplied by a factor of more than 1.1, 1.5, 2, 5, 10, 100, $10^3$, $10^5$, or $10^9$.

In still another embodiment of the invention, the release of the compound is increased when the quantity of compound initially released, measured less than 100, 10, 1, $10^{-1}$, $10^{-3}$, or $10^{-6}$ minutes following the activation or switching on of the oscillating magnetic field, is multiplied by a factor of less than 1.1, 1.5, 2, 5, 10, 100, $10^3$, $10^5$, or $10^9$.

The invention also concerns magnetic nanoparticles for use, wherein the low frequency of oscillation enables to improve treatment efficacy against an infectious disease such as a cancer or tumor.

In one embodiment of the invention, the creation of cycles with heating and cooling steps enables to create at least 1, 2, 5, 10, $10^2$, $10^3$, or $10^5$ temperature gradient(s) of more than 0.01, 0.1, 1, 2, 5, 10, 15, 30, 50, 100, 500, or 1000° C. or 1000° C. per second or 1000° C. per minute or 1000° C. per hour. These temperature gradients are preferentially those occurring at the beginning of the magnetic excitation, preferentially less than $10^{15}$, $10^{12}$, $10^9$, $10^5$, $10^3$, $10^2$, 10, 1, or $10^{-1}$ seconds following the application of the oscillating magnetic field. These temperature gradients can be more efficient in the treatment of an infectious disease, preferentially in the destruction of a tumor, or enable to destroy at least 10, $10^2$, $10^3$, $10^6$, or $10^9$ times more cells, preferentially tumor cells, than a constant temperature. Between the different cycles, temperature gradients preferentially do not vary by more than $10^9$, $10^7$, $10^5$, $10^3$, 100, 10, 1, $10^{-3}$, $10^{-5}$, $10^{-7}$, or $10^{-9}$%.

The invention also relates to magnetic nanoparticles exposed to the oscillating magnetic field for use according to the invention, comprising cycles with heating and cooling steps, wherein: i) the maximum and minimum temperatures to be reached during the heating and cooling steps, respectively, are determined, ii) at least one parameter of the magnetic field modulating the temperature is set at a first value to reach the maximum temperature during the heating step and then the at least one parameter is set at a second value to reach the minimum temperature during the cooling step, optionally iii) the heating and cooling times required to reach these two temperatures are measured, and optionally iv) the heating and cooling steps are repeated at least during the measured heating and cooling times.

The invention also relates to magnetic nanoparticles for use according to the invention, in which the magnetic field comprises or triggers cycles with heating and cooling steps, wherein: i) the maximum and minimum temperatures to be reached during the heating and cooling steps, respectively, are determined, ii) at least one parameter of the magnetic field modulating the temperature is set at a first value to reach the maximum temperature during the heating step and then the at least one parameter is set at a second value to reach the minimum temperature during the cooling step, optionally iii) the heating and cooling times required to reach these two temperatures are measured, and optionally iv) the heating and cooling steps are repeated at least during the measured heating and cooling times.

The invention also relates to magnetic nanoparticles, wherein the at least one parameter is selected from the group consisting of: average or maximum magnetic field amplitude, magnetic field strength, amplitude, frequency, spatial or temporal distribution of magnetic field lines.

In one embodiment of the invention, the at least one parameter is a parameter of the device generating the alternating magnetic field. It can be the strength, amplitude, frequency, power, or duration of application of the alternating current generating the alternating magnetic field.

In one embodiment of the invention, a pre-calibration curve is realized to determine the heating and cooling times, which are necessary to reach the maximum and minimum temperatures, respectively, preferentially reached during low frequency cycles. Such pre-calibration can be realized using magnetic nanoparticles, preferentially mixed in suspension, with cells or with tissue, using conditions that are preferentially as close as possible from those of the treatment, i.e. using for example similar nanoparticle concentration and/or nanoparticle environment than those of the treatment. In some cases, the pre-calibration curve can be realized directly in the individual, for example when it is possible to measure the temperature in the body part of the individual, for example by introducing a temperature probe in such part. The pre-calibration curve may in some cases be realized in the individual, for example during the first session of magnetic hyperthermia treatment. For pre-calibration, the magnetic nanoparticles or the body part of the individual are preferentially exposed to the magnetic field oscillating at the high and low frequency, or at the high, medium and low frequency. The parameter of the device, such as the alternating current, is preferentially set at a first value to reach an average or maximum magnetic field that leads to a maximum temperature, preferentially between 40 and 60° C., during the heating step and then the parameter of the device such as the alternating current is preferentially set at a second value to reach another average or maximum magnetic field that leads to a minimum temperature, preferentially between 30 and 40° C., most preferentially the physiological temperature, during the cooling step. The heating and cooling times required to reach these two temperatures may then be measured and the heating and cooling steps may be repeated, preferentially more than 1, 2, 5, 10, or 100 times. The first and second values of the alternating current may preferentially be constant to simplify the treatment. Indeed, varying such values during the heating and/or cooling step(s) of a magnetic hyperthermia treatment would probably necessitate the use of additional software, and it appears that this is unnecessary. At the end, values of heating and cooling times can be used as such for the treatment, or can be modified to take into account the different conditions used for pre-calibration and for treatment such as differences in nanoparticle distribution, or can be averaged and average heating and cooling times may then be used for the treatment.

In one embodiment of the invention, the maximal temperature, $T_{max}$, and minimal temperature, $T_{min}$, preferentially reached during low frequency cycles, are those which yield optimal therapeutic activity. Such optimal therapeutic activity may correspond to the destruction of more than 1, 2, 5, 10, $10^2$, $10^3$, $10^5$, $10^{10}$, or $10^{20}$ cells, preferentially tumor cells, of virus, of bacteria, preferentially pathogenic bacteria, organs, tissues, vessels, the body part of the individual. Such destruction may in some cases be directly caused by heat, and in some other cases involve indirect mechanism such as the immune system.

In another embodiment of the invention, $T_max$ and $T_{min}$, preferentially reached during low frequency cycles, yield the lowest undesirable effects resulting from the treatment. This may correspond to the destruction of less than 1, 2, 5, 10, $10^2$, $10^3$, $10^5$, $10^{10}$, or $10^{20}$ healthy cells or to the absence of damage towards healthy cells.

In another embodiment of the invention, $T_{max}$ and $T_{min}$, preferentially reached during low frequency cycles, yield the highest anti-tumor efficacy with the lowest toxicity of the treatment.

In one embodiment of the invention, $T_{max}$, preferentially reached during low frequency cycles, is larger than the physiological temperature by 0.1, 0.5, 1, 2, 3, 4, 5, 6, 7, 8, 9, 10, 15, 20, 25, 30, 35, 40, 50, 75, 100, 500, $10^3$, $10^4$, or $10^5$° C. $T_{max}$ can be between 0 and 100° C., 20 and 75° C., 30 and 60° C., 37 and 50° C., 37 and 45° C., or between 37 and 41° C.

In another embodiment of the invention, $T_{min}$, preferentially reached during low frequency cycles, is above or below the physiological temperature by 0.1, 0.5, 1, 2, 3, 4, 5, 6, 7, 8, 9, 10, 15, 20, 25, 30, 35, 40, 50, 75, 100, 500, or $10^3$° C. $T_{min}$ can be between 0 and 100° C., 20 and 75° C., 30 and 60° C., 37 and 50° C., 37 and 45° C., or between 37 and 41° C.

In one embodiment of the invention, the maximum temperature and/or the difference between the minimum and maximum temperatures, preferentially reached during low frequency cycles, favors an indirect mechanism of destruction of the infectious disease, preferentially the tumor, such as an immune mechanism. This may occur when maximum temperatures are moderate, preferably lower than 100, 80, 60, 55, 50, 45, or 43° C. This may also occur when the difference between minimum and maximum temperature is moderate, preferably lower than 100, 75, 50, 25, 10, 9, 8, 7, 6, 5, 4, 3, 2, or 1° C.

In another embodiment of the invention, the maximum temperature or the difference between maximum and minimum temperatures, preferentially reached during low frequency cycles, favors a direct thermal mechanism of destruction of the infectious disease, preferentially the tumor. This may occur when the maximum temperature is high, preferentially larger than 100, 80, 60, 50, 45, or 43° C. This may also occur when the differences between the minimum and maximum temperature is larger than 100, 75, 50, 25, 10, 9, 8, 7, 6, 5, 4, 3, 2, or 1° C.

In one embodiment of the invention, maximal and minimal temperatures are fixed before the beginning of the treatment depending on the body part of the individual, on its size, shape, composition, nature, and on the desired therapeutic effect.

The invention also concerns magnetic nanoparticles for use, for the prevention or treatment of a disease selected from a cancer, a tumor and an infection.

In one embodiment of the invention, the disease is selected from one of the disease mentioned in the 10th revision of the International Statistical Classification of Diseases and Related Health Problems (ICD), maintained by the World Health Organization.

In one embodiment of the invention, the disease is an infectious disease, such as a disease due to a proliferation of bacteria, preferentially pathogenic, of viruses, or of cells, preferentially tumor.

In one embodiment of the invention, the disease is a brain tumor, cervical cancer, colorectal cancer, cutaneous tumor, endometrial cancer, stomach cancer, liver cancer, gastrointestinal stromal tumor, malignant hemopathy, leukemia, multiple myeloma, lymphoma, Hodgkin's disease, non-Hodgkin's lymphoma, hepatocellular carcinoma, Kaposi's sarcoma, laryngeal cancer, mesothelioma, cancer of the esophagus, osteosarcoma, ovarian cancer, pancreatic cancer, skin cancer, oral cancer, lung cancer, small cell lung carcinoma, prostate cancer, rhabdomyosarcoma, kidney cancer, breast cancer, testicular cancer, thyroid cancer, soft tissue sarcoma, bladder carcinoma, myeloma (bone cancer), plasmacytoma, myeloma, germ cell cancer, neuroblastoma, osteosarcoma, retinoblastoma, cancer of the central nervous system, wilms tumor or nephroblastoma.

In one embodiment of the invention, the disease is associated with the condition of the individual or of the body part of the individual that is different from a normal condition. The disease can occur locally or on an entire organism or individual.

The invention also concerns a device comprising a generator of magnetic field oscillating at the high frequency and, medium and/or low frequency, and at least one magnetic nanoparticle.

In one embodiment of the invention, the magnetic field generator generates the magnetic field oscillating at the high frequency and, medium and/or low frequency.

In still another embodiment of the invention, the device is a medical device or a combination of several medical devices, or a drug, or a combination of several drugs, or a combination of at least a medical device and at least a drug, or at least a therapeutic substance.

The invention also concerns magnetic nanoparticles for use, wherein the application of a magnetic field oscillating at the high frequency and at the medium and/or low frequency, enables reaching a distance between the device generating the oscillating magnetic field and the body part of more than 50 cm.

In one embodiment of the invention, the distance between the device generating the oscillating magnetic field and the body part is larger than 1, 10, 20, 50, 75, 100, or 1000 cm.

The invention also relates to a device suitable for magnetic hyperthermia comprising a generator of magnetic field oscillating at a high frequency and at a medium frequency and/or low frequency.

In one embodiment of the invention, the device can represent any part or combination of parts of the device generating the oscillating magnetic field including the coil, the part or generator that generates or produces the alternating current, the part that is responsible for the generation of the alternating magnetic field, the cooling system, or the power supply.

In another embodiment of the invention, the magnetic nanoparticle represents the assembly of all nanoparticles, or of less than 90, 70, 50, 25, 10, or 1% of magnetic nanoparticles administered or comprised in the body part of the individual.

In one embodiment of the invention, the distance between the device and the magnetic nanoparticle is larger than 1, 10, or 100 nm, or 1, 10, or 100 µm, or 1, 10, or 100 mm, or 1, 10, or 100 cm, or 1, 10, or 100 m.

In another embodiment of the invention, the distance between the device and the magnetic nanoparticle is smaller than 1, 10, or 100 nm, or 1, 10, or 100 µm, or 1, 10, or 100 mm, or 1, 10, or 100 cm, or 1, 10, or 100 m.

In one embodiment, the generator of magnetic field is a generator of alternating current, where the alternating current is preferentially responsible for generating the oscillating magnetic field.

According to the invention, the device has a power larger than $10^{-6}$, $10^{-4}$, $10^{-2}$, 1, 10, or $10^3$ Watt per $cm^3$ of the body part.

In one embodiment of the invention, the current, preferentially the alternating current, produced by the device is larger than 1, 10, 50, 100, 500, or 1000 A.

In one embodiment of the invention, the current, preferentially the alternating current, produced by the device is smaller than 1, 10, 50, 100, 500, or 1000 A.

In another embodiment of the invention, the power, preferentially of the power supply of the device or of the device, is larger than $10^{-6}$, $10^{-4}$, $10^{-2}$, $10^{-1}$, 1, 10, $10^2$, $10^4$, or $10^6$ KW.

In another embodiment of the invention, the power, preferentially of the power supply of the device or of the device, is smaller than $10^{-6}$, $10^{-4}$, $10^{-2}$, $10^{-1}$, 1, 10, $10^2$, $10^4$, or $10^6$ KW.

In still another embodiment of the invention, the strength or amplitude of the magnetic field, the maximum or average magnetic field, generated by the device is lower than $10^{-6}$, $10^{-4}$, $10^{-2}$, $10^{-1}$, 1, 10, $10^2$, $10^4$, or $10^6$ T.

In still another embodiment of the invention, the strength or amplitude of the magnetic field, the maximum or average magnetic field, generated by the device is higher than $10^{-6}$, $10^{-4}$, $10{-2}$, $10^{-1}$, 1, 10, $10^2$, $10^4$, or $10^6$ T.

In still another embodiment of the invention, the strength or amplitude of the magnetic field, the maximum or average magnetic field, generated by the device is smaller than $10^{-6}$, $10^{-4}$, $10{-2}$, $10^{-1}$, 1, 10, $10^2$, $10^4$, or $10^6$ T.

In still another embodiment of the invention, the strength or amplitude of the magnetic field, the maximum or average magnetic field, generated by the device is larger than $10^{-6}$, $10^{-4}$, $10^{-2}$, $10^{-1}$, 1, 10, $10^2$, $10^4$, or $10^6$ T.

According to the invention, the magnetic field can preferentially be generated at a distance from the device of more or less than 1, 10, or 100 nm, or 1, 10, or 100 µm, or 1, 10, or 100 mm, or 1, 10, or 100 cm, or 1, 10, or 100 m, where the magnetic field can preferentially be generated within more or less than $10^9$, $10^7$, $10^5$, $10^3$, $10^2$, 10, 1, $10^{-1}$, $10^{-2}$, $10^{-3}$, $10^{-5}$, $10^{-7}$, or $10^{-9}$ seconds.

In still another embodiment of the invention, the high, medium, and/or low frequency of oscillation generated by the device is smaller than $10^{-9}$, $10^{-8}$, $10^{-7}$, $10^{-6}$, $10^{-5}$, $10^{-4}$, $10^{-3}$, $10^{-2}$, $10^{-1}$, 1, 10, $10^2$, $10^3$, $10^4$, $10^5$, $10^6$, $10^7$, $10^8$, or $10^9$ Hz.

In still another embodiment of the invention, the high, medium, and/or low frequency of oscillation generated by the device is larger than $10^{-9}$, $10^{-8}$, $10^{-7}$, $10^{-6}$, $10^{-5}$, $10^{-4}$, $10^{-3}$, $10^{-2}$, $10^{-1}$, 1, 10, $10^2$, $10^3$, $10^4$, $10^5$, $10^6$, $10^7$, $10^8$, or $10^9$ Hz.

In one embodiment of the invention, the device generating a magnetic field oscillating at high and, medium and/or low frequency, enables to increase the distance between the device and the magnetic nanoparticle by a factor of 1.001, 1.01, 1.1, 1.2, 1.5, 2, 3, 5, 10, $10^2$, or $10^3$, compared with a system generating a magnetic oscillating only at high frequency.

In one embodiment of the invention, the device generating the magnetic field oscillating at high and medium frequency, enables to increase the distance between the device and the magnetic nanoparticle by a factor of 1.001, 1.01, 1.1, 1.2, 1.5, 2, 3, 5, 10, $10^2$, or $10^3$, compared with a system generating a magnetic oscillating only at high frequency.

In one embodiment of the invention, the device generating a magnetic field oscillating at high and low frequency, enables to increase the distance between the device and the magnetic nanoparticle by a factor of 1.001, 1.01, 1.1, 1.2, 1.5, 2, 3, 5, 10, $10^2$, or $10^3$, compared with a system generating a magnetic field oscillating only at high frequency.

In one embodiment of the invention, when the distance between the device and the magnetic nanoparticles is increased by a factor of 1.001, 1.01, 1.1, 1.2, 1.5, 2, 3, 5, 10, $10^2$, or $10^3$, the percentage of nanoparticle, preferentially the body part of the individual, which is exposed to the oscillating magnetic field decreases by a factor of 1.001, 1.01, 1.1, 1.2, 1.5, 2, 3, 5, 10, $10^2$, or $10^3$.

In another embodiment of the invention, the magnetic field, oscillating at the high and, medium and/or low frequency, enables to reach a higher or larger maximum magnetic field and/or to reduce the diffusion of the magnetic nanoparticles outside the body part of the individual, compared with a magnetic field, oscillating only at the high frequency. It may therefore preferentially also lead to treatment and/or heating efficacy with less than 70, 50, 30, 20, 10, 5, 2, 1, or 0.1%, of magnetic nanoparticles, preferentially in the body part of the individual, exposed to the oscillating magnetic field, or with less than 70, 50, 30, 20, 10, 5, 2, 1, or 0.1% of the body part of the individual, preferentially comprising magnetic nanoparticles, exposed to the oscillating magnetic field.

The invention also concerns a device, where the high oscillation frequency is modulated by the medium oscillation frequency, wherein the modulation enables to reach a maximum magnetic field, which is larger than the maximum magnetic field reached without modulation.

In another embodiment of the invention, the device generating a high oscillation frequency modulated by a medium oscillation frequency, enables to reach a maximum magnetic field, which is 1.001, 1.01, 1.1, 1.2, 1.5, 2, 2.5, 3, 5, 7, 10, 15, 20, 25, 30, or 50 times larger or, which is 1, 2, 5, 10, 20, 30, or 50 mT higher or larger, than the maximum magnetic field reached without modulation.

In another embodiment of the invention, the device generating the high oscillating frequency modulated by a medium oscillation frequency, enables to reach an average magnetic field, which differs by less than 1, 2, 2, 5, 10, 25, 50, 75, 85, 95% from the average magnetic field, reached without modulation, where this percentage can correspond to $[(H_{avwomod} - H_{avwmod})/H_{avwomod}]$, where $H_{avwomod}$ and $H_{avwmod}$ correspond to the average magnetic fields without and with modulation, respectively.

In another embodiment of the invention, the use of a medium oscillation frequency enables to divide by a factor of 1, 2, 5, 10, 100, or 1000 the power of the generator necessary to produce the oscillating magnetic field, which can heat the magnetic nanoparticles.

In another embodiment of the invention, the use of at least a high oscillating frequency and, a medium and/or a low oscillating frequency, enables the use of a generator, generating the alternating current, with a power lower than 200, 100, 50, 20, 10, 5, 2, or 1 kW to heat the nanoparticles.

This invention also concerns a device, such that the distance between a part of device generating the oscillating magnetic field and a body part to be treated by magnetic hyperthermia is of more than 50 cm.

In one embodiment, the part of the device generating the oscillating magnetic field is the part of the device in which the alternating current is circulating.

In one embodiment of the invention, distance increase enables to improve treatment safety, since it preferentially leads to an increased distance between the individual or the body part of the individual and the device and minimizes risks of direct contact between the device and the individual or the body part of the individual.

In one embodiment of the invention, the device generating a magnetic field oscillating at high and medium frequency, enables to increase the SAR of magnetic nanoparticles by a factor 1.001, 1.01, 1.1, 1.2, 1.5, 2, 3, 5, 10, $10^2$, or $10^3$, or to increase this SAR by more than 0.1, 1, 5, 10, 50, 100, 500, or 1000 W/$g_{Fe}$, compared to the SAR of magnetic nanoparticles measured by a system generating a magnetic field, oscillating only at high frequency.

In one embodiment of the invention, the device generating a magnetic field oscillating at high and low frequency, enables to increase the SAR of magnetic nanoparticles by a factor 1.001, 1.01, 1.1, 1.2, 1.5, 2, 3, 5, 10, $10^2$, or $10^3$, or to increase this SAR by more than 0.1, 1, 5, 10, 50, 100, 500, or 1000 W/$g_{Fe}$, compared to the SAR of magnetic nanoparticles measured by a system generating a magnetic field, oscillating only at high frequency.

In one embodiment of the invention, the device generating a magnetic field oscillating at high, medium, and low frequency, enables to increase the SAR of magnetic nanoparticles by a factor 1.001, 1.01, 1.1, 1.2, 1.5, 2, 3, 5, 10, $10^2$, or $10^3$, or to increase this SAR by more than 0.1, 1, 5, 10, 50, 100, 500, or 1000 W/$g_{Fe}$, compared to the SAR of magnetic nanoparticles measured by a system generating a magnetic field, oscillating only at high frequency, or oscillating at high and medium frequency, or oscillating at high and low frequency.

In another embodiment of the invention, the device generating a magnetic field oscillating at high and medium frequency enables to enhance treatment efficacy, i.e. to increase the number of pathological cells destroyed by the oscillating magnetic field, preferentially by a factor of more than 1.001, 1.01, 1.1, 1.2, 1.5, 2, 3, 5, 10, $10^2$, or $10^3$, or to increase the number of destroyed pathological cells, preferentially by more than 1, 10, $10^2$, $10^3$, $10^6$, $10^9$, $10^{12}$, or $10^{15}$ cells, or to increase the percentage of the part of the body part of the individual, which is destroyed, preferentially by more than 1, 2, 5, 10, 25, 50, 75, 80, or 90%, compared with the number of pathological cells or the percentage of the body part of the individual, which is destroyed, by a magnetic field oscillating only at high frequency.

In one embodiment of the invention, the percentage of the body part of the individual, which is destroyed, represents the ratio between the volume of the body part of the individual, which is destroyed, preferentially measured after application of the oscillating magnetic field, and the total volume of the body part of the individual, preferentially measured after application of the oscillating magnetic field.

In another embodiment of the invention, the increase in the number of destroyed pathological cells or in the percentage of the body part of the individual, which is destroyed, corresponds to an increase in the number of apoptotic or necrotic cells, by more than 1, 10, $10^3$, $10^6$, or $10^9$, preferentially comprised in the body part of the individual.

In another embodiment of the invention, the device generating a magnetic field oscillating at high and low frequency enables to enhance treatment efficacy, i.e. to increase the number of pathological cells destroyed by the oscillating magnetic field by a factor of more than 1.001, 1.01, 1.1, 1.2, 1.5, 2, 3, 5, 10, $10^2$, or $10^3$, or to increase the number of destroyed pathological cells by more than 1, 10, $10^2$, $10^3$, $10^6$, $10^9$, $10^{12}$, or $10^{15}$ cells, or to increase the percentage of the body part of the individual, which is destroyed, by more than 1, 2, 5, 10, 25, 50, 75, 80, 90%, compared with the number of pathological cells or the percentage of the body part of the individual, which is destroyed, by a magnetic field oscillating only at high frequency.

In another embodiment of the invention, the device generating a magnetic field oscillating at high and medium frequency enables to enhance treatment efficacy, i.e. to increase the number of pathological cells destroyed by the oscillating magnetic field by a factor of more than 1.001, 1.01, 1.1, 1.2, 1.5, 2, 3, 5, 10, $10^2$, or $10^3$, or to increase the number of destroyed pathological cells by more than 1, 10, $10^2$, $10^3$, $10^6$, $10^9$, $10^{12}$, or $10^{15}$ cells, or to increase the percentage of the body part of the individual, which is destroyed, by more than 1, 2, 5, 10, 25, 50, 75, 80, 90%, compared with the number of pathological cells or the percentage of the body part of the individual, which is destroyed, by a magnetic field oscillating only at high frequency.

In another embodiment of the invention, the device generating a magnetic field oscillating at high, medium and low frequency, enables to enhance treatment efficacy, i.e. to increase the number of pathological cells destroyed by the oscillating magnetic field by a factor of more than 1.001, 1.01, 1.1, 1.2, 1.5, 2, 3, 5, 10, $10^2$, or $10^3$, or to increase the number of destroyed pathological cells by more than 1, 10, $10^2$, $10^3$, $10^6$, $10^9$, $10^{12}$, or $10^{15}$ cells, or to increase the percentage of the body part of the individual, which is destroyed, by more than 1, 2, 5, 10, 25, 50, 75, 80, or 90%, compared with the number of pathological cells or the percentage of the body part of the individual, which is destroyed, by a magnetic field oscillating only at high frequency, or oscillating at high and medium frequency, or oscillating at high and low frequency.

The invention also relates to magnetic nanoparticles for use in a hyperthermia method of therapeutic or prophylactic treatment or of diagnosis, wherein the magnetic nanoparticles are administered to the body part of the individual and the body part is exposed to a magnetic field oscillating at low and very low frequency.

In another embodiment of the invention, a hyperthermia method of therapeutic or prophylactic treatment or of diagnosis, is a method in which magnetic nanoparticles are exposed to a radiation oscillating at the low frequency. In this method, the exposure of magnetic nanoparticles to the magnetic field preferentially induces a temperature increase and/or a movement of the nanoparticles, which preferentially lead(s) to a specific interaction and/or transformation of body part of the individual. Such specific interaction and/or transformation can be the internalization or externalization of nanoparticles in/from cells, the death of cells, preferentially by apoptosis or necrosis, where these cells preferentially belong to the body part of the individual.

DESCRIPTION OF THE TABLES

Table 1: Properties of the different coils used to generate the magnetic field, oscillating at the high, $f_h$, and medium, $f_m$, frequency for coils 1 to 5. These properties are measured at the center of each coil after 5 minutes of application of the magnetic field when the magnetic field is stabilized. The length and diameter of the different coils are indicated in cm, the strength of the alternating current within each coil is indicated in Ampere (A), the average and maximum magnetic fields, $H_{av}$ and $H_{max}$, measured at the center of each coil are indicated in mT, the ratio $H_{max}/H_{av}$ is indicated, as well as the number of turns of each coil.

Table 2: Specific absorption rate (SAR), measured in Watt per gram of iron comprised in M-PLL or BNF-Starch, for suspensions of M-PLL or BF-Starch exposed during 650 seconds to a magnetic field oscillating at $f_h$, $f_m$, $H_m$ax and $H_{av}$ values indicated in table 1 (centers of coils 1 to 5). The SAR is estimated using the relation SAR=$(C_{eau}/X_{Fe})\Delta T/\delta t$, where $C_{eau}$=4.2 J·g$^{-1}$·K$^{-1}$ is the calorific capacity of water, $X_{Fe}$=0.01 g/mL is the iron concentration of the M-PLL or BNF-Starch suspension and $\Delta T/\delta t$ is the initial slope of the temperature variation with time of the M-PLL or BNF-Starch suspension, measured in ° C./sec. Increase in temperature, $\Delta T$, after 650 seconds of the application of a magnetic field oscillating at $f_h$ and $f_m$ values, with $H_{max}$ and $H_{av}$ values indicated in table 1 (coils 1 to 5).

Table 3: Conditions of application of the oscillating magnetic field by coil 2, as a function of the distance from the edge of coil 2. The schematic diagram of FIG. 4(a) shows the two positions located at 5 cm (−5) and 8 cm (−8) from the edge of coil 2. For a distance from the edge of coil 2 of 5 cm, we have measured that $f_h$=192 kHz, $H_{max}$=13 mT, $H_{av}$=12 mT and $H_{max}/H_{av}$=1.1. For a distance from the edge of coil 2 of 8 cm, we have measured that $f_h$=189 kHz, $H_m$=5 mT, $H_{av}$=5 mT and $H_{max}/H_{av}$=1.1. The properties of the magnetic field are measured after magnetic field stabilization.

Table 4: Specific absorption rate (SAR) measured in Watt per gram of iron comprised in chemical nanoparticles (SIGMA, ref: 544884) for a suspension of chemical nanoparticles exposed during 650 seconds to a magnetic field oscillating at $f_h$ and $f_m$, with $H_{max}$ and $H_{av}$ values indicated in table 3 (coil 2). The SAR is estimated using the relation SAR=$(C_{eau}/X_{Fe})\Delta T/\delta t$, where $C_{eau}$=4.2 J·g$^{-1}$·K$^{-1}$ is the calorific capacity of water, $X_{Fe}$ is the iron concentration of the suspension of chemical nanoparticles in g/mL and $\Delta T/\delta t$ is the initial slope of the temperature variation with time of the suspension of chemical nanoparticles, measured in °

C./sec. Increase in temperature, ΔT, after 650 seconds of the application of a magnetic field oscillating at $f_h$, $f_m$, $H_{max}$, and $H_{av}$ values indicated in table 3 (coil 2). SAR and ΔT are measured for the tube containing chemical nanoparticles positioned at 5 and 8 cm from the edge of coil 2, with nanoparticle concentrations of 57, 87, 194, and 422 mg/mL in iron of nanoparticles.

Table 5: For GL-261 cells brought into contact with 2 mg of BNF-Starch in 2 mL, which are exposed to a magnetic field, oscillating at $f_h$=196 kHz, $f_m$=15 kHz, with $H_{av}$=61 mT and $H_{max}$=85 mT, applied during the heating times $t_7$ to reach 45° C. during the heating steps, and then not exposed to a magnetic field during the cooling times $t_8$ to reach 37° C. during the cooling steps (condition 4 of example 3). Heating and cooling steps are repeated 10 times. Values of $t_7$ and $t_8$, as well as $H_{av}$, $H_{max}$, and low frequencies, $f_l$, deduced from low frequency sequences are estimated for the 10 cycles.

Table 6: For GL-261 cells brought into contact with 2 mg of BNF-Starch in 2 mL, which are exposed to a magnetic field, oscillating at $f_h$=196 kHz and $f_m$=15 kHz, with $H_{av}$=61 mT and $H_{max}$=85 mT, applied during the heating times $t_7$ to reach 50° C. during the heating steps, and then not exposed to a magnetic field during the cooling times $t_8$ to reach 37° C. during the cooling steps (condition 7 of example 3). Heating and cooling steps are repeated 6 times. Values of $t_7$ and $t_8$, as well as $H_{av}$, $H_{max}$, and low frequencies, $f_l$, deduced from low frequency sequences are estimated for the 6 cycles.

Table 7: For GL-261 cells brought into contact with 2 mg of BNF-Starch, which are exposed to a magnetic field, oscillating field at $f_h$=196 kHz and $f_m$=15 kHz, with $H_{av}$=61 mT and $H_{max}$=85 mT, applied during the heating time $t_7$ to reach 55° C. during the heating steps, and then not exposed to a magnetic field during the cooling times $t_8$ to reach 37° C. during the cooling steps (condition 10 of example 3). Heating and cooling steps are repeated 4 times. Values of $t_7$ and $t_8$, as well as $H_{av}$, $H_{max}$, and low frequencies, $f_l$, deduced from low frequency sequences are estimated for the 4 cycles.

Table 8: A suspension containing 25 μg in iron of BNF-Starch per mm³ of tumor is administered to subcutaneous glioblastoma GL-261 tumors of 60 to 90 mm³ and exposed to 21 hyperthermia sessions during which a magnetic field, oscillating at $f_h$=202 kHz and $f_m$=15 kHz, with $H_{av}$=27 mT and $H_{max}$=57 mT is first applied during a heating time $t_7$ to reach a temperature of 39-47° C. during the heating steps and then not applied during the cooling times $t_8$ to reach a temperature of 34-37° C. during the cooling times. During each of the 21 hyperthermia sessions, there are between 4 and 86 low frequency cycles. Values of $t_7$ and $t_8$, as well as $H_{av}$, $H_{max}$, and low frequencies, $f_l$, deduced from low frequency sequences are estimated for the different cycles.

Table 9: A suspension containing 25 μg in iron of BNF-Starch per mm³ of tumor is administered to subcutaneous glioblastoma GL-261 tumors of 60 to 90 mm³ and exposed to 15 hyperthermia sessions during which a magnetic field, oscillating at $f_h$=202 kHz and $f_m$=15 kHz, with $H_{av}$=24-31 mT and $H_{max}$=54-67 mT is applied continuously during to reach a temperature of 37-47° C. during each hyperthermia session.

EXAMPLES

Example 1: Application of a Magnetic Field, Oscillating at High and Medium Frequencies, $f_h$ and $f_m$, to Heat Nanoparticles A volume of 100 µL of a suspension containing either nonpyrogenic magnetosomes coated with poly-L-lysine, also designated as central parts of magnetosomes coated with poly-L-lysine or magnetosome minerals coated with poly-L-lysine, (M-PLL) or BNF-Starch (Micromod, ref: 10-00-801) at a concentration of 10 mg/mL in iron was introduced into a 250 µL tube. The preparation, characterization and properties of M-PLL have been described in Patent PCT/FR2016/000095 which is incorporated herein by reference. The tube was placed at the center of each of the 5 induction coils, whose properties are summarized in table 1. Each coil was connected to a power source generating an alternating current of intensity varied between 73 and 682 A (Easy Heat 10 kW, Ambrell) to obtain the same $H_{av}$, where the alternating current produced an oscillating magnetic field during 700 sec. The temperature variation inside the tube, following the application of the alternating magnetic field, was measured using a thermocouple (IT-18, Physitemp). The measurement of the alternating magnetic field was carried out using a magnetic probe placed at the center of each induction coil (Magnetic field probe, AMF life system), and an oscilloscope. The probe measured the variation with time of the axial voltage, $U_a$, and of the radial voltage, $U_r$. We deduced from $U_a$ and $U_r$ the variation of the magnetic flux density over time in the radial direction, $H_r=U_r/[0.7f_h]$, and in the axial direction, $H_a=U_a/[0.6f_h]$, where $f_h$ is the high frequency of oscillation. We also deduced the variation of the magnitude of magnetic flux density with time using the relation: $H=[(H_a)^2+(H_r)^2]^{1/2}$.

With the probe, we measured the variation of the magnetic flux density in the axial and radial directions, as well as the magnitude of the magnetic flux density, during $650\ 10^{-6}$ seconds, with a magnetic field measurement carried out every $0.16\ 10^{-6}$ seconds. The average and maximum magnetic fields, $H_{av}$ and $H_{max}$, were estimated, taking into accounts the maximum values of the amplitude of the magnetic field of each high frequency oscillation, $H_{max,i}$, during a measurement time of $650\ 10^{-6}$ seconds.

Figure 1:
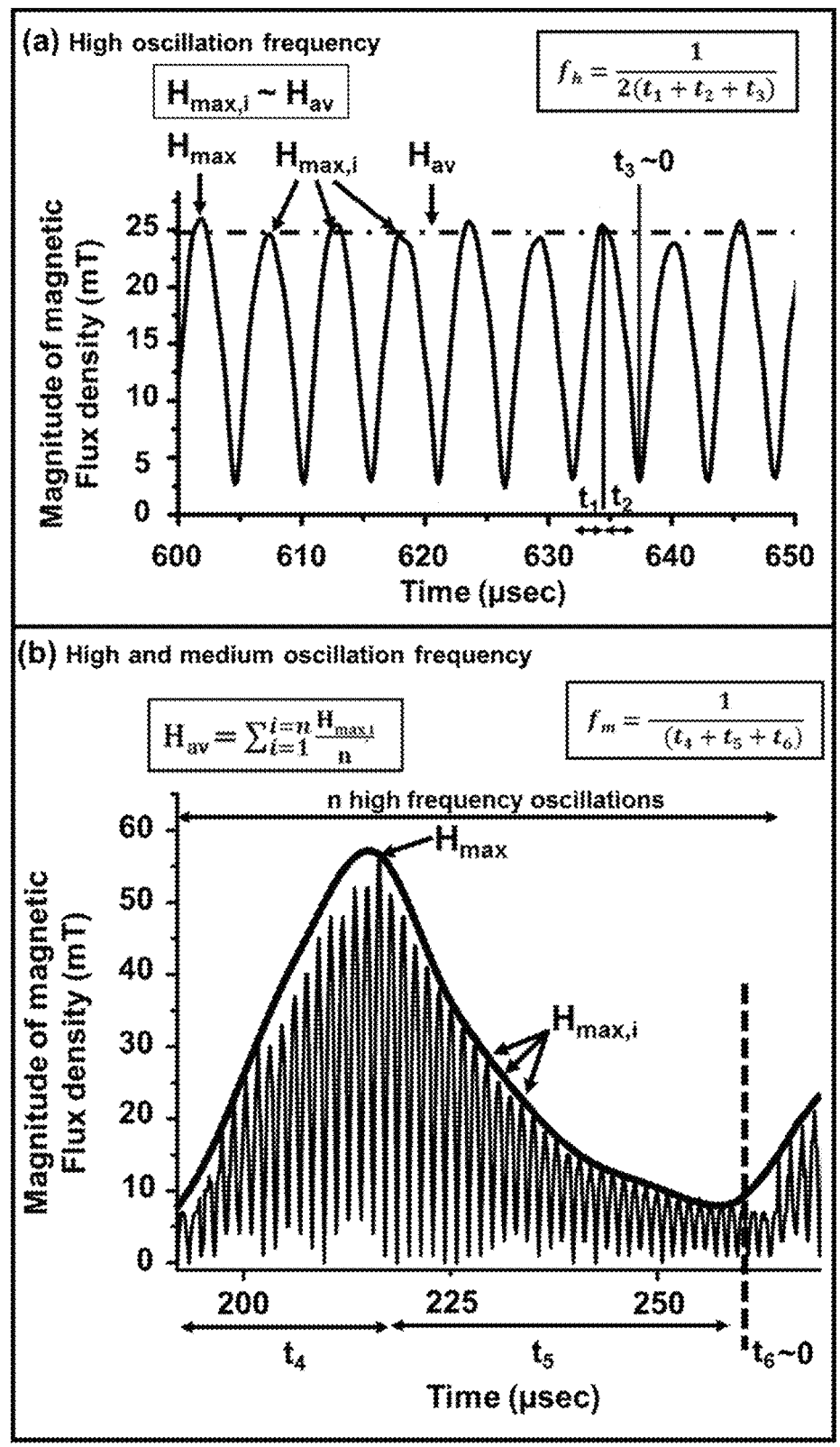
FIG. 1: (a), for a magnetic field oscillating only at a high frequency, $f_h$, variation of the magnitude of magnitude flux density with time, with indications of time $t_1$ during which the magnetic field amplitude increases, time $t_2$ during which the magnetic field amplitude decreases, time $t_3$ during which the magnetic field is constant, with indication of $H_{max}$ corresponding to the maximum magnetic field amplitude among the different values of $H_{max,i}$, where $H_{max,i}$ corresponds to the local maximum of magnetic field amplitude at each high frequency oscillation. $f_h$ may be equal or proportional to $1/[2(t_1+t_2+t_3)]$. (b), for a magnetic field oscillating at a high frequency, $f_h$, and a medium frequency, $f_m$, which may be equal or proportional to $1/[(t_4+t_5+t_6)]$, variation of the magnitude of magnetic flux density with time, with indications of time $t_4$ during which the magnetic field amplitude increases, time $t_5$ during which the magnetic field amplitude decreases, time $t_6$ during which the magnetic field is constant, with indication of $H_{max}$ corresponding to the maximum magnetic field amplitude among different values of $H_{max,i}$, where $H_{max,i}$ corresponds to the local maximum of magnetic field amplitude at each high frequency oscillation and $H_{av}$ is equal or proportional to $(\Sigma_{i=1}^{i=n} H_{max,i})/n$, where n is the number of high frequency oscillations.

For a magnetic field oscillating only at high frequency, the variation with time of the magnetic field amplitude is shown in FIG. 1(a), while for a magnetic field oscillating at high and medium frequency, the variation with time of the magnetic field amplitude is shown in FIG. 1(b). For coils 1 to 4, the medium frequency of $f_m=15$ kHz corresponds to a period $T_m=1/f_m=67\ 10^{-6}$ seconds, which is much smaller than the measurement time and $f_m$ can hence be measured for coils 1 to 4. For coil 5, the medium frequency $f_m=2$ kHz corresponds to a period $T_m=1/f_m=500\ 10^{-6}$ seconds, which is also smaller than the measurement time and $f_m$ can hence be measured for coil 5.

Figure 2:
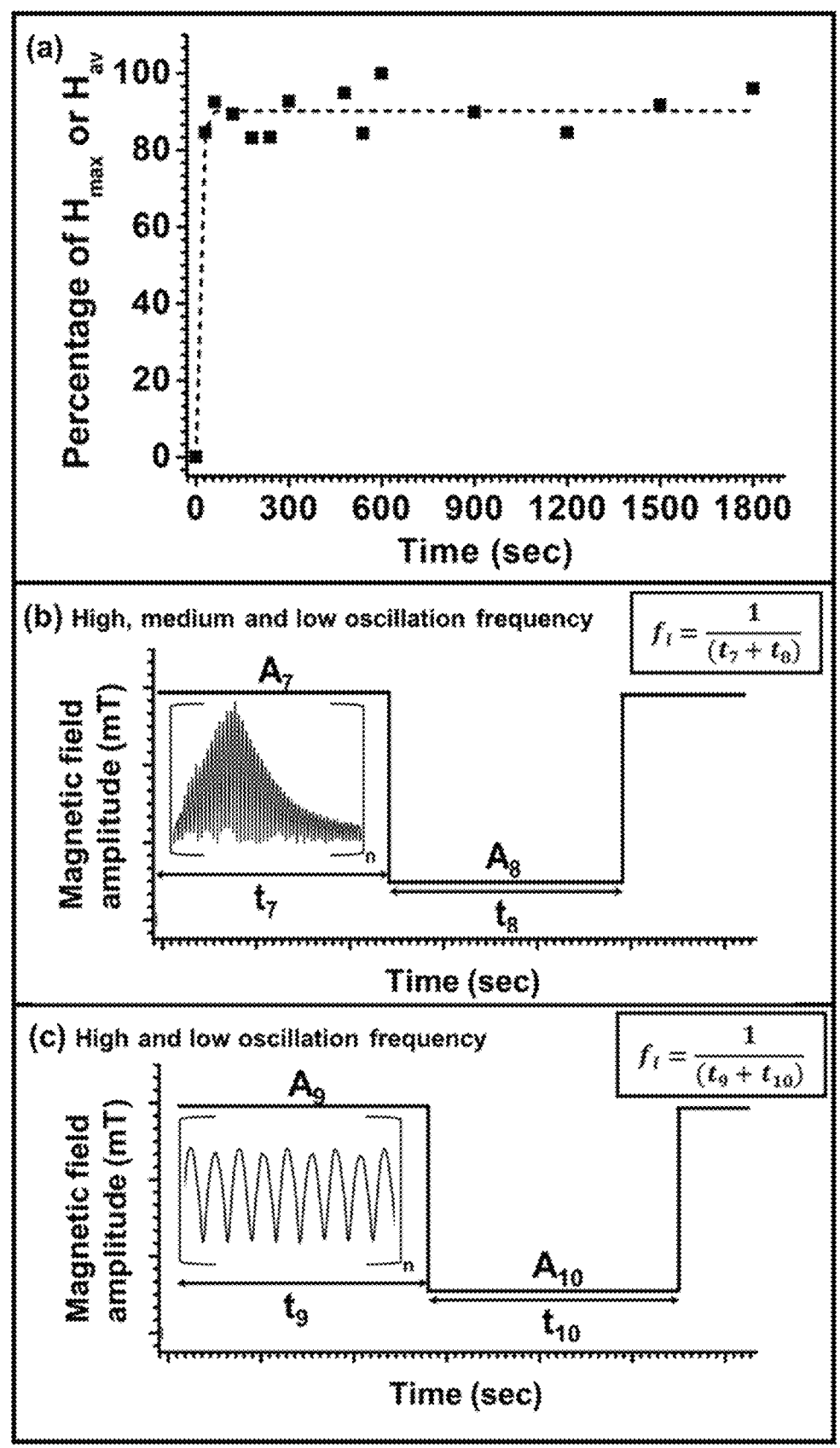
FIG. 2: (a), Percentage of $H_{max}$ and $H_{av}$ μs a function of time following the switching on of coil 2 working with an alternating current I of 195 A. Similar curves were obtained for coil 1 at I equal to 50, 100, 150, 200, 250, 300, 350, 400 A, and for coil 2 at I equal to 50, 100, 150, 200, 250, 300, 350, 400, or 450 A, and for coil 3 at I equal to 25, 50, 100, 150, or 200 A, and for coil 4 at I equal to 25, 50, 100, 150, 200, or 250 A. (b), for a magnetic field oscillating at high, medium, and low frequency, variation of magnetic field amplitude as a function of time, showing the $A_7$ low frequency sequence, taking place during $t_7$ and corresponding to the heating step, followed by the $A_8$ low frequency sequence, taking place during $t_8$ and corresponding to the cooling step. $f_l$ may be equal or proportional to $1/(t_7+t_8)$. (c), for a magnetic field oscillating at high, and low frequency, variation of magnetic field amplitude as a function of time, showing the $A_9$ low frequency sequence, taking place during $t_9$ and corresponding to the heating step, followed by the $A_{10}$ low frequency sequence, taking place during $t_{10}$ and corresponding to the cooling step. $f_l$ may be equal or proportional to $1/(t_9+t_{10})$.

For coil 2, FIG. 2(a) shows the percentage of $H_{max}$ and $H_{av}$ reached as a function of time following the switching on of the device generating the oscillating magnetic field. It appears that 100% of $H_{max}$ and $H_{av}$, corresponding to a stable magnetic field, is reached 30 seconds after the device generating the oscillating magnetic field has been switched on. For the other coils (1, 3, 4), a stabilized magnetic field was also reached after 30 seconds and stabilization time was always observed to be below 30 seconds.

FIG. 2(b) shows the variation of the magnetic field amplitude as a function of time for a magnetic field oscillating at high, medium, and low frequency, with indications about $A_7$ and $A_8$ low frequency sequences. FIG. 2(c) shows the variation of the magnetic field amplitude as a function of time for a magnetic field oscillating at high and low frequency, with indications about $A_9$ and $A_{10}$ low frequency sequences.

Figure 3:
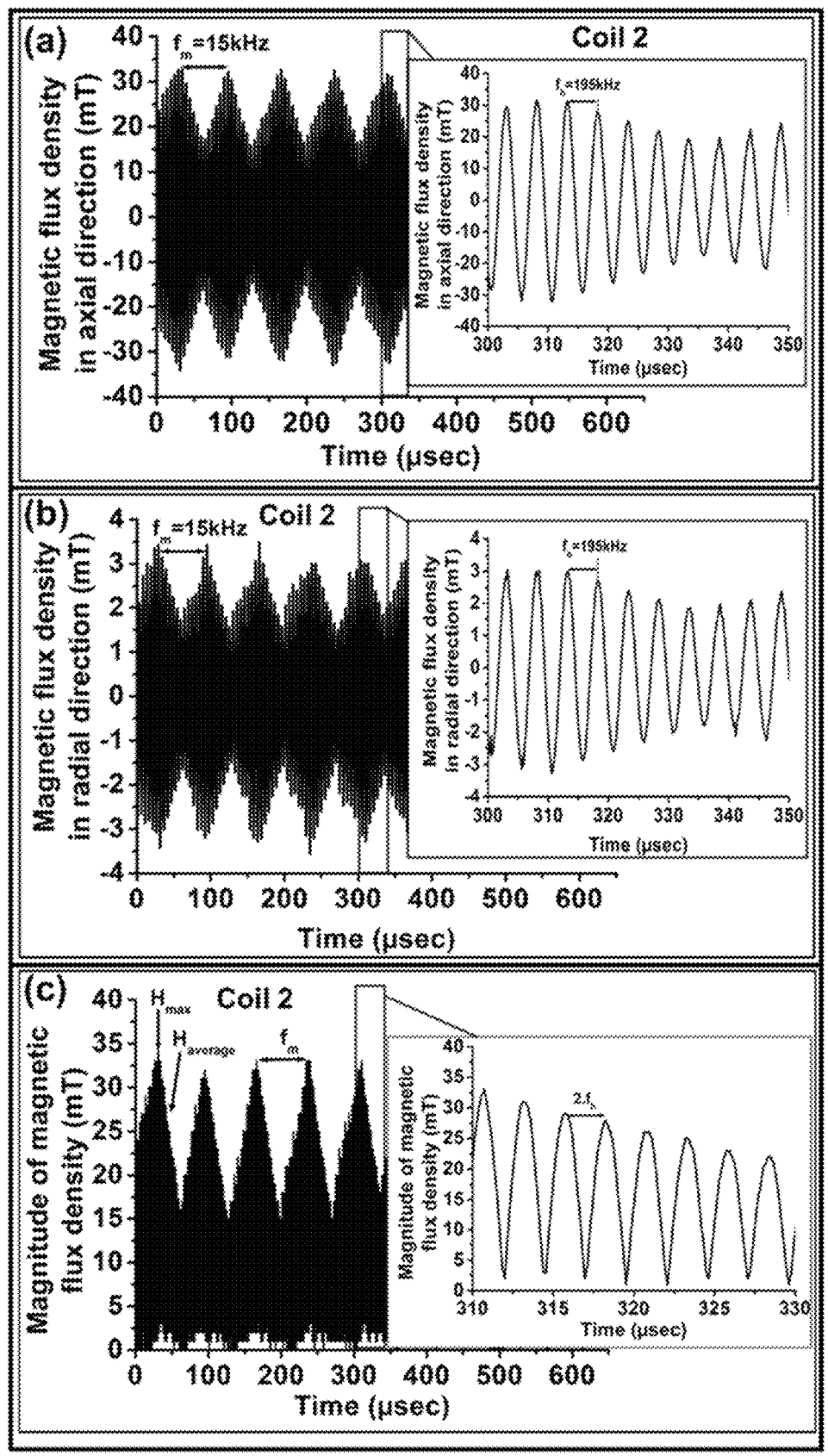
FIG. 3: (a), Variation of the magnetic flux density in axial direction as a function of time, showing both the high oscillation frequency, $f_h$=195 kHz, and the medium oscillation frequency, $f_m$=15 kHz. (b), Variation of the maximal flux density in the radial direction as a function of time, showing both the high oscillation frequency, $f_h$=195 kHz, and the medium oscillation frequency, $f_m$=15 kHz. (c), Magnitude of magnetic flux density as a function of time, showing both twice the high oscillation frequency, $2 \cdot f_h$=390 kHz, and the medium oscillation frequency, $f_m$=15 kHz. $H_{max}$ corresponds to the maximum value of the magnitude of magnetic flux density among the different values of $H_{max,i}$, where $H_{max,i}$ is the maximum magnitude of magnetic flux density estimated for each high frequency oscillation. $H_{av}$ corresponds to the average value among all values of $H_{max,i}$. The magnetic flux density, also designated as the strength of the magnetic field, is measured in the radial and axial direction of the cylindrical probe, where the probe is positioned so that its axial direction is parallel to the main magnetic field generated by coil 2. This is the reason why the strength of the magnetic field in the axial direction is much higher or larger than that in the radial direction. The magnitude of magnetic flux density is also designated as the amplitude of the magnetic field.

FIGS. 3(a), 3(b), and 3(c), show variations with time of the magnetic flux density in the axial direction (FIG. 3(a)), the variation with time of the magnetic flux density in the radial direction (FIG. 3(b)), the variation with time of the magnitude of magnetic flux density (FIG. 3(d)), measured for coil 2.

For coils 1 to 5, magnetic fields oscillate at $f_h=202$ kHz (coil 1), $f_h=195$ kHz (coil 2), $f_h=231$ kHz (coil 3), $f_h=329$ kHz (coil 4), $f_h=91$ kHz (coil 5), and $f_m=15$ kHz (coils 1 to 4) or $f_m=2$ kHz (coil 5), where these frequencies are measured as described in FIGS. 1(a) and 1(b).

The maximum magnetic field, $H_{max}$, corresponding to the maximum value of magnetic field amplitude among the different $H_{max,i}$, $$H_{max} = \underset{i=1,n}{\text{MAX}}\ H_{max,i},$$

where $H_{max,i}$ is the maximum magnetic field amplitude of each high frequency oscillation and n is the number of oscillations considered in the measurement. $H_{max}$ is equal to $H_{max}=58$ mT for an alternating current of intensity, I, of 190 A (coil 1), $H_{max}=34$ mT for I=195 A (coil 2), $H_{max}=53$ mT for I=73 A (coil 3), $H_{max}=56$ mT for I=149 A (coil 4), $H_{max}=33$ mT for 1=682 A (coil 5) (table 1).

The average magnetic field, $H_{av}$, which is estimated using the formula: $H_{av}=(\Sigma_{i=1}^{i=n}H_{max,i})/n$, is $H_{av}=26$ mT for I=190 A (coil 1), $H_{av}=25$ mT for I=195 A (coil 2), $H_{av}=26$ mT for I=73 A (coil 3), $H_{av}=24$ mT for I=149 A (coil 4), $H_{av}=26$ mT for 1=682 A (table 1).

In this experiment, we have used a value of the alternating current for each coil that yields similar average magnetic fields.

Coils 2 and 5 produce a ratio $H_{max}/H_{av}=1.3-1.4$, which is close to 1 (table 1).

Coils 1, 3, and 4, produce a higher or larger ratio $H_{max}/H_{av}$ of 2-2.3 (table 1).

By using a double coil (coil 3) with a diameter about 2 times smaller than that of the single coil 1, the current required to reach a relatively similar high frequency $f_h$ ($f_h=231$ kHz for coil 3 compared to $f_h=202$ kHz for coil 1), similar maximum and average magnetic fields, is 2.6 times lower (table 1).

For coil 4, the diameter and length are smaller than for coil 1, leading to a high oscillation frequency, which is higher or larger (329 kHz for coil 4 compared with 202 kHz for coil 1). Maximum and average fields are similar at 56-58 mT and 24-26 mT for coils 1 and 4 (table 1).

For coil 5, the diameter and length are significantly larger than for the other coils at 28 and 15 cm, respectively, and the medium and high oscillation frequencies are smaller at $f_m=2$ kHz and $f_h=91$ kHz (table 1).

Figure 5:
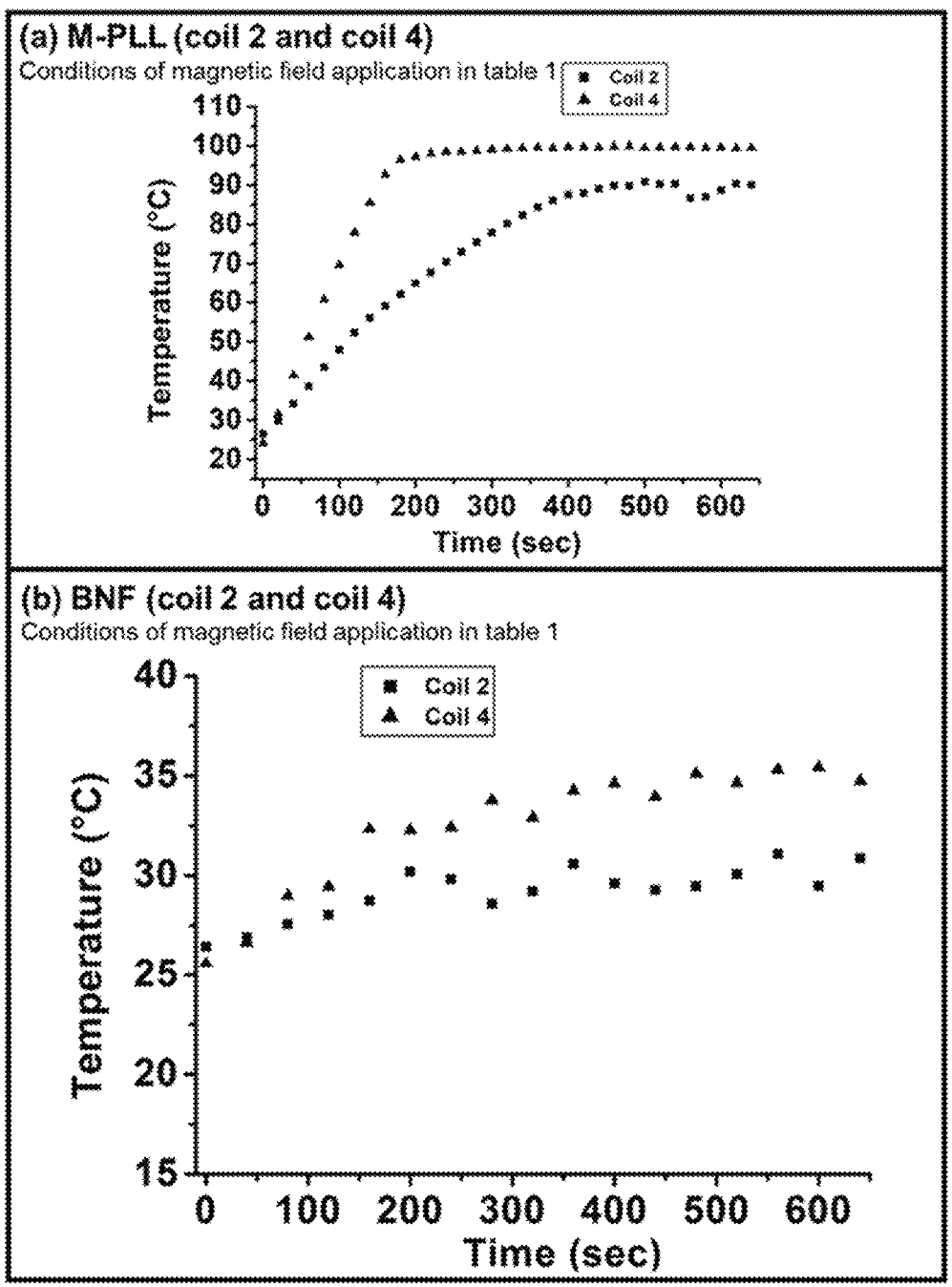
FIG. 5: Temperature variation as a function of time of a suspension of 100 µl of M-PLL, (a), or BNF-Starch, (b), at a concentration of 10 mg/mL, exposed to oscillating magnetic fields generated by coils 2 and 4 according to conditions ($H_{av}$, $H_{max}$, $f_m$, $f_h$) mentioned in table 1.

Heating properties of M-PLL suspensions and BNF-Starch exposed to the oscillating magnetic fields generated by coils 1 to 5 for M-PLL and by coils 2 and 4 for BNF-Starch have also been studied. Variations of temperature with time of 100 µL of a M-PLL or BNF-Starch suspension at 10 mg/mL are presented in FIGS. 5(a) and 5(b) when these two suspensions are exposed to the alternating magnetic field generated by coil 2 (I=195 A, $H_{max}=34$ mT, $H_{av}=25$ mT) and coil 4 (1=149 A, $H_{max}=56$ mT, $H_{av}=24$ mT). The specific absorption rate, SAR, of M-PLL and BNF-Starch suspensions was measured, using the relationship: $SAR=(C_{eau}/X_{Fe})(\Delta T/\delta t)$, where the SAR is measured in Watt per gram of iron, $C_{eau}=4.2$ J·g$^{-1}$·K$^{-1}$ is the calorific capacity of water, $X_{Fe}=0.01$ g/mL is the iron concentration of the M-PLL or BNF-Starch suspension and $\Delta T/\delta t$ is the initial slope of the temperature variation with time, measured in ° C./sec. Temperature variation, indicated by $\Delta T$, is calculated by subtracting: 1) the temperature reached by the M-PLL or BNF-Starch suspension after 650 seconds of application of the oscillating field by 2) the temperature measured before application of the oscillating magnetic field.

For M-PLL, the results of table 2 show that the induction coils which produce the highest SAR of 192-244 W/g$_{Fe}$ and ΔT of 68-75° C., are coils 1, 3 and 4, which generate the oscillating magnetic field with the highest values of maximum magnetic field of 53-58 mT and highest value of $H_{max}/H_{av}$ of 2-2.3. In contrast, the induction coils, which produce the lowest SAR of 6-84 $W/g_{Fe}$ and ΔT of 5-57° C., are coils 2 and 5, which produce the lowest values of maximum magnetic field of 33-34 mT and $H_{max}/H_{a}v$ of 1.3-1.4. Furthermore, coil 5 which generates maximum and average magnetic field of 33 mT and 26 mT, respectively, similar to that of coil 2 of 34 mT and 35 mT, respectively, but has lower $f_h$ and $f_m$ values ($f_h$=91 kHz and $f_m$=2 kHz for coil 5 compared with $f_h$=195 kHz and $f_m$=15 kHz for coil 2), leading to SAR and ΔT, which are more than 10 to 14 times lower for coil 5 than those of coil 2 (table 2).

For BNF-Starch, the results of table 2 show that the induction coils which produce the highest SAR of 13 $W/g_{Fe}$ and ΔT of 12° C., is coil 4, which generate the oscillating magnetic field with the highest values of maximum magnetic field of 56 mT and highest value of $H_{max}/H_{av}$ of 2.3. In contrast, the induction coil, which produces the lowest SAR of 8 $W/g_{Fe}$ and ΔT of 7° C. is coil 2, which produce the lowest values of maximum magnetic field of 34 mT and $H_{max}/H_{av}$ of 1.4. Moreover, BNF-Starch produce much lower SAR and ΔT than the M-PLL, both for coils 2 and 4, which can be explained by their lower coercivity, $H_c$ are 10 mT to BNF-starch and 6 mT for M-PLL, and lower ratio between remanent and saturating magnetization, $M_r/M_s$ are equal to 0.19 for M-PLL and 0.15 for BNF starch.

We can Conclude from this Example that:

i), Best heating properties, i.e. highest values of SAR and ΔT, are obtained for coils 1, 3 and 4, with the highest maximum magnetic field of 55±3 mT and the highest ratio $H_{max}/H_{av}$ of 2-2.3, suggesting that the maximum magnetic field and/or $H_{max}/H_{av}$ should be maximized in order to reach best nanoparticle heating properties under the application of an oscillating magnetic field.

ii), It is possible to obtain similar heating properties, i.e. similar values of SAR and ΔT, with similar values of $H_{max}$=55±3 mT and the highest ratio $H_{max}/H_{av}$ of 2-2.3, (coils 1, 3, 4), suggesting that $H_{max}$=55±3 mT and $H_{max}/H_{av}$ could be modified or adjusted to yield the desired heating properties.

iii), It is possible to obtain similar heating properties, i.e. similar values of SAR and ΔT, with coils of different diameters, coil number, and coil length (coils 1, 3, 4), suggesting that coil diameter, coil number, and coil length, could be modified or adjusted without necessarily modifying heating properties.

iv), For coils generating similar values of $H_{max}$ and $H_{max}/H_{av}$ (coils 2 and 5), better heating properties, i.e. higher or larger values of SAR and ΔT, are obtained for the coil with the highest $f_m$ and $f_h$ values (coil 2), suggesting that $f_m$ and/or $f_h$ should be maximized in order to reach best nanoparticle heating properties under the application of an oscillating magnetic field.

v) M-PLL lead to better heating properties than BNF-Starch both for coils 2 and 4, indicating that nanoparticle magnetic properties such as $H_c$ and $M_r/M_s$ should be maximized to reach best heating properties under the application of a magnetic field oscillating at high and medium frequency.

vi) The maximum and/or average magnetic field applied to heat M-PLL or BNF-Starch is larger than the coercivity of the nanoparticles ($H_c$=10 mT for BNF-Starch and $H_c$=6 mT for M-PLL at room temperature), which should enable rotation of the magnetic moment of the nanoparticles by application of the alternating magnetic field.

Example 2: Application of an Oscillating Magnetic Field to Heat Nanoparticle Suspensions Outside of the Coil 100 μL of a suspension containing uncoated iron oxide nanoparticles (SIGMA-ALDRICH, reference 544884) at different concentrations (422, 194, 87 and 57 mg/mL in iron) were introduced into a tube of 250 μL. The tube was then positioned at 5 cm and 8 cm from the edge of coil 2. The positions of the tube are indicated by −5 and −8 in the schematic diagram (FIG. 4(a). The tube was exposed to a magnetic field using the Ambrell Easy Heat LI 10 KW that generates an alternating current of 500 A for 1500 sec. The variation of temperature of the tube containing the nanoparticles was measured using a thermocouple (IT-18, Physitemp) while the properties of the magnetic field were measured using a magnetic probe (AMF life system) and an oscilloscope.

Figure 4:
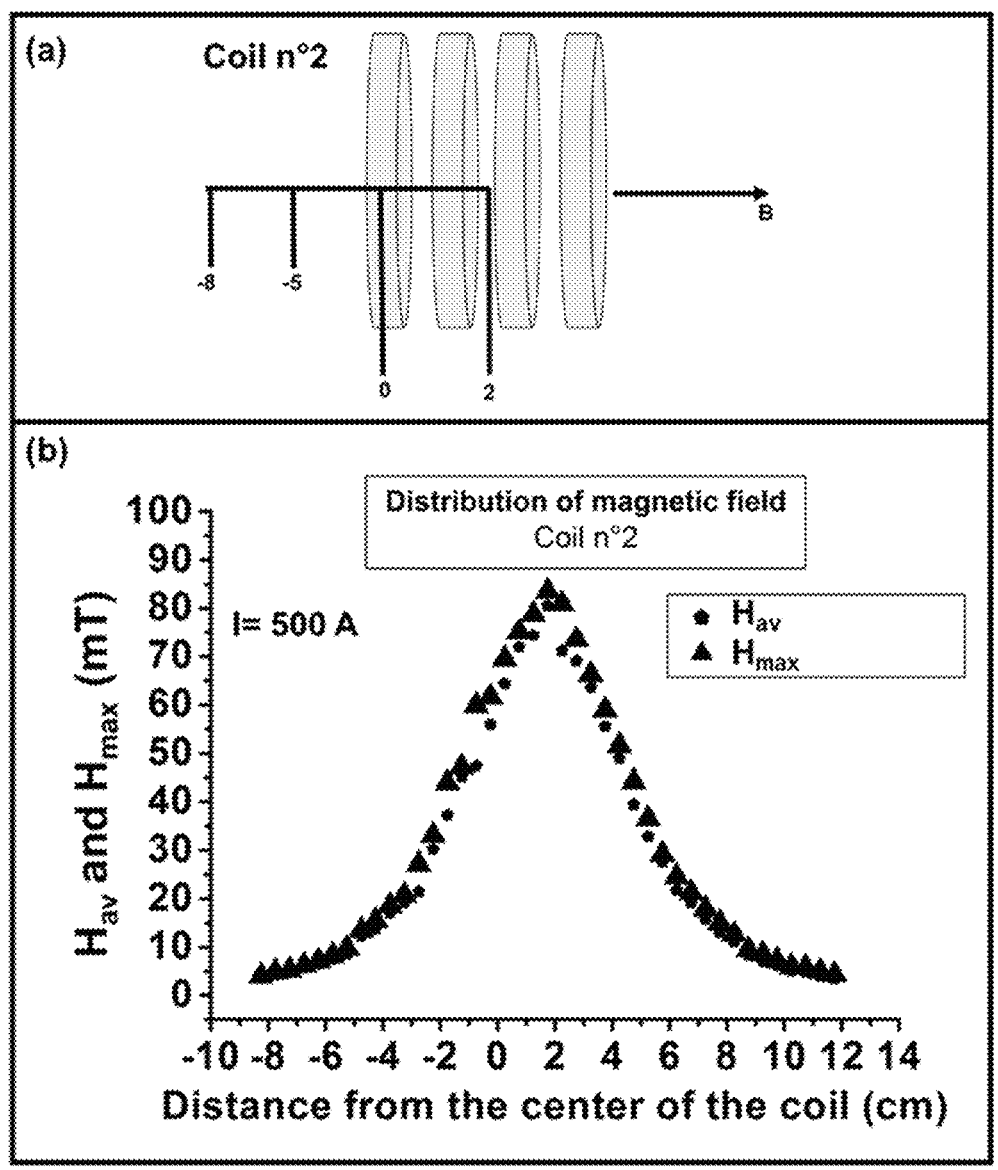
FIG. 4: Positioning of the probe used to measure the strength or amplitude of the magnetic field in coil 2, as a function of the distance from the edge of coil 2, (0), measured in cm. (b), Measurement of $H_{max}$ and $H_{av}$ as a function of the distance, measured from the center of coil 2, using an alternating current of 500 A, where 1.5 cm corresponds to the center of the coil and 0 to the edge of the coil as indicated in (a).

We measured the variation of the average, $H_{av}$, and maximum, $H_{max}$, magnetic field as a function of the distance from the edge of coil 2, designated as 0 in FIG. 4(a). FIG. 4(b) shows similar variations of $H_{max}$ and $H_{av}$ as a function of the distance from the center, 1.5 cm, of the coil. As can be seen in FIG. 4(b), the average and maximum magnetic fields decrease exponentially outside of coil 2, but are non-negligible up to 6 cm outside of the coils and could hence potentially be used to heat nanoparticles. Outside of the center of coil 2, the magnetic field appears to be "evanescent", or is characterized by a magnitude or frequency of oscillation, preferably lower than those measured at the center or inside the coil (table 3).

Table 3 shows that the magnetic field oscillates at $f_h$=192 kHz at 5 cm from the edge of coil 2 and at $f_h$=189 kHz at 8 cm from the edge of coil 2. A medium frequency could not be detected for a measurement time of 650 $10^{-6}$ seconds. In addition, the average and maximum magnetic fields are about two times lower at 8 cm from the edge of the coil ($H_{av}$=$H_{max}$=5 mT) than at 5 cm from the edge of the coil ($H_{av}$=$H_{max}$=12-13 mT), table 3.

The SAR and ΔT of chemical nanoparticles (SIGMA-ALDRICH, reference 544884) were estimated for a tube containing 100 μL of these nanoparticles, positioned at 8 cm and 5 cm from the edge of coil 2, and exposed to the magnetic field, oscillating at $f_h$=189-192 kHz with $H_{max}$ and $H_{av}$ indicated in table 3. When the tube containing the nanoparticles suspension was positioned at 8 cm from the edge of coil 2, table 4 indicates that SAR and ΔT values are low at 0.4-0.6 $W/g_{Fe}$ and 1-8° C., respectively, which can be explained by the fact that the average and maximum magnetic fields are small at 5 mT (table 3). When the tube containing the nanoparticles suspension was positioned 5 cm from the edge of coil 2, SAR and ΔT values were higher or larger at 2-3 $W/g_{Fe}$ and 13-45° C., respectively, explained by the fact that the maximum and average magnetic fields are larger at 12-13 mT, respectively (table 3).

It is therefore possible to heat a suspension of nanoparticles by positioning the tube containing a suspension of nanoparticles outside of coil 2, at 5 cm from the edge of this coil, by applying an oscillating magnetic field with maximum magnetic field larger than 10 mT.

Example 3: Application of a Magnetic Field Oscillating at a Low Frequency, $f_l$, a Medium Frequency, $f_m$, and a High Frequency, $f_h$, for the Destruction of Tumor Cells In Vitro Description of the Various Treatments:

500,000 GL-261 cells were seeded in petri dishes containing a culture medium composed of 1.6 ml of RPMI and 0.4 ml of calf serum. After incubation for 12 hours at 37° C. in the presence of 5% $CO_2$, the cells adhered to the surface of the Petri dishes and were confluent. For the application of the oscillating magnetic field, coil 2 was used.

The Following 11 Conditions of Treatment were Tested:

Condition 1:

Confluent GL-261 cells were brought into contact with the culture medium and incubated at 37° C. for 12 hours.

Condition 2:

Confluent GL-261 cells were brought into contact with the culture medium, exposed to a magnetic field, oscillating at high frequency $f_h$=196 kHz and medium frequency $f_m$=15 kHz, with $H_{av}$=61 mT and $H_{max}$=85 mT, applied continuously during 30 minutes.

Condition 3:

Confluent GL-261 cells were brought into contact with culture medium and 2 mg of BNF-Starch in iron and were then exposed to a magnetic field, oscillating at $f_h$=196 kHz and $f_m$=15 kHz, with average magnetic field varied between 49 and 61 mT and maximum magnetic field varied between 68 and 85 mT, to reach an average temperature of 45° C. during 30 minutes continuously.

Figure 6:
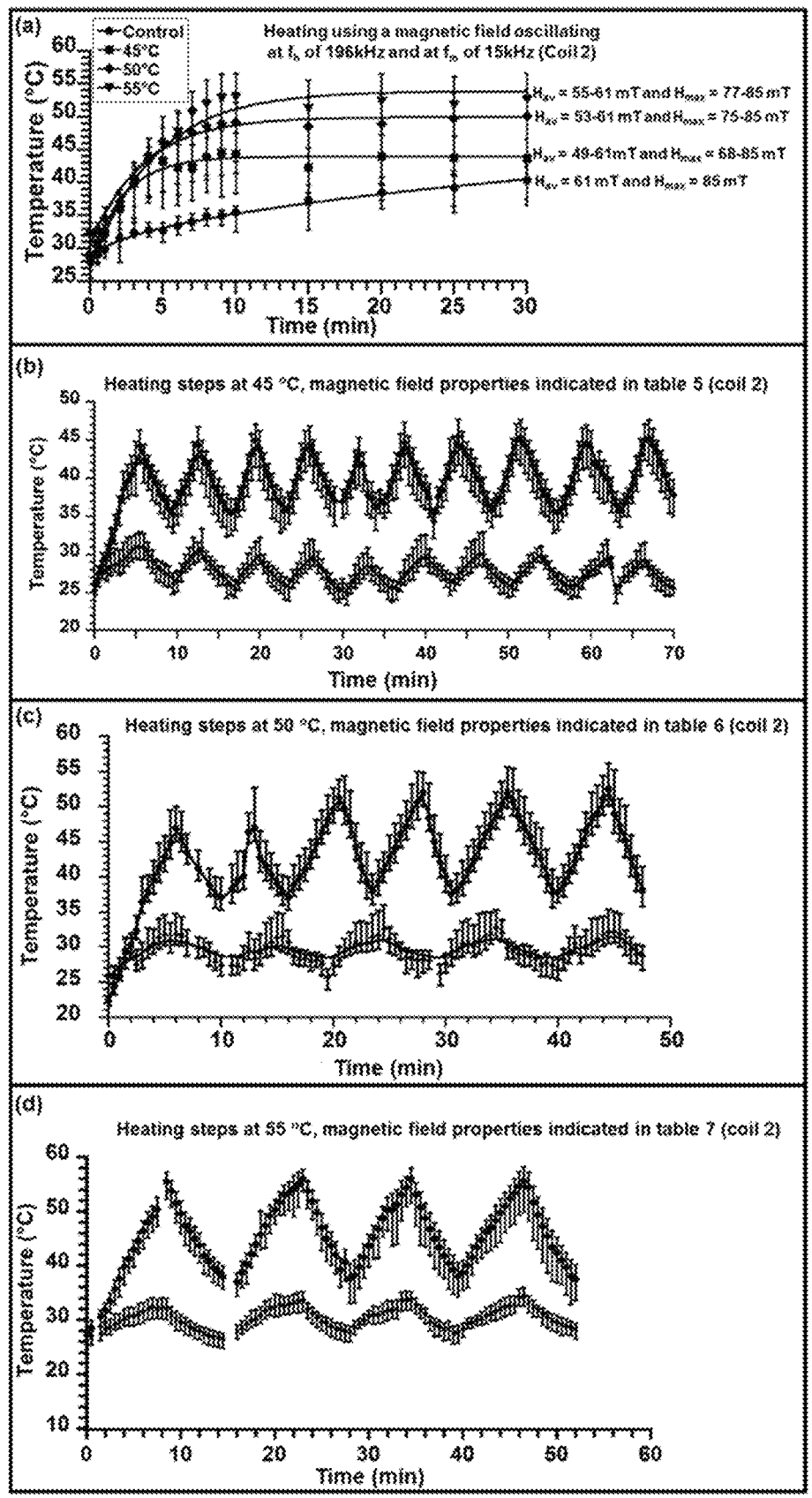
FIG. 6: (a), Temperature variation as a function of time of confluent GL-261 cells brought into contact with 2 mg of BNF-Starch in 2 mL, exposed during 30 minutes to a magnetic field, oscillating at $f_h$=196 kHz and $f_m$=15 kHz, of fixed $H_{av}$=61 mT and $H_{max}$=85 mT, (-●-), of $H_{av}$=49-61 mT and $H_{max}$=68-85 mT to reach 45° C., (-■-), of $H_{av}$=53-61 mT and $H_{max}$=75-85 mT to reach 50° C., (-◆-), of $H_{av}$=55-61 mT and $H_{max}$=77-85 mT to reach 55° C., (-▼-). In the control, confluent GL-261 cells were exposed to a magnetic field, oscillating at $f_h$=196 kHz and $f_m$=15 kHz, and of $H_{av}$=61 mT and $H_{max}$=85 mT. (b), Upper curve, temperature variation as a function of time of GL-261 cells brought into contact with 2 mg of BNF-Starch in 2 mL, exposed to sequences of application of the magnetic field, oscillating at $f_h$=196 kHz and $f_m$=15 kHz, $H_{av}$=61 mT and $H_{max}$=85 mT, corresponding to heating steps, followed by sequences of non-application of the magnetic field, corresponding to cooling steps. The heating times, $t_7$, correspond to those necessary to reach 45° C., while the cooling times, $t_8$, correspond to those necessary for the temperature to decrease from 45° C. to 35° C. In this case, the oscillating magnetic field oscillates at a low frequency of 1.6-2.5 $10^{-3}$ Hz. Bottom curve, temperature variation as a function of time for GL-261 cells without BNF-Starch exposed to the same sequences of application and non-application of the magnetic field as for the upper curve. (c), Upper curve, temperature variation as a function of time of GL-261 cells brought into contact with 2 mg of BNF-Starch in 2 mL, exposed to sequences of application of the magnetic field, oscillating at $f_h$=196 kHz, $f_m$=15 kHz, $H_{av}$=61 mT and $H_{max}$=85 mT, corresponding to heating steps, followed by sequences of non-application of the magnetic field, corresponding to cooling steps. The heating times, $t_7$, correspond to those necessary to reach 50° C., while the cooling times, $t_8$, correspond to those necessary for the temperature to decrease from 50° C. to 37° C. In this case, the magnetic field oscillates at a low frequency of 1.2-1.7 $10^{-3}$ Hz. Bottom curve, temperature variation as a function of time for GL-261 cells without BNF-Starch exposed to the same sequences of application and non-application of the magnetic field as for the upper curve. (d), Upper curve, temperature variation as a function of time for GL-261 cells brought into contact with 2 mg of BNF-Starch in 2 mL, exposed to sequences of application of the magnetic field, oscillating at $f_h$=196 kHz and $f_m$=15 kHz, $H_{av}$=61 mT and $H_{max}$=85 mT, corresponding to heating steps, followed by sequences of non-application of the magnetic field, corresponding to cooling steps. The heating times, $t_7$, correspond to those necessary to reach 55° C., while the cooling times, $t_8$, correspond to those necessary for the temperature to decrease from 55° C. to 37° C. In this case, the magnetic field oscillates at a low frequency of 0.9-1.1 $10^{-3}$ Hz. Bottom curve, temperature variation as a function of time for GL-261 cells without BNF-Starch exposed to the same sequences of application and non-application of the magnetic field as for the upper curve.

Condition 4:

Confluent GL-261 cells were brought into contact with culture medium and 2 mg of BNF-Starch in iron and were then subjected to 10 cycles. During each cycle, a magnetic field, oscillating at a high frequency of 196 kHz, medium frequency 15 kHz, with an average magnetic field of 61 mT and maximum magnetic field of 85 mT, was applied, leading to a heating step up to 45° C., followed by the non-application of an alternating magnetic field, leading to a cooling step during which the temperature decreases from 45° C. down to 34-35° C. The times of heating and cooling steps, $t_7$ and $t_8$, as well as the low oscillation frequency, average and maximum magnetic fields deduced from $t_7$ and $t_8$ are indicated in table 5. The variations of temperatures with time during these low frequency cycles are indicated in FIG. 6(b), upper curve.

Condition 5:

Confluent GL-261 cells were brought into contact with culture medium without BNF-Starch, were then exposed to the same 10 cycles as in condition 4 with the same magnetic field, $t_7$ and $t_8$ values. The variations of temperatures with time during the low frequency cycles are shown in FIG. 6(b), bottom curve.

Condition 6:

Confluent GL-261 cells were brought into contact with culture medium and 2 mg of BNF-Starch in iron, exposed to a magnetic field, oscillating at a high frequency of 196 kHz and medium frequency of 15 kHz, with an average magnetic field varied between 53 and 61 mT and a maximum magnetic field varied between 68 and 85 mT, to reach an average temperature of 50° C. continuously during 30 minutes.

Condition 7:

Confluent GL-261 cells were brought into contact with culture medium and 2 mg in iron of BNF-Starch, were then exposed to 6 cycles. During each cycle, a magnetic field, oscillating at a high frequency of 196 kHz and medium frequency 15 kHz, with an average magnetic field of 61 mT and maximum magnetic field of 85 mT was applied, leading to a heating step up to 50° C., followed by the non-application of an alternating magnetic field to decrease the temperature from 50° C. down to 37° C. during a cooling step. The times of heating and cooling steps, $t_7$ and $t_8$, as well as the low oscillation frequency, average and maximum magnetic fields deduced from $t_7$ and $t_8$ are indicated in table 6. The variations of temperatures with time during these low frequency cycles are indicated in FIG. 6(c), upper curve.

Condition 8:

Confluent GL-261 cells were brought into contact with culture medium without BNF-Starch and exposed to the same 6 cycles as in condition 7 with the same magnetic field and same time $t_7$ and $t_8$ µs in condition 7. The variations of temperature with time during these low frequency cycles are shown in FIG. 6(c), bottom curve.

Condition 9:

Confluent GL-261 cells were brought into contact with culture medium and 2 mg of BNF-Starch in iron, exposed to a magnetic field oscillating at a high frequency of 196 kHz and medium frequency of 15 kHz, with an average magnetic field varied between 55 and 61 mT and a maximum magnetic field varied between 77 and 85 mT, to reach an average temperature of 55° C. continuously during 30 minutes.

Condition 10:

Confluent GL-261 cells were brought into contact with culture medium and 2 mg of BNF-Starch in iron, and were then exposed to 4 cycles. During each cycle, a magnetic field, oscillating at a high frequency of 196 kHz and medium frequency 15 kHz, with an average magnetic field of 61 mT and maximum magnetic field of 85 mT was applied, leading to a heating step at 55° C., followed by the non-application of an alternating magnetic field to decrease the temperature from 55° C. down to 37° C. during a cooling step. The times of heating and cooling steps, $t_7$ and $t_8$, as well as the low oscillation frequency, average and maximum magnetic fields deduced from $t_7$ and $t_8$ are indicated in table 7. The variations of temperatures with time during these low frequency cycles are indicated in FIG. 6(d), upper curve.

Condition 11:

Confluent GL-261 cells were brought into contact without the BNF-Starch, and were then exposed to the same 4 cycles as in condition 10 with same magnetic field and same time $t_7$ and $t_8$ µs in condition 10. The variations of temperature with time during these low frequency cycles are shown in FIG. 6(d), bottom curve.

Condition 12:

Confluent GL-261 cells were brought into contact with culture medium and 2 mg of BNF-Starch in iron and incubated at 37° C. for 30 min.

After treatments, the culture medium was removed, cells were rinsed with PBS, PBS was replaced with culture medium and the cells were then incubated at 37° C. in the presence of 5% $CO_2$ for 12 hours. For each condition 1 to 12 of treatment, the percentage of dead cells, living cells, and the percentage of necrotic and apoptotic cells were measured. For that, the Petri dishes were rinsed with PBS, trypsin was added to detach cells, one milliliter of culture medium was added to the cells and the mixture was centrifuged at 1000 rpm for 10 minutes. The supernatant was removed and then replaced with 200 µl of PBS in order to obtain approximately $2.10^6$ cells per ml. 5 µl of Annexin V Alexa Fluoride and 1 µl of propidium iodide at 1 mg per ml were added to the cells. After 15 minutes, 800 µl of an Annexin 1× binding buffer solution were added to the cells and the fluorescence of the mixture was measured using a flow cytometer, which makes it possible to deduce the percentage of living cells, necrotic and apoptotic cells.

For condition 2, the temperature increased by 11° C. during the 30 minutes of continuous application of the oscillating magnetic field (FIG. 6(a)). For this condition, the percentage of living cells is 92%, similar to that of 97% obtained with the untreated cells (condition 1), indicating that continuous magnetic field application leading to continuous temperature increase of 11° C. does not induce significant cell death.

For conditions 5, 8, and 11, the temperature increased, due to Eddy or Foucault currents, by 5° C. on average from 25° C. to 30° C. (condition 5, FIG. 6(b), bottom curve), by 4° C. on average from 27° C. to 31° C. (condition 8, FIG. 6(c), bottom curve), or 7° C. on average from 27° C. to 34° C. (condition 11, FIG. 6(d), bottom curve) during sequences of magnetic field application, and the temperature decreased by a relatively similar amount during sequences of non-application of the magnetic field. For these conditions, the percentage of living cells is 94%, similar to that of 97% obtained with the untreated cells (condition 1), indicating that Eddy or Foucault currents did not induce significant cell death.

For conditions 3 and 4, temperature either increased continuously during 30 minutes by 18° C. (condition 3, FIG. 6(a)) or increased by 20° C. and decreased by 10° C. during the first cycle, and increased by 10° C. and decreased by 10° C. during the remaining 9 cycles (condition 4, FIG. 6(b), upper curve). The percentage of living cells is 95% after continuous heating (condition 3) and 56% after sequential heating (condition 4), indicating that at this heating temperature of 45° C., the application of a magnetic field oscillating at a high, medium, and low frequency (condition 4) leads to enhanced toxicity towards cancer cells compared with a magnetic field oscillating at the high and medium frequency (condition 3).

For conditions 6 and 7, the temperature either increased continuously during 30 minutes by 23° C. (condition 6, FIG. 6(a)), or increased by 24° C. and decreased by 9° C. during a first cycle, and increased by 15° C. and decreased by 15° C. during the remaining 5 cycles (condition 7, FIG. 6(c), upper curve). The percentage of living cells is 91% after continuous heating (condition 6) and 0.4% after sequential conditions (condition 7), indicating that at this heating temperature of 50° C., the application of a magnetic field oscillating at high, medium, and low frequency (condition 7) leads to enhanced toxicity towards cancer cells compared with a magnetic field oscillating at the high and medium frequency (condition 6).

For conditions 9 and 10, the temperature increased continuously during 30 minutes by 28° C. (condition 9, FIG. 6(a)), or increased by 29° C. and decreased by 18° C. during the first cycle, and increased by 18° C. and decreased by 18° C. during the remaining 3 cycles (condition 10, FIG. 6(d), upper curve). The percentage of living cells is 2% after continuous heating (condition 9) and 1.6% under sequential conditions (condition 10), indicating that at this highest heating temperature of 55° C., application of magnetic fields oscillating at high, medium and low frequencies or at high and medium frequency, both lead to the destruction of most cancer cells.

For condition 12, temperature did not increase. The percentage of living cells is then 99%, indicating that the cytotoxic effect observed when nanoparticles are exposed to the oscillating magnetic field is due to the application of the magnetic field and not to nanoparticle toxicity.

We can Conclude from this Example that:

The application of a magnetic field oscillating at high, medium, and low frequency, enables to strengthen treatment safety, i) to v), to enhance treatment efficacy, vi), and to use a method that does not necessitate to vary the magnetic field strength or frequency to reach a desired temperature during the heating steps.

i) In the absence of nanoparticles, cytotoxicity induced by the alternating magnetic field, in the presence of heat generated by Eddy or Foucault currents, is not observed.

ii) In the absence of nanoparticles, the application of a magnetic field oscillating at $f_h$=195 kHz, $f_m$=15 kHz, and $f_l$=0.9-2.5 mHz, enables to heat sequentially, limiting the increase in temperature compared with the application of a field oscillating at $f_h$=195 kHz and $f_m$=15 kHz. Increase in temperature, due to Eddy or Foucault currents, is 11° C. under the application of a magnetic field oscillating at $f_h$=195 kHz and $f_m$=15 kHz compared to 6-8° C. under the application of a magnetic field oscillating at $f_h$=195 kHz, $f_m$=15 kHz and $f_l$=0.9-2.5 mHz.

iii) For a magnetic field, oscillating at $f_h$=195 kHz, $f_m$=15 kHz and $f_l$=0.9-2.5 mHz, the average magnetic field is 31-44 mT, compared with 61 mT for a magnetic field oscillating at $f_h$=195 kHz, $f_m$=15 kHz. It is therefore possible to decrease the average magnetic field by a factor of ~1.4-2 by adding a low frequency and therefore decrease potential toxicity associated with the application of a too high average magnetic field.

iv) Temperatures of 44-45° C. are reached during 33 seconds using a magnetic field, oscillating at $f_h$=195 kHz, $f_m$=15 kHz, and $f_l$=1.6-2.5 mHz (FIG. 6(b)), whereas these temperatures are reached during 24 minutes using a magnetic field oscillating at $f_h$=195 kHz, $f_m$=15 kHz (FIG. 6(a)). Temperatures of 49-50° C. are reached during 47 seconds using a magnetic field, oscillating at $f_h$=195 kHz, $f_m$=15 kHz, and $f_l$=1.2-1.7 mHz (FIG. 6(c)), whereas these temperatures are reached during 23 minutes using a magnetic field oscillating at $f_h$=195 kHz, $f_m$=15 kHz (FIG. 6(a)). Temperatures of 52.5-53.5° C. are reached during 55 seconds using a magnetic field, oscillating at $f_h$=195 kHz, $f_m$=15 kHz, and $f_l$=0.9-1.1 mHz (FIG. 6(d)), whereas these temperatures are reached during 16 minutes using a magnetic field oscillating at $f_h$=195 kHz, $f_m$=15 kHz (FIG. 6(a)). Using a low oscillation frequency enables to decrease the time during which maximum temperature is achieved by a factor of 17 to 44, compared with the application of an oscillating magnetic field without the low frequency. This should enhance treatment safety and does not reduce the efficacy of cell destruction by the magnetic field.

v) The application of a magnetic field, oscillating at high, medium, and low frequency, enables to obtain a series of temperature gradient increase (+ΔT) followed by temperature gradient decrease (−ΔT). Temperatures of 44-45° C. were reached 10 times following ΔT of 8-20° C. followed by −ΔT of 8-10° C. by applying a magnetic field, oscillating at $f_h$=195 kHz, $f_m$=15 kHz, and $f_l$=1.6-2.5 mHz (FIG. 6(b)), whereas temperatures of 44-45° C. were reached only once following ΔT of 17-20° C. by applying a magnetic field, oscillating at $f_h$=195 kHz, $f_m$=15 kHz. Enhanced efficacy observed using the magnetic field oscillating at $f_h$, $f_m$, and $f_l$, can be explained by the larger number of (+ΔT) and (−ΔT), compared with the magnetic field oscillating only at $f_h$ and $f_m$.

vi) When cancer cells are brought into contact with nanoparticles and heated to a temperature, which is below 55° C., the application of a magnetic field, oscillating at a high, medium, and low frequency leads to enhanced cytotoxicity compared with the application of a magnetic field, oscillating at high and medium frequencies.

vii) The application of a magnetic field enables a treatment where the number of sequences of magnetic field application, the number of sequences of non-application of the magnetic field, the average and maximum magnetic fields, the frequency of the applied magnetic field, the times of application and non-application of the magnetic field, are fixed at the beginning of the treatment depending on the temperature that one desires to reach. With this method, it is not necessary to vary the magnetic field strength or amplitude to reach a desired temperature during a sequence of magnetic field application. Moreover, once the cycles with associated heating and cooling times have been estimated, it is not necessary to measure the temperature during treatments. Cycles with defined heating and cooling times can be used for the treatment.

Example 4: Application of a Magnetic Field, Oscillating at a High Frequency of 196 kHz, Medium Frequency of 15 Hz, and Low Frequency of 4-25 mHz, for Efficient In Vivo Destruction of Tumors Using a 1 mL 25 g syringe, a volume of 100 µl containing $10^7$ GL-261 murine glioblastoma cells was administered subcutaneously on the left flank, between the paw and the back of female mice black 6 C57BL/6J. The tumors grew during 10 to 15 days until they reached a size of 60 to 90 mm$^3$. When the tumors reached this size, the mice were anesthetized with isoflurane gas and maintained at 37° C. by using heating plates. Using the same syringe, 50 µl of a suspension of BNF-starch nanoparticles at an iron concentration of 50 mg/mL were administered at the center of the tumors. The suspension of BNF-Starch was administered at a quantity of 25·t, measured in µg of iron comprised in nanoparticles, where t is the size of the treated tumors in mm$^3$. Three different groups of mice were treated as follows:

A first group of 4 mice was exposed to 21 hyperthermia sessions, lasting 7 weeks with 3 sessions per week. Each session of hyperthermia consisted in 4 to 86 cycles (table 8). At the beginning of each cycle, to initiate the heating step, a magnetic field, oscillating at high and medium frequency, with $f_h$=195 kHz, $f_m$=15 kHz, $H_{av}$=27 mT and $H_{max}$=57 mT was switched on during a time $t_7$. As soon as the intra-tumor temperature reached 39.3-47.4° C., the oscillating magnetic field was stopped and the cooling step started to allow the intratumor temperature to decrease to 35-37.9° C. Cycles were repeated until a total exposure time of about 20 minutes was obtained for each hyperthermia session. The heating and cooling times, $t_7$ and $t_8$, measured during the different cycles of each hyperthermia session, as well as $H_{av}$, $H_{max}$, and $f_l$, deduced from the values of $t_7$ and $t_8$ are indicated in table 8 and are average values among the 4 mice.

A second group of 10 mice was exposed to 15 hyperthermia sessions, lasting 5 weeks, with 3 sessions per week. Each session of hyperthermia consisted in 30 minutes of application of a magnetic field, oscillating at $f_h$=202 kHz, $f_m$=15 kHz, $H_{av}$=24-31 mT and $H_{max}$=54-67 mT to target an intratumor temperature of 37-48° C. For the first hyperthermia session, the targeted intratumor temperature was always reached while for subsequent hyperthermia sessions, it was not always possible to reach the targeted intratumor temperature and the average and maximum magnetic fields were then set at $H_{av}$=31 mT and $H_{max}$=67 mT, with $f_h$=202 kHz and $f_m$=15 kHz. For mice in which tumor volumes exceeded 150% of initial tumor sizes and targeted temperature of 43-46° C. was not reached, mice received a second intratumor nanoparticle administration of BNF-Starch at 25 µg in iron of nanoparticles per mm$^3$ of tumor.

A third group of 10 mice was not treated further following BNF-Starch administration.

In groups 1 and 2, the intra-tumor temperature was measured using an optical fiber positioned at the center of the tumors (Luxtron, LumaSense Technologies). In the groups, mice were euthanized when/if mouse weight had decreased by more than 20%.

Figure 7:
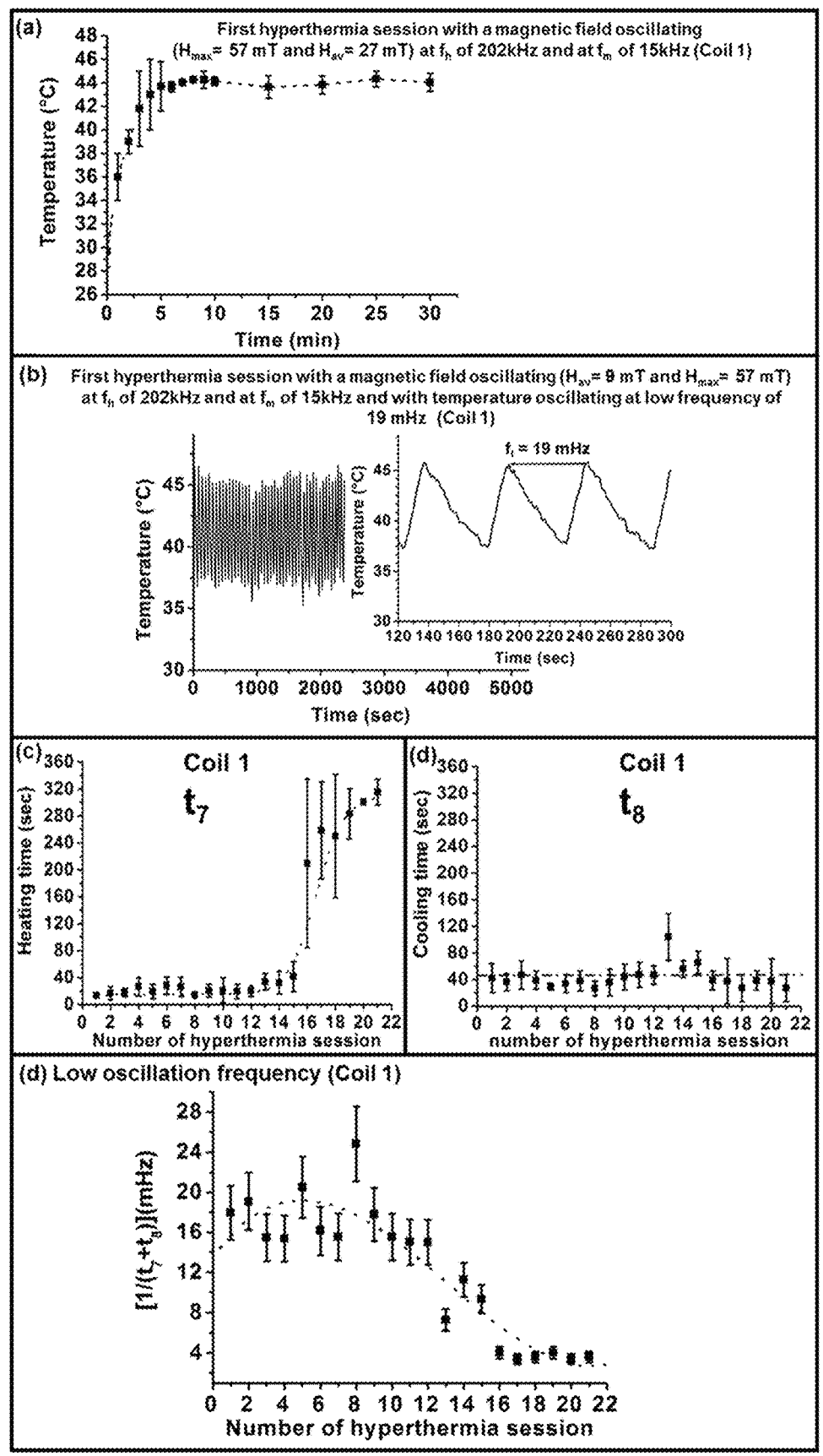
FIG. 7: (a), For the first hyperthermia session, temperature variation as a function of time of 25 µg in iron of BNF-Starch per mm³ of tumor introduced to GL-261 tumors and exposed continuously during 30 minutes to a magnetic field, oscillating at $f_h$=202 kHz and $f_m$=15 kHz, with $H_{av}$=27 mT and $H_{max}$=57 mT. 14 additional hyperthermia sessions during which a magnetic field, oscillating at $f_h$=202 kHz and $f_m$=15 kHz, with $H_{av}$=24-31 mT and $H_{max}$=54-67 mT, followed the first hyperthermia session. (b), For the first hyperthermia session, temperature variation as a function of time of 25 µg in iron of BNF-Starch per mm³ of tumor introduced to GL-261 tumors and exposed during 20 minutes to a magnetic field, oscillating at $f_h$=202 kHz, $f_m$=15 kHz, with $H_{av}$=11 mT and $H_{max}$=57 mT, applied during $t_7$, followed by non-application of the magnetic field during $t_8$. 20 hyperthermia sessions of 20 minutes each followed the first hyperthermia session, during which a magnetic field, oscillating at $f_h$=202 kHz, $f_m$=15 kHz and $f_l$=19 $10^{-3}$ Hz was applied. The times $t_7$ and $t_8$ associated to heating and cooling steps of the different cycles are indicated in table 8. (c) Heating times $t_7$ µs a function of the hyperthermia session. (d), Cooling times $t_8$ as a function of the hyperthermia session. (e), Low frequency of oscillation, $f_l$=[1/($t_7$+$t_8$)], as a function of the hyperthermia session.

For group 1, the heating and cooling times, $t_7$ and $t_8$, are presented as a function of the number of hyperthermia session in FIGS. 7(c) and 7(d). The heating time is observed to be relatively low and constant at 20 seconds during the 13 first hyperthermia sessions and then it strongly increases from 20 seconds to 320 seconds between the 13$^{th}$ and 22$^{nd}$ hyperthermia session, which may be due to BNF-Starch progressively leaving the tumor and/or being degraded following the 13$^{th}$ hyperthermia session. A lower quantity of nanoparticles in the tumor would indeed require longer heating times to reach similar temperatures. By contrast, the cooling time remains relatively constant at 40 seconds, during the various hyperthermia sessions, suggesting that the cooling time does not depend on nanoparticle distribution and/or degradation. Instead, it may indeed depend on the environment of the nanoparticles such as type of tissue, organ, or blood irrigation of the tumor. The low frequency of oscillation is plotted as a function of number of hyperthermia session in FIG. 7(d). It is relatively constant and high at 16 $10^{-3}$ Hz during the first 10 hyperthermia sessions and decreases down to 4 $10^{-3}$ Hz between the 10$^{th}$ and 22$^{nd}$ hyperthermia session. This seems to indicate that to reach sufficiently high low frequency of oscillation, which may be necessary to reach antitumor activity, nanoparticle concentration should be sufficiently high and/or nanoparticles should not be degraded.

Figure 8:
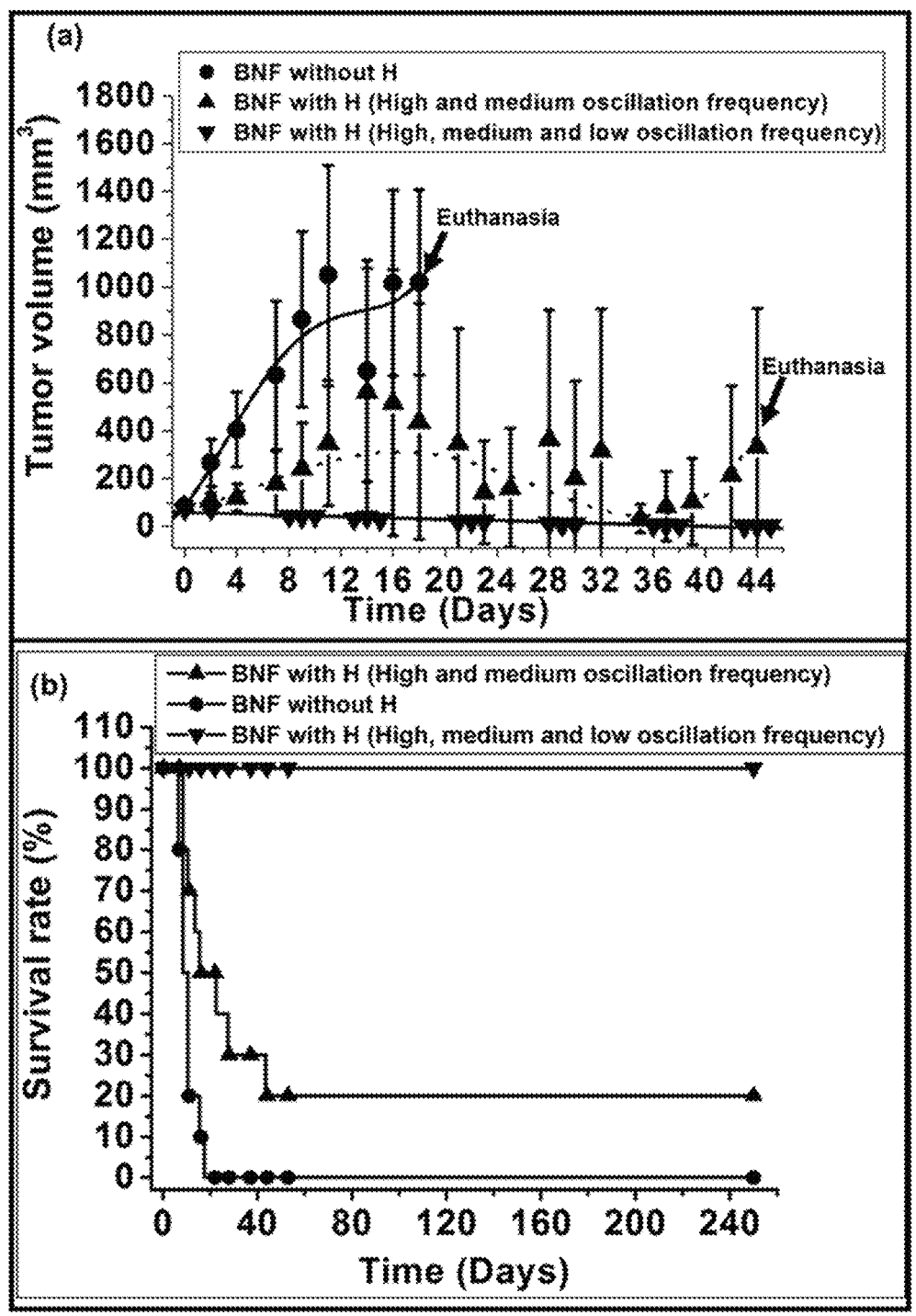
FIG. 8: (a), Variation of the tumor volume as a function of time (days) following day 0, the day of BNF-Starch administration, where BNF-Starch are either administered without application of a magnetic field, (●), BNF-Starch are administered followed by 15 hyperthermia session (3 per week) during which a magnetic field oscillating at $f_h$=202 kHz and $f_m$=15 kHz with $H_{av}$=24-31 mT and $H_{max}$=54-67 mT is applied during 30 minutes, (▲), BNF-Starch are administered followed by 21 hyperthermia sessions (3 per week) during which a magnetic field oscillating at $f_h$=202 kHz, $f_m$=15 kHz, $f_l$=4-25 mHz with $H_{av}$=7-23 mT and $H_{max}$=57 mT is applied during 20 minutes, (▼). (b), Mouse survival rate as a function of time (days) following day 0, the day of BNF-Starch administration, where BNF-Starch are either administered without application of a magnetic field, (●), BNF-Starch are administered followed by 15 hyperthermia session (3 per week) during which a magnetic field oscillating at $f_h$=202 kHz and $f_m$=15 kHz with $H_{av}$=24-31 mT and $H_{max}$=54-67 mT is applied during 30 minutes, (▲), BNF-Starch are administered followed by 21 hyperthermia sessions (3 per week) during which a magnetic field oscillating at $f_h$=202 kHz, $f_m$=15 kHz, $f_l$=4-25 mHz with $H_{av}$=7-23 mT and $H_{max}$=57 mT is applied during 20 minutes, (▼).
Figure 9:
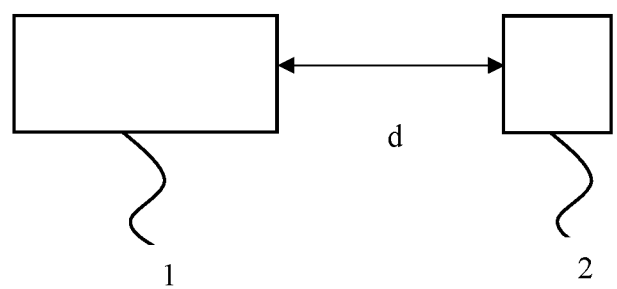
FIG. 9: A schematic illustration of a device (1) that generates an oscillating magnetic field located at a distance (d) of more than 1 cm from a body part (2).

Length and width of the tumors, L and l, were measured in the different mice using a caliper every 2 days and the tumor volume was estimated using the formula; $V_{tumoral}$=0.5 (L·l$^2$). Average tumor volumes of the three groups of mice are plotted as a function of time following day 0 (the day of BNF-Starch administration) in FIG. 8(a). Average tumor volumes strongly increase for group 3 and mice are euthanized at day 16, suggesting the absence of antitumor activity in group 3 (FIGS. 8(a) and 8(b)). Average tumor volumes increase less significantly in group 2 than in group 3 (FIG. 8(a)) and 20% of mice are still alive 245 days following BNF-Starch administration in group 2 (FIG. 8(b)), suggesting partial antitumor activity in group 2. Average tumor volumes decrease to zero at day 44 for group 1 and 100% of mice of group 1 are still alive 245 days following BNF-Starch administration (FIG. 8(b)), showing strong antitumor activity for group 1.

We can Conclude from this Example that:

i) By heating magnetic nanoparticles comprised in tumors using a magnetic field oscillating at three frequencies ($f_h$=202 kHz, $f_m$=15 kHz, and $f_l$=4-25 mHz), it was possible to reach stronger antitumor efficacy than by using a magnetic field oscillating at two frequencies ($f_h$=202 kHz and $f_m$=15 kHz).

ii) When we used a magnetic field oscillating at three frequencies ($f_h$=202 kHz, $f_m$=15 kHz, and $f_l$=4-25 mHz), it was possible to reach strong antitumor efficacy without nanoparticle re-administration, whereas when we used a magnetic field oscillating at two frequencies ($f_h$=202 kHz and $f_m$=15 kHz), partial antitumor activity could only be reached when nanoparticles were re-administered. This suggests that the application of a magnetic field oscillating at three frequencies ($f_h$=202 kHz, $f_m$=15 kHz, and $f_l$=4-25 mHz) leads to nanoparticles being less degraded and/or leaving less rapidly the tumor than the application of a magnetic field oscillating at two frequencies ($f_h$=202 kHz and $f_m$=15 kHz).

iii) The heating time increases with the number of hyperthermia session and therefore seems to depend on nanoparticle concentration, whereas the cooling time remains relatively constant during the various hyperthermia sessions and therefore seems to be independent from nanoparticle concentration.

iv) The low frequency of oscillation is higher or larger during the first to $11^{th}$ hyperthermia sessions at $16\ 10^{-3}$ Hz than between the $16^{th}$ and $22^{nd}$ hyperthermia session, where $f_l$ is $4\ 10^{-3}$ Hz. This suggests that as the nanoparticle progressively leave the tumor and/or are degraded, $f_l$ decreases.

TABLE 1

Properties of the different coils when magnetic field stabilized
Measurement of $f_m$, $f_b$, $H_{max}$ and $H_{av}$ at the center of each coil

| Coil | $f_{oc}$ (kHz) | $f_x$ (kHz) | Length (cm) | Diameter (cm) | I (A) | $H_{coxt}$ (mT) | $H_{av}$ (mT) | $H_{coxt}/H_{av}$ | Number of turns |
|---|---|---|---|---|---|---|---|---|---|
| 1 | 15 | 202 | 3.5 | 7 | 190 | 58 | 26 | 2.2 | 4 |
| 2 | 15 | 195 | 4 | 7 | 195 | 34 | 25 | 1.4 | 4 |
| 3 | 15 | 231 | 3.5 | 3 | 73 | 53 | 26 | 2.0 | 2 coils of four tunrs one in the other |
| 4 | 15 | 329 | 2 | 3.5 | 149 | 56 | 24 | 2.3 | 3 |
| 5 | 2 | 91 | 15 | 28 | 682 | 33 | 26 | 1.3 | 3 |

TABLE 2

Magnetic heating properties ($f_h$, $f_m$, $H_{max}$, $H_{av}$ as indicated in table 1)

| | M-PLL | | BNF | |
|---|---|---|---|---|
| Coil | ΔT (° C.) | S AR (W/$g_{Fe}$) | ΔT (° C.) | S AR (W/$g_{Fe}$) |
| 1 | 71 | 244 | | |
| 2 | 57 | 84 | 7 | 8 |
| 3 | 68 | 202 | | |
| 4 | 75 | 192 | 12 | 13 |
| 5 | 5 | 6 | | |

TABLE 3

Conditions of magnetic field application when magnetic field stabilized
Measurement of $f_m$, $f_b$, $H_{max}$ and $H_{av}$ at 5 cm and 8 cm from the edge of coil 2

| Coil | Current intensity (Å) | $f_k$ (kHz) | $f_m$ (kHz) | Distance from the edge of the coil (cm) | $H_{coxt}$ (mT) | $H_{av}$ (mT) | $H_{max}/H_{av}$ |
|---|---|---|---|---|---|---|---|
| 2 | 550 | 192 | None | 5 | 13 | 12 | 1.1 |
| | | 189 | None | 8 | 5 | 5 | 1.1 |

TABLE 4

SIGMA nanoparticles heating properties as a function of the distance from the edge of the coil 2 ($f_h$, $f_m$, $H_{max}$, $H_{av}$ as indicated in table 3)

| Concentration in iron (mg/mL) | Distance from the edge of the coil (cm) | ΔT (° C.) | SAR (W/$g_{Fe}$) |
|---|---|---|---|
| 422 | 5 | 45 | 2 |
|  | 8 | 8 | 0.4 |
| 194 | 5 | 29 | 2 |
|  | 8 | 5 | 0.5 |
| 87 | 5 | 15 | 3 |
|  | 8 | 1 | 0.4 |
| 57 | 5 | 13 | 3 |
|  | 8 | 1 | 0.6 |

TABLE 5

Treatments of GL-261 cells brought into contact with 2 mg of chemical nanoparticles (BNF-Starch), exposed during $t_7$ to a magnetic field oscillating at $f_h$ = 196 kHz and $f_m$ = 15 kHz with $H_{max}$ = 85 mT and $H_{av}$ = 61 mT to reach 45° C., followed by the non application of the magnetic field during $t_8$. (Coil 2)

| Cycle | Time of application of the magnetic field, $t_7$ (heating steps) | Time of non-application of the magnetic field, $t_8$ (cooling steps) | $H_{av}$ (mT) | $H_{max}$ (mT) | $f_l$ (mHz) |
|---|---|---|---|---|---|
| 1 | 7 minutes 23 secondes | 2 minutes 57 secondes | 44 | 85 | 1.61 |
| 2 | 3 minutes 31 secondes | 3 minutes 23 secondes | 31 | 85 | 2.42 |
| 3 | 3 minutes 21 secondes | 3 minutes 17 secondes | 31 | 85 | 2.51 |
| 4 | 3 minutes 30 secondes | 3 minutes 9 secondes | 32 | 85 | 2.51 |
| 5 | 3 minutes 27 secondes | 3 minutes 25 secondes | 31 | 85 | 2.43 |
| 6 | 3 minutes 34 secondes | 3 minutes 10 secondes | 32 | 85 | 2.48 |
| 7 | 3 minutes 35 secondes | 3 minutes 6 secondes | 33 | 85 | 2.49 |
| 8 | 3 minutes 40 secondes | 3 minutes 30 secondes | 31 | 85 | 2.33 |
| 9 | 3 minutes 45 secondes | 3 minutes 36 secondes | 31 | 85 | 2.27 |
| 10 | 3 minutes 42 secondes | 3 minutes 36 secondes | 31 | 85 | 2.28 |

TABLE 6

Treatments of GL-261 cells brought into contact with 2 mg of chemical nanoparticles (BNF-Starch), exposed during $t_7$ to a magnetic field oscillating at $f_h$ = 196 kHz and $f_m$ = 15 kHz with $H_{max}$ = 85 mT and $H_{av}$ = 61 mT to reach 50° C., followed by the non application of the magnetic field during $t_8$. (Coil 2)

| Cycle | Time of application of the magnetic field, $t_7$ (heating step) | Time of non-application of the magnetic field, $t_8$ (cooling step) | $H_{av}$ (mT) | $H_{max}$ (mT) | $f_l$ (mHz) |
|---|---|---|---|---|---|
| 1 | 9 minutes 07 secondes | 4 minutes 12 secondes | 42 | 85 | 1.25 |
| 2 | 5 minutes 09 secondes | 4 minutes 25 secondes | 33 | 85 | 1.74 |
| 3 | 5 minutes 42 secondes | 4 minutes 32 secondes | 34 | 85 | 1.63 |
| 4 | 5 minutes 36 secondes | 4 minutes 40 secondes | 33 | 85 | 1.62 |
| 5 | 5 minutes 34 secondes | 4 minutes 37 secondes | 33 | 85 | 1.64 |
| 6 | 5 minutes 34 secondes | 4 minutes 37 secondes | 33 | 85 | 1.64 |

TABLE 7

Treatments of GL-261 cells brought into contact with 2 mg of chemical nanoparticles (BNF-Starch), exposed during $t_7$ to a magnetic field oscillating at $f_h$ = 196 kHz and $f_m$ = 15 kHz with $H_{max}$ = 85 mT and $H_{av}$ = 61 mT to reach 55° C., followed by the non application of the magnetic field during $t_8$. (Coil 2)

| Cycle | Time of application of the magnetic field, $t_7$ (heating step) | Time of non-application of the magnetic field, $t_8$ (cooling step) | $H_{av}$ (mT) | $H_{max}$ (mT) | $f_l$ (mHz) |
|---|---|---|---|---|---|
| 1 | 11 minutes 56 secondes | 5 minutes 54 secondes | 41 | 85 | 0.93 |
| 2 | 8 minutes 49 secondes | 5 minutes 49 secondes | 37 | 85 | 1.14 |
| 3 | 8 minutes 40 secondes | 5 minutes 50 secondes | 36 | 85 | 1.15 |
| 4 | 9 minutes 15 secondes | 5 minutes 23 secondes | 39 | 85 | 1.14 |

TABLE 8

Treatments of GL-261 tumors of 60-80 mm³ by administration of 25 μg/mm³ in iron of BNF-Starch, followed by application of a magnetic field, oscillating at $f_k$ = 202 kHz and $f_m$ = 15 kHz with $H_{max}$ = 57 mT and $H_{av}$ = 27 mT during $t_7$ to a magnetic field oscillating to reach 45° C., following by the non application of the magnetic field during $t_8$.
(Coil 1)

| Hyperthermia | Cycle | Time of application of the magnetic field, $t_7$ (heating step) | Maximum temperature reached during heating steps (° C.) | Time of non-application of the magnetic field, $t_8$ (cooling step) | Minimum temperature reached during cooling steps (° C.) | $H_{av}$ (mT) | $H_{max}$ (mT) | $f_t$ (mHz) |
|---|---|---|---|---|---|---|---|---|
| 1 | 1 | 20 sec. | 46.4-47.4 | 41 sec. | 36.5-37.5 | 9 | 57 | 16 |
|  | 2 to 86 | 14 sec. | 45-46.4 | 42 sec. | 36-37.5 | 7 | 57 | 18 |
| 2 | 1 | 16 sec. | 44.4-46 | 37 sec. | 36.4-37.9 | 8 | 57 | 19 |
|  | 2 to 71 | 16 sec. | 45.2-46.9 | 36 sec. | 36.7-37.5 | 8 | 57 | 19 |
| 3 | 1 | 26 sec. | 43.8-45.7 | 47 sec. | 36-38.3 | 10 | 57 | 14 |
|  | 2 to 64 | 18 sec. | 44.3-45.6 | 47 sec. | 36.3-37.3 | 7 | 57 | 15 |
| 4 | 1 | 26 sec. | 43.8-47.2 | 39 sec. | 36.7-37.1 | 11 | 57 | 15 |
|  | 2 to 32 | 37 sec. | 45-45.4 | 35 sec. | 36.2-37.4 | 14 | 57 | 14 |
| 5 | 1 | 19 sec. | 44.5-45.4 | 29 sec. | 36.6-37.7 | 11 | 57 | 21 |
|  | 2 to 34 | 35 sec. | 44.6-45.4 | 33 sec. | 37.3-37.6 | 14 | 57 | 15 |
| 6 | 1 | 28 sec. | 44.7-46 | 33 sec. | 37-37.5 | 12 | 57 | 16 |
|  | 2 to 35 | 32 sec. | 44.6-45.9 | 39 sec. | 37.3-37.6 | 12 | 57 | 14 |
| 7 | 1 | 33 sec. | 44-44.8 | 41 sec. | 34-37.6 | 12 | 57 | 14 |
|  | 2 to 34 | 26 sec. | 44.4-45.2 | 38 sec. | 37-37.4 | 11 | 57 | 16 |
| 8 | 1 | 14 sec. | 45.2-46.4 | 26 sec. | 36.6-37.6 | 9 | 57 | 25 |
|  | 2 to 84 | 18 sec. | 44.9-45.5 | 25 sec. | 35.9-36.8 | 11 | 57 | 23 |
| 9 | 1 | 28 sec. | 44.5-45.1 | 43 sec. | 36.8-37.3 | 11 | 57 | 14 |
|  | 2 to 57 | 21 sec. | 44.4-45.1 | 36 sec. | 36.7-37.1 | 10 | 57 | 18 |
| 10 | 1 | 34 sec. | 44.9-47 | 37 sec. | 36-37.6 | 13 | 57 | 14 |
|  | 2 to 49 | 24 sec. | 44.6-46.3 | 49 sec. | 36.3-37 | 9 | 57 | 14 |
| 11 | 1 | 28 sec. | 45.1-46 | 47 sec. | 36.3-37.4 | 10 | 57 | 13 |
|  | 2 to 60 | 19 sec. | 44-45.3 | 47 sec. | 36.3-37.2 | 8 | 57 | 15 |
| 12 | 1 | 28 sec. | 44.7-45.8 | 51 sec. | 36.4-37.3 | 10 | 57 | 13 |
|  | 2 to 58 | 20 sec. | 44.4-45.1 | 47 sec. | 36.6-37.4 | 8 | 57 | 15 |
| 13 | 1 | 38 sec. | 44.8-47 | 76 sec. | 36-37.6 | 9 | 57 | 9 |
|  | 2 to 34 | 34 sec. | 44.6-45.2 | 104 sec. | 36.4-37.1 | 7 | 57 | 7 |
| 14 | 1 | 38 sec. | 44.3-46.4 | 58 sec. | 35.7-36.8 | 11 | 57 | 10 |
|  | 2 to 36 | 33 sec. | 44.3-45 | 56 sec. | 36.2-36.9 | 10 | 57 | 11 |
| 15 | 1 | 43 sec. | 44.5-47 | 72 sec. | 36.8-37.1 | 10 | 57 | 9 |
|  | 2 to 28 | 41 sec. | 44.6-45 | 65 sec. | 36.5-36.8 | 10 | 57 | 9 |
| 16 | 1 | 143 sec. | 39.6-44.9 | 83 sec. | 35-36.9 | 17 | 57 | 4 |
|  | 2 to 4 | 210 sec. | 39.3-44.6 | 32 sec. | 35.6-36.8 | 23 | 57 | 4 |
| 17 |  |  | Same as cycle 16 |  |  |  |  |  |
| 18 |  |  |  |  |  |  |  |  |
| 19 |  |  |  |  |  |  |  |  |
| 20 |  |  |  |  |  |  |  |  |
| 21 |  |  |  |  |  |  |  |  |

TABLE 9

Treatments of GL-261 tumors of 60-80 mm³ by administration of 25 μg/mm³ in iron of BNF-Starch, followed by application of a magnetic field, oscillating at $f_h$ = 202 kHz and $f_m$ = 15 kHz. (Coil 1)

| Hyperthermia | Maximum temperature reached during heating steps (° C.) | Nanoparticules admininistration | $H_{av}$ (mT) | $H_{max}$ (mT) |
|---|---|---|---|---|
| 1 | 40-46 | yes | 24-31 | 54-67 |
| 2 | 32-46 | no | 25-27 | 54-57 |
| 3 | 31-48 | no | 25-27 | 54-57 |
| 4 | 31-47.8 | yes | 24-31 | 54-67 |
| 5 | 37-47.5 | no | 25-27 | 54-57 |
| 6 | 37-47.6 | no | 25-27 | 54-57 |
| 7 | 37-47.7 | yes | 24-31 | 54-67 |
| 8 | 37-47.8 | no | 25-27 | 54-57 |
| 9 | 37-47.9 | no | 25-27 | 54-57 |
| 10 | 37-47.1 | no | 25-27 | 54-57 |
| 11 | 37-47.1 | no | 25-27 | 54-57 |
| 12 | 37-47.1 | no | 25-27 | 54-57 |
| 13 | 37-47.1 | no | 25-27 | 54-57 |
| 14 | 37-47.1 | no | 25-27 | 54-57 |
| 15 | 37-47.1 | no | 25-27 | 54-57 |

The invention claimed is:

1. A method of therapeutic treatment, prophylactic treatment, cosmetic treatment, or diagnosis of an individual in which magnetic particles are exposed to an oscillating magnetic field, comprising:
   administering the magnetic nanoparticles to a body part of an individual in need thereof; and
   applying to the body part a magnetic field oscillating either:

(a) at a high frequency, at a medium frequency, and at a low frequency, or (b) at a high frequency and at a low frequency, wherein the high frequency applied in (a) or (b) is 1 MHz at most, wherein the medium frequency applied in (a) is lower than the high frequency, wherein the low frequency applied in (a) or (b) is lower than the high frequency, and the low frequency applied in (a) is lower than the medium frequency, wherein applying the oscillating magnetic field at the low frequency in (a) or (b) is part of a repetition of at least one cycle of applying the oscillating magnetic field at the low frequency, and wherein the at least one cycle of applying the oscillating magnetic field at the low frequency has at least one property selected from the group consisting of:

(i) the at least one cycle of applying the oscillating magnetic field at the low frequency comprises a heating step in which the oscillating magnetic field at the low frequency induces heating and a cooling step in which the oscillating magnetic field at the low frequency induces cooling, and (ii) the at least one cycle of applying the oscillating magnetic field at the low frequency comprises a step with increasing oscillating magnetic field strength at the low frequency and a step with decreasing the oscillating magnetic field strength at the low frequency, and wherein applying the oscillating magnetic field induces at least one of a temperature increase or a movement of the magnetic nanoparticles to cause internalization or externalization of the magnetic nanoparticles from cells or death of cells in the body part to provide the therapeutic treatment, prophylactic treatment, cosmetic treatment, or diagnosis.

2. The method according to claim 1, wherein the magnetic nanoparticles have a specific absorption rate (SAR) higher than 1 W/g.

3. The method according to claim 1, wherein the high frequency is between 1 and 1,000 kHz.

4. The method according to claim 3, wherein the high frequency heats the magnetic nanoparticles.

5. The method according to claim 1, wherein the applied magnetic field oscillates at the high frequency, at the medium frequency, and at the low frequency, and wherein the medium frequency is between $10^{-5}$ and $5 \times 10^5$ Hz.

6. The method according to claim 1, wherein the applied magnetic field oscillates at the high frequency, at the medium frequency, and at the low frequency, and the medium frequency modulates the high frequency.

7. The method according to claim 1, wherein the applied magnetic field oscillates at the high frequency, at the medium frequency, and at the low frequency, and the medium frequency increases heating properties of the magnetic nanoparticles.

8. The method according to claim 1, wherein the low frequency is between $10^{-9}$ and $5 \times 10^5$ Hz.

9. The method according to claim 1, wherein the heating step produces a temperature increase of more than 1° C. of the body part.

10. The method according to claim 1, wherein the cooling step induces a temperature decrease of more than 1° C. of the body part.

11. The method according to claim 1, wherein the applied magnetic field oscillates either:

(a) at the high frequency, at the medium frequency, and at the low frequency, wherein both the medium and the low frequency increases a ratio between a maximum and an average amplitude of the applied magnetic field or (b) at the high frequency and at the low frequency, wherein the low frequency increases a ratio between a maximum and an average amplitude of the applied magnetic field.

12. The method according to claim 1, wherein the applied magnetic field oscillates either:

(a) at the high frequency, at the medium frequency, and at the low frequency, wherein both the medium and the low frequency decreases diffusion of the magnetic nanoparticles outside of the body part, or (b) at the high frequency and at the low frequency, wherein the low frequency decreases diffusion of the magnetic nanoparticles outside of the body part.

13. The method according to claim 1, wherein a compound is bonded or linked to each of the magnetic nanoparticles before the oscillating magnetic field is applied, and the applied magnetic field oscillates either:

(a) at the high frequency, at the medium frequency, and at the low frequency, wherein both the medium frequency and the low frequency causes release of the compound, or (b) at the high frequency and at the low frequency, wherein the low frequency causes release of the compound.

14. The method according to claim 1, wherein the at least one cycle of applying the oscillating magnetic field at the low frequency comprises the heating step and the cooling step, and wherein: i) a maximum temperature and a minimum temperature is reached during the heating step and the cooling step, respectively, and ii) at least one parameter of the magnetic field that modulates temperature is set at a first value to reach the maximum temperature during the heating step and then the at least one parameter of the magnetic field is set at a second value to reach the minimum temperature during the cooling step.

15. The method according to claim 14, wherein the at least one parameter is selected from the group consisting of: average or maximum magnetic field amplitude, magnetic field strength, magnetic field amplitude, magnetic field frequency, and spatial or temporal distribution of magnetic field lines.

16. The method according to claim 1, wherein the method of therapeutic treatment, prophylactic treatment, cosmetic treatment, or diagnosis is for therapeutic treatment, prophylactic treatment, cosmetic treatment, or diagnosis of a disease selected from the group consisting of a cancer, a tumor, and an infection.

17. The method according to claim 1, wherein applying to the body part a magnetic field oscillating either:

(a) at the high frequency, at the medium frequency, and at the low frequency or (b) at the high frequency and at the low frequency is performed using a device generating the oscillating magnetic field located a distance of more than 50 cm from the body part.

18. The method according to claim 1, wherein the at least one cycle of applying the oscillating magnetic field at a low frequency comprises the heating step and the cooling step, and at least one of the heating step or the cooling step is performed for less than 1 day.

19. The method according to claim 1, wherein the at least one cycle of applying the oscillating magnetic field at a low frequency comprises the heating step and the cooling step, and the heating step is carried out for a duration that is short enough to limit Eddy or Foucault currents or toxic effects associated with applying the oscillating magnetic field to the body part.

20. A device suitable for magnetic hyperthermia comprising a generator of an oscillating magnetic field configured to oscillate at frequencies as high as 1 MHz and as low as $10^{-9}$ Hz.

21. The device according to claim 20, wherein the generator of the oscillating magnetic field is configured to generate an oscillating magnetic field that is able to reach a body part to be treated by magnetic hyperthermia that is located a distance of more than 1 cm from the generator.

* * * * *